United States Patent
Behlke et al.

(10) Patent No.: US 9,506,059 B2
(45) Date of Patent: *Nov. 29, 2016

(54) MODIFICATIONS FOR ANTISENSE COMPOUNDS

(71) Applicant: Integrated DNA Technologies, Inc., Coralville, IA (US)

(72) Inventors: Mark Aaron Behlke, Coralville, IA (US); Richard Owczarzy, Coralville, IA (US); Yong You, Iowa City, IA (US); Joseph Alan Walder, Chicago, IL (US); Kim Lennox, North Liberty, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/281,646

(22) Filed: Sep. 26, 2014

(65) Prior Publication Data

US 2015/0011744 A1    Jan. 8, 2015

Related U.S. Application Data

(63) Continuation of application No. 13/227,286, filed on Sep. 7, 2011, now abandoned, and application No. 14/281,646, which is a continuation-in-part of application No. 13/073,866, filed on Mar. 28, 2011, now Pat. No. 8,916,345.

(60) Provisional application No. 61/380,586, filed on Sep. 7, 2010, provisional application No. 61/318,043, filed on Mar. 26, 2010.

(51) Int. Cl.
*C12P 19/34* (2006.01)
*C12N 15/113* (2010.01)
*C12N 15/11* (2006.01)

(52) U.S. Cl.
CPC .......... *C12N 15/113* (2013.01); *C12N 15/111* (2013.01); *C12N 2310/11* (2013.01); *C12N 2310/315* (2013.01); *C12N 2310/344* (2013.01); *C12N 2310/352* (2013.01); *C12N 2310/3529* (2013.01); *C12N 2320/51* (2013.01)

(58) Field of Classification Search
USPC ............ 435/6.1, 6.12, 91.1, 91.31; 436/501; 536/23.1, 24.5, 24.3, 26.6
See application file for complete search history.

(56) References Cited

U.S. PATENT DOCUMENTS

| | | |
|---|---|---|
| 2,264,303 A | 12/1941 | Dickey |
| 3,218,309 A | 11/1965 | Elslager et al. |
| 3,407,189 A | 10/1968 | Merian |
| 3,970,617 A | 7/1976 | Bruno |
| 4,358,535 A | 11/1982 | Falkow et al. |
| 4,439,356 A | 3/1984 | Khanna et al. |
| 4,683,194 A | 7/1987 | Saiki et al. |
| 4,683,195 A | 7/1987 | Mullis et al. |
| 4,683,202 A | 7/1987 | Mullis |
| 4,711,955 A | 12/1987 | Ward et al. |
| 4,820,630 A | 4/1989 | Taub |
| 4,835,263 A | 5/1989 | Nguyen et al. |
| 4,868,103 A | 9/1989 | Stavrianopoulos et al. |
| 4,868,105 A | 9/1989 | Urdea et al. |
| 4,889,818 A | 12/1989 | Gelfand et al. |
| 4,914,210 A | 4/1990 | Levenson et al. |
| 4,954,630 A | 9/1990 | Klein et al. |
| 4,996,143 A | 2/1991 | Heller et al. |
| 5,011,769 A | 4/1991 | Duck et al. |
| 5,108,892 A | 4/1992 | Burke et al. |
| 5,124,246 A | 6/1992 | Urdea et al. |
| 5,188,934 A | 2/1993 | Menchen et al. |
| 5,210,015 A | 5/1993 | Gelfand et al. |
| 5,214,136 A | 5/1993 | Lin et al. |
| 5,272,259 A | 12/1993 | Claussen et al. |
| 5,304,645 A | 4/1994 | Klein et al. |
| 5,312,728 A | 5/1994 | Lizardi et al. |
| 5,326,679 A | 7/1994 | Yanagisawa et al. |
| 5,328,824 A | 7/1994 | Ward et al. |
| 5,451,463 A | 9/1995 | Nelson et al. |
| 5,455,157 A | 10/1995 | Hinzpeter et al. |
| 5,484,908 A | 1/1996 | Froehler et al. |
| 5,487,972 A | 1/1996 | Gelfand et al. |
| 5,492,806 A | 2/1996 | Drmanac et al. |
| 5,494,810 A | 2/1996 | Barany et al. |
| 5,502,177 A | 3/1996 | Matteucci et al. |
| 5,512,667 A | 4/1996 | Reed et al. |
| 5,514,785 A | 5/1996 | Van Ness et al. |
| 5,525,464 A | 6/1996 | Drmanac et al. |

(Continued)

FOREIGN PATENT DOCUMENTS

| | | |
|---|---|---|
| DE | 2546535 | 4/1977 |
| EP | 0070685 | 1/1983 |

(Continued)

OTHER PUBLICATIONS

US 6,255,052, 05/2001, Batz et al. (withdrawn)
Asanuma et al, Angew. Chem. Int. Ed., vol. 43, No. 12, pp. 2671-2673 (2001).*
U.S. Appl. No. 13/776,397.*
Aartsma-Rus et al., "Guidelines for Antisense Oligonucleotide Design and Insight Into Splice-modulating Mechanisms," Molecular Therapy 17(3):548-53 (2009).

(Continued)

*Primary Examiner* — Jane Zara
(74) *Attorney, Agent, or Firm* — McDonnell Boehnen Hulbert & Berghoff LLP

(57) ABSTRACT

The invention pertains to modifications for antisense oligonucleotides, wherein the modifications are used to improve stability and provide protection from nuclease degradation. The modifications could also be incorporated into double-stranded nucleic acids, such as synthetic siRNAs and miRNAs.

12 Claims, 9 Drawing Sheets

(56) References Cited

U.S. PATENT DOCUMENTS

| | | | |
|---|---|---|---|
| 5,538,848 A | 7/1996 | Livak et al. |
| 5,556,752 A | 9/1996 | Lockhart et al. |
| 5,696,251 A | 12/1997 | Arnold et al. |
| 5,801,154 A | 9/1998 | Baracchini et al. |
| 5,801,155 A | 9/1998 | Kutyavin et al. |
| 5,804,375 A | 9/1998 | Gelfand et al. |
| 5,824,796 A | 10/1998 | Petrie et al. |
| 5,830,653 A | 11/1998 | Froehler et al. |
| 5,846,726 A | 12/1998 | Nadeau et al. |
| 5,849,482 A | 12/1998 | Meyer et al. |
| 5,876,930 A | 3/1999 | Livak et al. |
| 5,925,517 A | 7/1999 | Tyagi et al. |
| 5,942,610 A | 8/1999 | Nelson et al. |
| 5,952,202 A | 9/1999 | Aoyagi et al. |
| 6,007,992 A | 12/1999 | Lin et al. |
| 6,028,183 A | 2/2000 | Lin et al. |
| 6,084,102 A | 7/2000 | Kutyavin et al. |
| 6,114,518 A | 9/2000 | Pitner et al. |
| 6,117,973 A | 9/2000 | Batz et al. |
| 6,117,986 A | 9/2000 | Nardone et al. |
| 6,197,944 B1 | 3/2001 | Walder et al. |
| 6,214,979 B1 | 4/2001 | Gelfand et al. |
| 6,312,894 B1 | 11/2001 | Hedgpeth et al. |
| 6,316,610 B2 | 11/2001 | Lee et al. |
| 6,323,337 B1 | 11/2001 | Singer et al. |
| 6,399,392 B1 | 6/2002 | Haugland et al. |
| 6,416,953 B1 | 7/2002 | Heller |
| 6,441,159 B1 | 8/2002 | Lukhtanov et al. |
| 6,448,407 B1 | 9/2002 | Lee et al. |
| 6,451,535 B1 | 9/2002 | Jenne et al. |
| 6,465,175 B2 | 10/2002 | Horn et al. |
| 6,465,644 B1 | 10/2002 | Yan et al. |
| 6,485,901 B1 | 11/2002 | Gildea et al. |
| 6,531,581 B1 | 3/2003 | Nardone et al. |
| 6,531,589 B1 | 3/2003 | Iyer et al. |
| 6,531,591 B1 | 3/2003 | Fensholdt |
| 6,653,473 B2 | 11/2003 | Reed et al. |
| 6,699,975 B2 | 3/2004 | Reed et al. |
| 6,727,356 B1 | 4/2004 | Reed et al. |
| 6,790,945 B2 | 9/2004 | Lukhtanov et al. |
| 6,800,728 B2 | 10/2004 | Schartz |
| 6,825,331 B2 | 11/2004 | Manoharan et al. |
| 6,875,858 B1 | 4/2005 | DeFrancq et al. |
| 7,060,809 B2 | 6/2006 | Wengel et al. |
| 7,122,383 B2 | 10/2006 | Jones et al. |
| 7,173,125 B2 | 2/2007 | Schwartz et al. |
| 7,439,341 B2 | 10/2008 | Laikhter et al. |
| 7,476,735 B2 | 1/2009 | Laikhter et al. |
| 7,605,243 B2 | 10/2009 | Laikhter et al. |
| 7,645,872 B2 | 1/2010 | Laikhter et al. |
| 7,803,536 B2 | 9/2010 | Laikhter et al. |
| 7,803,936 B2 | 9/2010 | Laikhter et al. |
| 2002/0034754 A1 | 3/2002 | Reed et al. |
| 2002/0137070 A1 | 9/2002 | Mirkin et al. |
| 2003/0045488 A1 | 3/2003 | Brown et al. |
| 2003/0082547 A1 | 5/2003 | Ewing et al. |
| 2003/0096254 A1 | 5/2003 | Reed et al. |
| 2003/0144499 A1 | 7/2003 | McGall et al. |
| 2004/0180343 A1 | 9/2004 | Weber |
| 2005/0142598 A1 | 6/2005 | Heindl et al. |
| 2006/0263816 A1 | 11/2006 | Laikhter et al. |
| 2007/0218490 A1 | 9/2007 | Laikhter et al. |
| 2008/0085837 A1 | 4/2008 | Coull et al. |
| 2009/0053821 A1 | 2/2009 | Laikhter et al. |
| 2009/0259030 A1 | 10/2009 | Cook et al. |
| 2010/0298554 A1 | 11/2010 | Laikhter et al. |
| 2011/0060150 A1 | 3/2011 | Laikhter et al. |
| 2011/0236898 A1* | 9/2011 | Rose ............ C07H 21/04 435/6.12 |

FOREIGN PATENT DOCUMENTS

| | | |
|---|---|---|
| EP | 0070686 | 1/1983 |
| EP | 0070687 | 1/1983 |
| EP | 0152886 | 8/1985 |
| EP | 0185494 | 6/1986 |
| EP | 0246864 | 11/1987 |
| EP | 0272007 | 6/1988 |
| EP | 0320308 | 6/1989 |
| EP | 0357011 | 3/1990 |
| EP | 0439182 | 7/1991 |
| EP | 0618925 | 10/1994 |
| GB | 1394368 | 5/1975 |
| GB | 1533121 | 11/1978 |
| JP | 5288681 | 7/1977 |
| JP | 5291031 | 8/1977 |
| JP | 2007509861 | 4/2007 |
| WO | 8909284 | 10/1989 |
| WO | 8910979 | 11/1989 |
| WO | 9014353 | 11/1990 |
| WO | 9105060 | 4/1991 |
| WO | 9210588 | 6/1992 |
| WO | 9617957 | 6/1996 |
| WO | 9628460 | 9/1996 |
| WO | 9634983 | 11/1996 |
| WO | 9640662 | 12/1996 |
| WO | 9729154 | 8/1997 |
| WO | 9739008 | 10/1997 |
| WO | 9914226 | 3/1999 |
| WO | 9937717 | 7/1999 |
| WO | 9940226 | 8/1999 |
| WO | 9951621 | 10/1999 |
| WO | 9951775 | 10/1999 |
| WO | 9964431 | 12/1999 |
| WO | 0006771 | 2/2000 |
| WO | 0070685 | 11/2000 |
| WO | 0104129 | 1/2001 |
| WO | 0142505 | 6/2001 |
| WO | 0186001 | 11/2001 |
| WO | 03019145 | 3/2003 |
| WO | 2004026804 | 4/2004 |
| WO | 2004113562 | 12/2004 |
| WO | 2005049849 | 6/2005 |
| WO | 2005115479 | 12/2005 |
| WO | 2006081035 | 8/2006 |
| WO | 2006127507 | 4/2007 |
| WO | 2010147673 | 12/2010 |
| WO | 2011060014 | 5/2011 |
| WO | 2011120049 | 9/2011 |
| WO | 2011149255 | 12/2011 |
| WO | 2012033848 | 3/2012 |

OTHER PUBLICATIONS

Agrawal et al., "Efficient methods for attaching non-radioactive labels to the 5' ends of synthetic oligodeoxyribonucleotides," Nuc Acids Res. 14:6227-45 (1986).

Ansanuma et al., "Enantioselective incorporation of azobenzenes into oligodeoxyribonucleotide for effective photoregulation of duplex formation," Angew Chem Int Ed. 40(14):2671-3 (2001).

Austermann et al., "Inhibition of human immunodeficiency virus type 1 reverse transcriptase by 3'-blocked oligonucleotide primers," Biochem Pharm. 43(12):2581-9 (1992).

Bailly & Henichart, "DNA recognition by intercalator-minor-groove binder hybrid molecules," Bioconjugate Chem. 2(6):379-93 (1991).

Biéche et al., "Quantitation of hTERT Gene Expression in Sporadic Breast Tumors with a Real-Time Reverse Transcription-Polymerase Chain Reaction Assay," Clin Cancer Res 6(2):452-59 (2000).

Bollum, "Oligodeoxyribonucleotide-primed reactions catalyzed by calf thymus polymerase," J Bio Chem. 237 (6):1945-9 (1962).

Boturyn et al., "Synthesis of Fluorescent probes for the Detection of Abasic Sites in DNA," Tetrahedron 53 (15):5485-92 (1997).

Bustin, "Quantification of mRNA using real-time reverse transcription PCR (RT-PCR):trends and problems," Mol Endocrin. 29:23-9 (2002).

Cardullo et al., "Detection of nucleic acid hybridization by nonradiative fluorescence resonance energy transfer," Proc Natl Acad Sci. USA 85:8790-4 (1988).

Caruthers et al., "Chemical synthesis of deoxyoligonucleotides and deoxyoligonucleotide analogs," Methods Enzymol 211:3-20 (1992).

(56) References Cited

OTHER PUBLICATIONS

Dey & Sheppard, "Ketone-DNA: a versatile postsynthetic DNA decoration platform," Org Lett. 3(25):3983-6 (2001).
Dirks & Tanke, "Advances in fluorescent tracking of nucleic acids in living cells," Biotechniques 40:489-96 (2006).
Dogan et al., "5'-tethered stilbene derivatives as fidelity- and affinity-enhancing modulators of DNA duplex stability," J Am Chem Soc. 126:4762-3 (2004).
Doktycz et al., "Studies of DNA dumbbells. I. Melting curves of 17 DNA dumbbells with different duplex stem sequences linked by T4 endloops: evaluation of the nearest-neighbor stacking interactions in DNA," Biopolymers 32 (7):849-64 (1992).
Easy Q&Q PCR, http://www.eurogentec.be/code/en/product-easy-qq.htm, visited May 9, 2002, 4 pages.
Eder et al., Substrate specificity and kinetics of degradation of antisense oligonucleotides by a 3' exonuclease in plasma, Antisense Res Dev. 1(2):141-51 (1991).
Encyclopedia Britannica (2008) "Nucleic acid," Encyclopedia Britannica Online (Jul. 11, 2008) http://www.search.eb.com/eb/article-256731.
Geary et al., "Pharmacokinetics of phosphorothioate antisense oligodeoxynucleotides," Curr Opin Investig Drugs. 2 (4):562-73 (2001).
Gelfand, "Taq DNA Polymerase," PCR Technology Principles and Applications for DNA Amplification, Stockton Press, NY, Ehrlich ed. Ch. 2, 17-22 (1989).
Genbank Accession No. AF298116, Rose et al., "Mus musculus bHLH protein Ptfl-p48 gene," (2001) 6 pages.
Gibson et al., "Molecular modelling of anthraquinone-oligodeoxynucleotide conjugates," Pharm Sci. 2:545-8 (1996).
Goemans et al., "Systemic Administration of PRO051 in Duchenne's Muscular Dystrophy," N Engl J Med 364 (16):1513-22 (2011).
Gorelick et al., "Effect of benzannelation on the coloration of p-aminoazo compounds," Zhurnal Organicheskoi Khimii (1980) 16(9):1927-33—Abstract only—Accession No. 1981:193676.
Heesemann, "Studies on monolayers. 1. Surface tension and absorption spectroscopic measurements of monolayers of surface-active azo and stilbene dyes," J Am Chem Soc. 102(7):2167-76 (1980).
Heller & Morrison, "Chemiluminescent and fluorescent probes for DNA hybridization systems," Rapid Detection and Identification of Infectious Agents (1985) Academic Press, Inc., Orlando, Kingsbury et al. eds. 245-56.
Ho & Natansohn, "Azo polymers for reversible optical storage. 7. The effect of the size of the photochromic groups," Macromolecules 28(18):6124-67 (1995) (Abstract only—Accession No. 1995:746851).
Hugentobler et al., "Compounds with a metal-arene sigma-bond. Part 2. Cyclometalation of arylazo compounds. Part 2. Regioselectivity of the cyclopalladation of some substituted 1-arylazonaphthalenes," Helvetica Chimica Acta 65 (4):1202-11 (1982) (Abstract only—Accession No. 1982:616430).
Ito et al., "Reductive Electron Injection into Duplex DNA by Aromatic Amines," J Am Chem Soc. 126: 15552-9 (2004).
Iyer et al., "3H-1,2-benzodithiole-3-one 1,1-dioxide as an improved sulfurizing reagent in the solid-phase synthesis of oligodeoxyribonucleoside phosphorothioates," J Am Chem Soc. 112:1253-4 (1982).
Jenkins, Senior Librarian at the United States Patent and Trademark Office, email dated Mar. 18, 2010 and previously related email corespondence, pp. 1-2.
Jepsen and Wengel, "LNA-antisense rivals siRNA for gene silencing," Curr Opin Drug Discov Devel 7(2):188-94 (2004).
Mao et al. "Oligonucleotides with strongly fluorescent groups pi-conjugated to a nucleobase: syntheses, melting temperatures, and conformation," Bioorg Med Chem Lett. 13(16):2785-8 (2003).
Ju et al., "Fluorescence energy transfer dye-labeled primers for DNA sequencing and analysis," Proc Natl Acad Sci USA 92:4347-51 (1995).

Kerzhner et al., "Photoisomerization of aromatic azo compounds adsorbed on a hydroxylated surface," Zhurnal Obshchei Khimii 53(10):2303-2306 (1983) (Abstract only—Accession No. 1984:50840).
Krützfeldt et al., "Specificity, duplex degradation and subcellular localization of antagomirs," Nucleic Acids Res. 35 (9):2885-92 (2007).
Kuball et al., "Helical twisting power of chiral mono- and bis-aminoanthraquinones," J Mater Chem. 5(12):2167-74 (1995).
Kurreck, "Antisense technologies. Improvement through novel chemical modifications," Eur J Biochem. 270 (8):1628-44 (2003).
Lawyer et al., "Isolation, characterization, and expression in *Escherichia coli* of the DNA polymerase gene from Thermus aquaticus," J Biol Chem. 264(11):6427-37 (1989).
Lehman & Chen, "Persistence of deoxyribonucleic acid polymerase I and its 5' --> 3' exonuclease activity in PoIA mutants of *Escherichia coli* K12," J. Biol. Chem. (1973) 248(22):7717-7723.
Lennox & Behlke, "A direct comparison of anti-microRNA oligonucleotide potency", Pharm Res. 27(9):1788-99 (2010).
Lewis et al., "Hybrid oligonucleotides containing stilbene units, Excimer fluorescence and photodimerization," J Am Chem Soc. 117:8785-92 (1995).
Liang et al., "An interstrand-wedged duplex composed of alternating DNA base pairs and covalently attached intercalators," Journal of Materials Chemistry 20(3):575-81 (2010).
MacKay, "Real-time PCR in the microbiology laboratory," Clin Microbiol Infec. 10:190-212 (2004).
Marshall, "Rules for the visible absorption spectra of halogenated fluorescein dyes," Histochemical J. 7:299-303 (1975).
Matthews & Kricka, "Analytical strategies for the use of DNA probes," Anal Biochem.169:1-25 (1988).
May et al., "A new dark quencher for use in genetic analysis," Chem. Commun 970-1 (2003).
May et al., "A novel dark quencher for oligonucleotide probes: synthesis and applications," poster presentation from Tides 2002 IBC Oligonucleotide and Peptide Technology Conference, May 6-8, 2002, Las Vegas, Nevada (2 pages).
May et al., "Synthesis of a novel dark quencher for use with long wavelength dyes in oligonucleotide probes," Innovation and Perspectives in Solid Phase Synthesis & Combinatorial Libraries: Peptides, Proteins and Nucleic Acids Small Molecule Organic Chemical Diversity, Collected Papers, 7th International Symposium, Southampton, United Kingdom, Sep. 18-22, 2002, 231-233.
Mineno et al., "Fluorescent labeling of a DNA sequencing primer," DNA Seq. 4(3):135-41 (1993).
Misiura et al., "Biotinyl and phosphotyrosinyl phosphoramidite derivatives useful in the incorporation of multiple reporter groups on synthetic oligonucleotides," Nucleic Acids Research 18(15):4345-54 (1990).
Mitrpant et al., "Rational Design of Antisense Oligomers to Induce Dystrophin Exon Skipping," Molecular Therapy 17(8):1418-26 (2009).
Miyashita et al., "Novel dinucleoside phosphotriester unit conjugated with an intercalative moiety in a stereospecific manner enhances thermal stability of an alternate-stranded triple helix," Tetrahedron Letters 44:7399-402 (2003).
Mori et al., "Oligodeoxynucleotide analogs with 5'-linked anthraquinone," FEBS Letters 249(2):213-8 (1989).
Morier-Teissier et al., "Free radical production and DNA cleavage by copper chelating peptide-anthraquinones," Anti-Cancer Drug Design 5:291-305 (1990).
Morrison et al., "Solution-phase detection of polynucleotides using interacting fluorescent labels and competitive hybridization," Anal Biochem. 183:231-44 (1989).
Mullis et al., "Specific Enzymatic Amplification of DNA In Vitro: The Polymerase Chain Reaction," Cold Spring Harbor Symp. Quant. Biol. 51:263-73 (1986).
Muntoni & Wood, "Targeting RNA to treat neuromuscular disease," Nat Rev Drug Discov 10(8):621-37 (2011).
Narayanan et al., "Clamping down on weak terminal base pairs: oligonucleotides with molecular caps as fidelity-enhancing elements at the 5'- and 3'-terminal residues," Nucl Acids Res. 32:2901-11 (2004).

(56) References Cited

OTHER PUBLICATIONS

Noble et al, "Methylphosphonates as probes of protein-nucleic acid interactions," Nuc Acids Res.12(7):3387-404 (1984).
Ossipov et al., "Dipyrido[3,2-a:2',3'-c]phenazine-Tethered Oligo-DNA: Synthesis and Thermal Stability of Their DNA•DNA and DNA•RNA Duplexes and DNA•DNA•DNA Triplexes," Helvetica Chimica Acta 82(12):2186-2200 (1999).
Owczarzy et al., "Predicting Sequence-Dependent Melting Stability of Short Duplex DNA Oligomers," Biopolymers 44(3):217-39 (1998).
Owczarzy et al., "Predicting stability of DNA duplexes in solutions containing magnesium and monovalent cations," Biochem. 47:5336-53 (2008).
Owczarzy, "Melting temperatures of nucleic acids: discrepancies in analysis," Biophys Chem. 117(3):207-15 (2005).
Patra & Richert, "High fidelity base pairing at the 3'-terminus," J Am Chem Soc. 131(35):12671-81 (2009).
Peek & Behlke, "Design of active small interfering RNAs," Curr Opin Mol Ther. 9(2):110-18 (2007).
Petersheim & Turner. "Base-stacking and base-pairing contributions to helix stability: thermodynamics of double-helix formation with CCGG, CCGGp, CCGGAp, ACCGGp, CCGGUp, and ACCG-GUp," Biochem. 22:256-63 (1983).
PR Newswire, Announcing IBC's Tides 2002: Oligonucleotide and Peptide Technology Conferences May 6-8, 2002, Las Vegas, NV, Copyright 2002, PR Newswire Association LLC, pp. 1-2, website (retrieved Mar. 18, 2010): http://www.thefreelibrary.com/-/print/PrintArticle.aspx?id=82059345.
Proudnikov & Mirzabekov, "Chemical methods of DNA and RNA fluorescent labeling," Nucleic Acids Res. 24 (22):4535-42 (1996).
Prokhorenko et al., "Incorporation of a pyrene nucleoside analogue into synthetic oligodeoxynucleotides using a nucleoside-like synthon," Bioorganic & Medicinal Chemistry Letters 5(18):2081-4 (1995).
Puskas et al., "Diamino-Anthraquinone: A New Intercalating Agent. Synthesis and Linking to Oligodeoxynucleotide," Nucleosides & Nucleotides 14(3-5):967-8 (1995).
Rose et al., "The Role of PTF1-P48 in pancreatic acinar gene expression," J Biol Chem. 276(47):44018-26 (2001).
Rychlik et al., "Optimization of the annealing temperature for DNA amplification in vitro," Nucl Acids Res. 18:6409-12 (1990).
Santalucia, "A unified view of polymer, dumbbell, and oligonucleotide DNA nearest-neighbor thermodyamics," Proc Natl Acad Sci USA 95:1460-5 (1998).
Schnippering et al., "Synthesis and electrochemical properties of TTF modified oligodeoxynucleotides," Chemical Communications 37:5552-4 (2009).
Schuster, "Long-range charge transfer in DNA: transient structural distortions control the distance dependence," Acc Chem Res. 33:253-60 (2000).
Setlow et al., "Deoxyribonucleic acid polymerase: two distinct enzymes in one polypeptide," J Biol Chem. 247 (1):224-31 (1972).
Shi et al., "Design of phosphoramidite monomer for optimal incorporation of functional intercalator to main chain of oligonucleotide," Bioconjug Chem. 16(2):306-11 (2005).
Sijm et al., "Aqueous solubility, octanol solubility, and octanol/water partition coefficient of nine hydrophobic dyes," Envir. Toxic. Chem. 18(6):1109-17 (1999).
Stein et al., "Physicochemical properties of phosphorothioate oligodeoxynucleotides," Nucleic Acids Res. 16 (8):3209-21 (1988).
Straarup et al., "Short locked nucleic acid antisense oligonucleotides potently reduce apolipoprotein B mRNA and serum cholesterol in mice and non-human primates," Nucleic Acids Research 38(20):7100-11 (2010).
Swayze et al., "Antisense oligonucleotides containing locked nucleic acid improve potency but cause significant hepatotoxicity in animals," Nucleic Acids Res. 35(2):687-700 (2007).
Tu & Cohen, "3'-end labeling of DNA with [alpha-32P]cordycepin-5'-triphosphate," Gene 10:177-83 (1980).
Wang et al., "Synthesis of Thermostable Azo-type Photoswitches towards Photoregulating Nucleic Acid Structures," Chinese Journal of Chemistry 27(8):1582-8 (2009).
Wetmer, "DNA probes: applications of the principles of nucleic acid hybridization," Critical Review in Biochem and Mol Biol. 26(314):227-59 (1991).
Zielske, "(Toxyloxy)anthraquinones: versatile synthons for the preparation of various aminoanthraquinones," J Org Chem. 52:1305-9 (1987).
7th International Symposium, pp. 1-14, 7th International Symposium & Exhibition Solid Phase Synthesis & Combinatorial Chemical Libraries, Sep. 18-22, 2001—University of Southampton, England, UK.
International Search Report from International Application No. PCT/US2011/050710, mailed Dec. 12, 2011.
Written Opinion of the International Searching Authority from International Application No. PCT/US2011/050710, mailed Mar. 12, 2013.
International Preliminary Report on Patentability from International Application No. PCT/US2011/050710 mailed Mar. 12, 2013.
International Search Report from International Application No. PCT/US2011/30215, mailed May 23, 2011.
Written Opinion of the International Searching Authority from International Application No. PCT/US2011/030215, mailed May 23, 2011.
International Preliminary Report on Patentability from International Application No. PCT/US2011/030215, mailed Oct. 2, 2012.
European Patent Office Action for Application No. 11760380.3 dated Aug. 20, 2013.
European Patent Office Action for Application No. 11760380.3 dated Apr. 14, 2014.
Australian Patent Office Patent Examination Report No. 1 for Application No. 2011230496 dated Jun. 16, 2014.
Australian Patent Office Patent Examination Report No. 1 for Application No. 2013202227 dated May 28, 2014.
International Search Report from International Application No. PCT/US2014/018015, mailed Jun. 3, 2014.
Written Opinion of the International Searching Authority from International Application No. PCT/US2014/018015, mailed Jun. 3, 2014.
Australian Patent Office Examination Report No. 1 for Application No. 2013203590, dated Nov. 27, 2014, 4 pages.
Australian Patent Office Examination Report No. 1 for Application No. 2011299233, dated Nov. 28, 2014, 7 pages.
Notification of Reasons for Refusal of Japanese Patent Application No. 2013-528272, dated Sep. 8, 2015, 6 pages (Translation).
Dobosy et al., "RNase H-dependent PCT (rhPCR): improved specificity and single nucleotide polymorphism detection using blocked cleavable primers," BMC Biotechnology 11:80 (2011).
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Molecular BioSystems 5 (8):838-43 (2009).
Tesler et al., "Synthesis and characterization of DNA oligomers and duplexes containing covalently attached molecular labels: comparison of biotin, fluorescein, and pyrene labels by thermodynamic and optical spectroscopic measurements," J Am Chem Soc. 111:6966-7 (1989).
Tu & Cohen, "3'-end labeling of DNA with [alpha-32P]cordycepin-5'-triphosphate," Gene 10:177-83 (1980).
Wang et al., "Synthesis of Thermostable Azo-type Photoswitches towards Photoregulating Nucleic Acid Structure," Chinese Journal of Chemistry 27(8):1582-8 (2009).
Warshaw & Tinoco, "Optical properties of sixteen dinucleoside phosphates," J Mol Biol. 20(1):29-38 (1966).
Wetmer, "DNA probes: applications of the principles of nucleic acid hybridization," Critical Review in Biochem and Mol Biol. 26(3/4):227-59 (1991).
Zielske, "(Toxyioxy)anthraquinones: versatile synthons for the preperation of various aminoanthraquinones," J Org Chem. 52:1305-9 (1987).

(56) References Cited

OTHER PUBLICATIONS

7th International Symposium. pp, 1-14, 7th International Symposium & Exhibition Solid Phase Synthesis & Combinatorial Chemical Libraries, Sep. 18-22, 2001-University of Southampton, England, UK.

International Search Report from international Application No. PGT/US2011/050710, mailed Dec. 12, 2011.

Written Opinion of the International Searching Authority from International Application No. PCT/US2011/050710, mailed Dec. 12, 2011.

International Preliminary Report on Patentability from International Application No. PCT/US2011/050710 mailed Dec. 12, 2011.

International Search Report from International Application No. PCT/US2011/302015, mailed May 23, 2011.

\* cited by examiner

MODIFICATIONS FOR ANTISENSE COMPOUNDS

CROSS REFERENCE TO RELATED APPLICATION

This application is a continuation of U.S. application Ser. No. 13/227,286, filed Sep. 7, 2011 which claims the benefit of priority from U.S. Provisional Application No. 61/380,586, filed Sep. 7, 2010. This application is also a continuation-in-part of U.S. application Ser. No. 13/073,866, filed Mar. 28, 2011, which claims the benefit of priority from U.S. Provisional Application No. 61/318,043, filed Mar. 26, 2010. The disclosures of all four above applications are explicitly incorporated by reference herein in their entirety.

STATEMENT REGARDING FEDERALLY-SPONSORED RESEARCH OR DEVELOPMENT

This invention was made with government support under Small Business Innovation Research (SBIR) Grant No. GM085863 awarded by the National Institute of General Medical Sciences of the National Institutes of Health (NIH). The government has certain rights in the invention.

FIELD OF THE INVENTION

This invention pertains to modifications for antisense oligonucleotides, wherein the modifications are used to improve stability and provide protection from nuclease degradation.

BACKGROUND OF THE INVENTION

Antisense oligonucleotides (ASOs) are synthetic nucleic acids that bind to a complementary target and suppress function of that target. Typically ASOs are used to reduce or alter expression of RNA targets, particularly messenger RNA (mRNA) or microRNA (miRNA) species. As a general principle, ASOs can suppress gene expression via two different mechanisms of action, including: 1) by steric blocking, wherein the ASO tightly binds the target nucleic acid and inactivates that species, preventing its participation in cellular biology, or 2) by triggering degradation, wherein the ASO binds the target and leads to activation of a cellular nuclease that degrades the targeted nucleic acid species. One class of "target degrading" ASOs are "RNase H active"; formation of heteroduplex nucleic acids by hybridization of the target RNA with a DNA-containing "RNase H active" ASO forms a substrate for the enzyme RNase H. RNase H degrades the RNA portion of the heteroduplex molecule, thereby reducing expression of that species. Degradation of the target RNA releases the ASO, which is not degraded, which is then free to recycle and can bind another RNA target of the same sequence. For an overview of antisense strategies, oligonucleotide design, and chemical modifications, see Kurreck, 2003, *Eur. J. Biochem.*, 270(8): 1628-44.

Unmodified DNA oligonucleotides have a half-life of minutes when incubated in human serum. Therefore, unmodified DNA oligonucleotides have limited utility as ASOs. The primary nuclease present in serum has a 3'-exonuclease activity (Eder et al., 1991, *Antisense Res. Dev.* 1(2): 141-51). Once an ASO gains access to the intracellular compartment, it is susceptible to endonuclease degradation. Historically, the first functional ASOs to gain widespread use comprised DNA modified with phosphorothioate groups (PS). PS modification of the internucleotide linkages confers nuclease resistance, making the ASOs more stable both in serum and in cells. As an added benefit, the PS modification also increases binding of the ASO to serum proteins, such as albumin, which decreases the rate of renal excretion following intravenous injection, thereby improving pharmacokinetics and improving functional performance (Geary et al., 2001, *Curr. Opin. Investig. Drugs*, 2(4): 562-73). However, PS-modified ASOs are limited to a 1-3 day half-life in tissue, and the PS modifications reduce the binding affinity of the ASO for the target RNA, which can decrease potency (Stein et al., 1988, *Nucleic Acids Res.* 16(8): 3209-21).

The PS modification is unique in that it confers nuclease stability yet still permits formation of a heteroduplex with RNA that is a substrate for RNase H action. Most other modifications that confer nuclease resistance, such as methyl phosphonates or phosphoramidates, are modifications that do not form heteroduplexes that are RNase H substrates when hybridized to a target mRNA. Improved potency could be obtained using compounds that were both nuclease resistant and showed higher affinity to the target RNA yet retain the ability to activate RNase H mediated degradation pathways.

Further design improvements were implemented to increase affinity for the target RNA while still maintaining nuclease resistance (see Walder et al., U.S. Pat. No. 6,197,944 for designs containing 3'-modifications with a region containing unmodified residues with phosphodiester linkages; see also European Patent No. 0618925 for "Gapmer" compounds having 2'-methoxyethylriboses (MOE's) providing 2'-modified 'wings' at the 3' and 5' ends flanking a central 2'-deoxy gap region). The new strategy allows for chimeric molecules that have distinct functional domains. For example, a single ASO can contain a domain that confers both increased nuclease stability and increased binding affinity but itself does not form an RNase H active substrate; a second domain in the same ASO can be RNase H activating. Having both functional domains in a single molecule improves performance and functional potency in antisense applications. One successful strategy is to build the ASO from different chemical groups with a domain on each end intended to confer increased binding affinity and increased nuclease resistance that flank a central domain comprising different modifications which provides for RNase H activation. This so-called "end blocked" or "gapmer" design is the basis for the improved function "second generation" ASOs. Compounds of this design are typically significantly more potent as gene knockdown agents than the "first generation" PS-DNA ASOs.

Typically ASOs that function using steric blocking mechanisms of action show higher potency when made to maximize binding affinity. This can be accomplished using chemical modifications that increase binding affinity, such as many of the 2'-ribose modifications discussed herein, minor groove binders, or the internal non-base modifiers of the present invention. Alternatively, increased binding affinity can be achieved by using longer sequences. However, some targets are short, such as miRNAs, which are typically only 20-24 bases long. In this case, making ASOs longer to increase binding affinity is not possible. Further, short synthetic oligonucleotides gain access into cells more efficiently than long oligonucleotides, making it desirable to employ short sequences with modifications that increase binding affinity (see, e.g., Straarup et al., 2010, *Nucleic Acids Res.* 38(20): 7100-11). The chemical modification and methods of the present invention enable synthesis of relatively short ASOs having increased binding affinity that show improved functional performance.

ASO modifications that improve both binding affinity and nuclease resistance typically are modified nucleosides that are costly to manufacture. Examples of modified nucleosides include locked nucleic acids (LNA), wherein a methyl bridge connects the 2'-oxygen and the 4'-carbon, locking the ribose in an A-form conformation; variations of LNA are also available, such as ethylene-bridged nucleic acids (ENA) that contain an additional methyl group, amino-LNA and thio-LNA. Additionally, other 2'-modifications, such as 2'-O-methoxyethyl (MOE) or 2'-fluoro (2'-F), can also be incorporated into ASOs. Some modifications decrease stability, and some can have negative effects such as toxicity (see Swayze et al., 2007, *Nucleic Acids Res.* 35(2): 687-700).

The present invention provides for non-nucleotide modifying groups that can be inserted between bases in an ASO to improve nuclease resistance and binding affinity, thereby increasing potency. The novel modifications of the present invention can be employed with previously described chemical modifications (such as PS internucleotide linkages, LNA bases, MOE bases, etc.) and with naturally occurring nucleic acid building blocks, such as DNA or 2'-O-Methyl RNA (2'OMe), which are inexpensive and non-toxic. These and other advantages of the invention, as well as additional inventive features, will be apparent from the description of the invention provided herein.

BRIEF SUMMARY OF THE INVENTION

The invention provides non-nucleotide modifications for antisense oligonucleotides, wherein the modifications are used to increase binding affinity and provide protection from nuclease degradation.

The invention also provides an antisense oligonucleotide comprising at least one modification that is incorporated between two bases of the antisense oligonucleotide, wherein the modification increases binding affinity and nuclease resistance of the antisense oligonucleotide. In one embodiment, the antisense oligonucleotide comprises at least one modification that is located within three bases of a terminal nucleotide. In another embodiment, the antisense oligonucleotide comprises at least one modification that is located between a terminal base and a penultimate base of either the 3'- or the 5'-end of the oligonucleotide. In a further embodiment, the antisense oligonucleotide comprises a modification between the terminal base and the penultimate base of both the 3'- and the 5'-ends of the antisense oligonucleotide.

The invention further provides an antisense oligonucleotide comprising at least one modification that is incorporated between two bases of the antisense oligonucleotide, wherein the modification increases binding affinity and nuclease resistance of the antisense oligonucleotide, and wherein the modification is a napthylene-azo compound.

The invention further provides an antisense oligonucleotide comprising at least one modification that is incorporated between two bases of the antisense oligonucleotide, wherein the modification increases binding affinity and nuclease resistance of the antisense oligonucleotide, and wherein the modification has the structure:

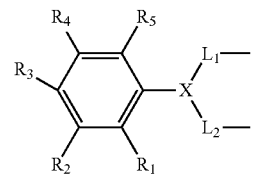

Formula 1 wherein the linking groups $L_1$ and $L_2$ positioning the modification at an internal position of the oligonucleotide are independently an alkyl, alkynyl, alkenyl, heteroalkyl, substituted alkyl, aryl, heteroaryl, substituted aryl, cycloalkyl, alkylaryl, or alkoxy groups; $R_1$-$R_5$ are independently a hydrogen, alkyl, alkynyl, alkenyl, heteroalkyl, substituted alkyl, aryl, heteroaryl, substituted aryl, cycloalkyl, alkylaryl, alkoxy, an electron withdrawing group, an electron donating group, or an attachment point for a ligand; and X is a nitrogen or carbon atom, wherein if X is a carbon atom, the fourth substituent attached to the carbon atom can be hydrogen or a C1-C8 alkyl group.

The invention further provides an antisense oligonucleotide comprising at least one modification that is incorporated between two bases of the antisense oligonucleotide, wherein the modification increases binding affinity and nuclease resistance of the antisense oligonucleotide, and wherein the modification has the structure:

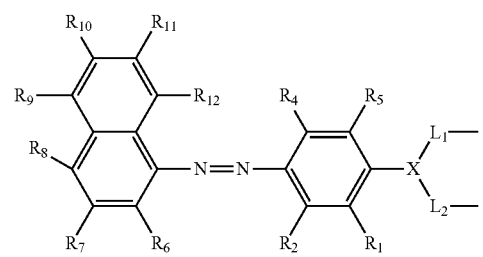

Formula 2 wherein the linking groups $L_1$ and $L_2$ positioning the modification at an internal position of the oligonucleotide are independently an alkyl, alkynyl, alkenyl, heteroalkyl, substituted alkyl, aryl, heteroaryl, substituted aryl, cycloalkyl, alkylaryl, or alkoxy groups; $R_1$, $R_2$, $R_4$, $R_5$ are independently a hydrogen, alkyl, alkynyl, alkenyl, heteroalkyl, substituted alkyl, aryl, heteroaryl, substituted aryl, cycloalkyl, alkylaryl, alkoxy, an electron withdrawing group, or an electron donating group; $R_6$, $R_7$, $R_9$-$R_{12}$ are independently a hydrogen, alkyl, alkynyl, alkenyl, heteroalkyl, substituted alkyl, aryl, heteroaryl, substituted aryl, cycloalkyl, alkylaryl, alkoxy, an electron withdrawing group, or an electron donating group; $R_8$ is a hydrogen, alkyl, alkynyl, alkenyl, heteroalkyl, substituted alkyl, aryl, heteroaryl, substituted aryl, cycloalkyl, alkylaryl, alkoxy, or an electron withdrawing group; and X is a nitrogen or carbon atom, wherein if X is a carbon atom, the fourth substituent attached to the carbon atom can be hydrogen or a C1-C8 alkyl group. In one embodiment, $R_8$ is $NO_2$.

The invention further provides an antisense oligonucleotide comprising at least one modification that is incorporated between two bases of the antisense oligonucleotide, wherein the modification increases binding affinity and nuclease resistance of the antisense oligonucleotide, and wherein the modification has the structure:

Formula 3

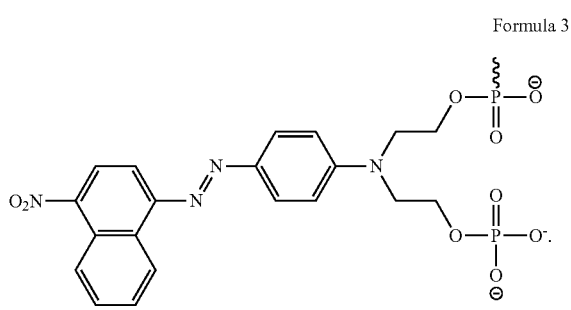

The antisense oligonucleotides of the invention can include natural, non-natural, or modified bases known in the art. The antisense oligonucleotides of the invention can also include, typically but not necessarily on the 3' or 5' ends of the oligonucleotide, additional modifications such as minor groove binders, spacers, labels, or other non-base entities. In one embodiment, the antisense oligonucleotide further comprises 2'-O-methyl RNA, and optionally comprises at least one napthylene-azo compound. In another embodiment, the antisense oligonucleotide further comprises phosphorothioate linkages. In a further embodiment, the antisense oligonucleotide comprises a region of bases linked through phosphodiester bonds, wherein the region is flanked at one or both ends by regions containing phosphorothioate linkages.

The invention further provides an antisense oligonucleotide having the structure:

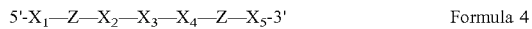

5'-$X_1$—Z—$X_2$—$X_3$—$X_4$—Z—$X_5$-3'    Formula 4 wherein $X_1$ and $X_5$ are independently 1-3 nucleotides wherein the internucleotide linkages are optionally phosphorothioate; Z is a napthylene-azo compound; $X_2$ and $X_4$ are independently 1-5 nucleotides wherein the internucleotide linkages are optionally phosphorothioate; and $X_3$ is 10-25 nucleotides.

In one embodiment, a third modification can be inserted around the middle of the antisense oligonucleotide. For longer nucleotides (greater than 25 bases), additional modifications could be used at intervals to confer greater stability.

In the modifications of the invention, a modifying group is inserted between adjacent bases, thereby generating an ASO with reduced toxicity and improved affinity and stability. The bases can be DNA, 2'OMe RNA, or other modified bases. However, modified bases do not need to be employed. Because the modifications are inserted between the bases, they can be added as a phosphoramidite compound using standard phosphoramidite synthesis chemistry.

DETAILED DESCRIPTION OF THE INVENTION

Figure 1:
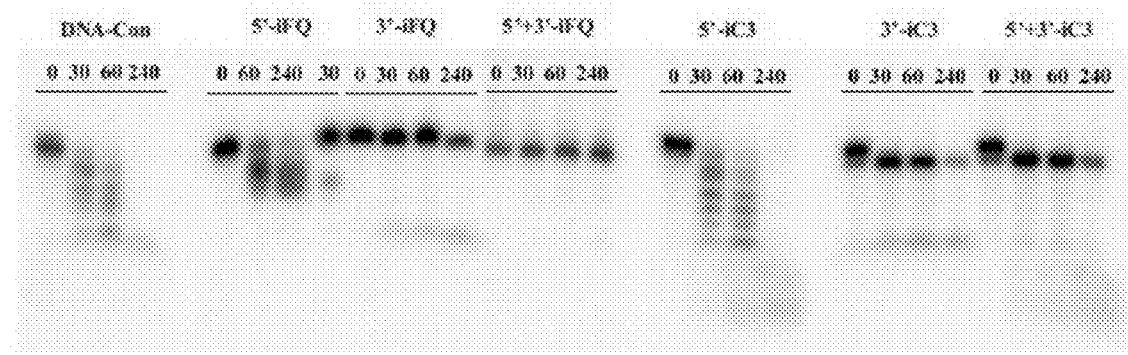
FIG. 1 is a gel photograph that illustrates the levels of degradation of synthetic DNA oligomers in fetal bovine serum. A series of 10-mer single-stranded DNA oligonucleotides were trace labeled with $^{32}P$ at their 5'-ends and were incubated in serum at 37° C. for the indicated times (0-240 minutes). Reaction products were separated by polyacrylamide gel electrophoresis (PAGE) and visualized by phosphorimaging. Samples are identified in Table 4.

The antisense oligonucleotides of the invention have modifications placed between nucleotides, wherein the modifications increase affinity to the complementary target and provide nuclease resistance. In one embodiment of the invention, the compounds are the same as those described in U.S. application Ser. No. 13/073,866, the disclosure of which is incorporated by reference herein in its entirety.

In another embodiment of the invention, the antisense oligonucleotide comprises at least one modification that has the structure:

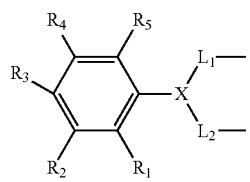

Formula 1 wherein the linking groups $L_1$ and $L_2$ positioning the modification at an internal position of the oligonucleotide are independently an alkyl, alkynyl, alkenyl, heteroalkyl, substituted alkyl, aryl, heteroaryl, substituted aryl, cycloalkyl, alkylaryl, or alkoxy groups; $R_1$-$R_5$ are independently a hydrogen, alkyl, alkynyl, alkenyl, heteroalkyl, substituted alkyl, aryl, heteroaryl, substituted aryl, cycloalkyl, alkylaryl, alkoxy, an electron withdrawing group, an electron donating group, or an attachment point for a ligand; and X is a nitrogen or carbon atom, wherein if X is a carbon atom, the fourth substituent attached to the carbon atom can be hydrogen or a C1-C8 alkyl group. In a further embodiment of the invention, the antisense oligonucleotide comprises at least one modification that has the structure:

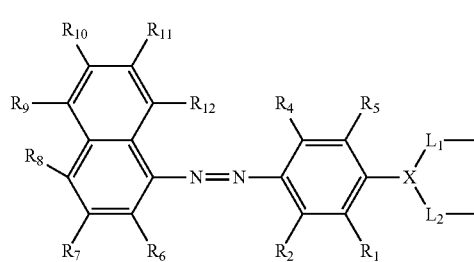

Formula 2 wherein the linking groups $L_1$ and $L_2$ positioning the modification at an internal position of the oligonucleotide are independently an alkyl, alkynyl, alkenyl, heteroalkyl, substituted alkyl, aryl, heteroaryl, substituted aryl, cycloalkyl, alkylaryl, or alkoxy groups; $R_1$, $R_2$, $R_4$, $R_5$ are independently a hydrogen, alkyl, alkynyl, alkenyl, heteroalkyl, substituted alkyl, aryl, heteroaryl, substituted aryl, cycloalkyl, alkylaryl, alkoxy, an electron withdrawing group, or an electron donating group; $R_6$, $R_7$, $R_9$-$R_{12}$ are independently a hydrogen, alkyl, alkynyl, alkenyl, heteroalkyl, substituted alkyl, aryl, heteroaryl, substituted aryl, cycloalkyl, alkylaryl, alkoxy, an electron withdrawing group, or an electron donating group; $R_8$ is a hydrogen, alkyl, alkynyl, alkenyl, heteroalkyl, substituted alkyl, aryl, heteroaryl, substituted aryl, cycloalkyl, alkylaryl, alkoxy, or an electron withdrawing group; and X is a nitrogen or carbon atom, wherein if X is a carbon atom, the fourth substituent attached to the carbon atom can be hydrogen or a C1-C8 alkyl group.

The compositions and methods of the invention involve modification of an oligonucleotide by placing non-base modifying group(s) as insertions between bases while retaining the ability of that sequence to hybridize to a complementary sequence. Typically, insertion of non-base modifying groups between bases results in a significant loss of affinity of the modified sequence to its complement. The unique compositions of the invention increase affinity of the modified sequence to its complement, increasing stability and increasing $T_m$. Placement of such non-base modifying group(s) between bases prevents nucleases from initiating degradation at the modified linkage(s). When placed between the first and second bases at both ends of the oligonucleotide, the sequence is protected from attack by both 5'-exonucleases and 3'-exonucleases. Placement at central position(s) within the sequence can additionally confer some resistance to endonucleases. In particular, compounds of the class of Formula 2 above impede nuclease attack for several flanking internucleotide phosphate bonds adjacent to the modified linkage, creating a protected "zone" where unmodified linkages are less susceptible to nuclease cleavage. The modifications also prevent nucleases from cleaving terminal bases. Thus the compositions and methods of the invention permit synthesis of ASOs having increased $T_m$ and increased nuclease resistance yet do not employ modified but instead employ a non-base modifying group inserted between residues.

The ability of the modifying groups of the present invention to increase binding affinity ($T_m$) of duplexed nucleic acids is demonstrated in Example 1, where melting studies were conducted for a series of unmodified and modified 10-mer duplex DNA oligomers. Using compositions and methods of the present invention, an increase of +11° C. was achieved using only two modifying groups (between the two terminal bases on each end of the oligomer). Similar duplexes made with insertions of a propanediol group show significant destabilization, consistent with the expected results for non-base insertions.

The ability of the modifying groups of the present invention to improve nuclease stability is demonstrated in Example 2, where single-stranded DNA oligomers were incubated in serum (subjected to degradation by serum nucleases) and then examined for integrity by polyacrylamide gel electrophoresis (PAGE). Unmodified DNA oligomers are rapidly degraded in serum whereas a 10-mer DNA oligonucleotide with an insertion of the napthylene-azo modifier between the terminal bases on each end resulted in a compound that was not degraded after 4 hours incubation. Other modifying groups, such as a propanediol spacer, only slowed the rate of degradation slightly. $T_m$-enhancing, nuclease blocking modifications (such as the napthylene-azo group) can be inserted into single-stranded oligomers to improve properties. Stabilized, increased binding affinity oligomers of this type can have a variety of uses, as is well appreciated by those with skill in the art. As examples (not meant to be limiting), such oligomers can be used as ASOs to promote reduction of mRNA or miRNA levels in a cell or animal. Such examples are demonstrated in Examples 3 and 4 below.

In a further embodiment of the invention, the modifications could also be incorporated into double-stranded nucleic acids, such as synthetic siRNAs and miRNAs. Careful placement of the modifying group should lead to improvements in nuclease stability and could alter local thermal stability, which if employed asymmetrically in an RNA duplex, is well known to influence strand loading into RISC (Peek and Behlke, 2007, *Curr. Opin. Mol. Ther.* 9(2): 110-18), and therefore impact relative biological potency of the compound as a synthetic trigger of RNAi.

Oligonucleotides antisense in orientation to miRNAs will bind the miRNA and functionally remove that species from participation in the microRNA-Induced Silencing Complex (miRISC) (Krutzfeldt et al., 2007, *Nucleic Acids Res.* 35(9): 2885-92). Such anti-miRNA oligonucleotides (AMOs) are thought to function by a steric binding mechanism, and compounds with high stability and high affinity generally show improved functional performance compared with low affinity compounds (Lennox and Behlke, 2010, *Pharm. Res.* 27(9): 1788-99). The ASOs of the present invention can function as anti-miRNA oligonucleotides.

In the modifications of the present invention, a modifying group is inserted between adjacent bases, thereby generating an ASO with reduced toxicity and improved binding affinity and nuclease stability. The bases can be DNA, 2'OMe RNA, LNA, or other modified bases. However, modified bases do not need to be employed. Because the modifications are inserted between the bases, they can be added as a phosphoramidite compound using standard phosphoramidite synthesis chemistry.

In yet another application where ASOs are employed to alter or modify gene expression, the ASOs are designed to be complementary to a pre-mRNA species at sites at or near an intron/exon splice junction. Binding of the ASO at or near splice sites can alter processing at this intron/exon junction by the nuclear splicing machinery thereby changing splice patterns present in the final mature in RNA (i.e., can be used to alter the exons that are included or excluded in the final processed mRNA). Following mRNA maturation, the altered mRNA will direct synthesis of an altered protein species as a result of this ASO treatment. Methods to design splice-blocking oligonucleotides (SBOs) are well known to those with skill in the art (see, e.g., Aartsma-Rus et al., 2009, *Mol. Ther.* 17(3): 548-53; and Mitrpant et al., 2009, *Mol. Ther.* 17(8): 1418-26). Because SBOs are intended to alter the form of an mRNA but not destroy that mRNA, oligonucleotides of this class are made using chemistries which are compatible with steric blocking antisense mechanism of action and not chemistries or designs that trigger RNA degradation. One example of the use of SBOs induces exon-skipping in the dystrophin gene in individuals having a mutant form of this gene which causes Duchene's Muscular Dystrophy (see Muntoni and Wood, 2011, *Nat. Rev. Drug Discov.* 10(8): 621-37; and Goemans et al., 2011, *N. Engl. J. Med.* 364(16): 1513-22). Synthetic oligonucleotides using the design and chemistries of the present invention can be employed as SBOs.

In one embodiment, a synthetic oligonucleotide comprises a non-nucleotide modifier of the present invention positioned at or near one or both ends of the sequence. In another embodiment, a synthetic oligonucleotide comprises a non-nucleotide modifier of the present invention positioned between a terminal base and a penultimate base of either the 3'- or the 5'-end of the oligonucleotide. In a further embodiment, the oligonucleotide contains a modification between the terminal base and the penultimate base of both the 3'- and 5'-ends.

In one embodiment of the invention, the modification is a napthylene-azo compound. The oligonucleotide is made using modified bases such that the complex of the SBO with the target pre-mRNA does not form a substrate for RNase H, using chemically-modified residues that are well known to those with skill in the art, including, for example, 2'-O-methyl RNA, 2'-methyoxyethyl RNA (2'-MOE), 2'-F RNA, LNA, and the like. SBOs made using the non-nucleotide modifiers of the present invention have increased binding affinity compared to the cognate unmodified species. This can permit use of shorter sequences, which can show improved uptake into cells and improved biological activity.

In another embodiment of the invention, the modification has the structure:

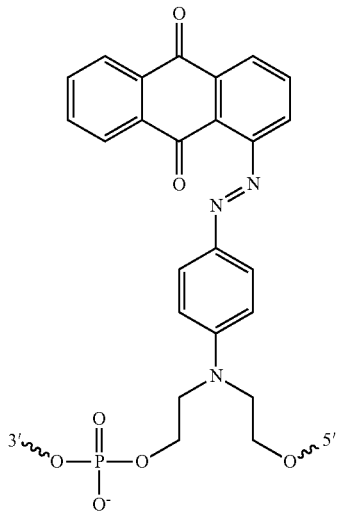

Formula 5

In a further embodiment of the invention, the modification has the structure:

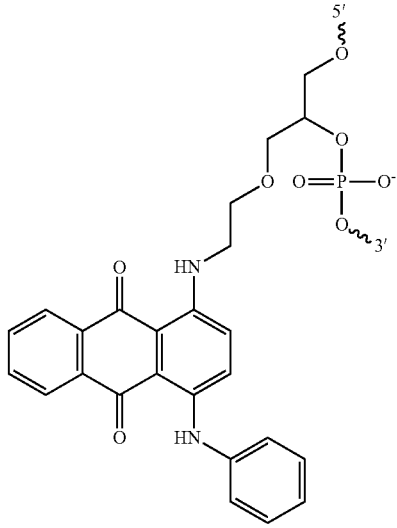

Formula 6

The antisense oligonucleotides of the invention may be conjugated to other ligands, which may aid in the delivery of the antisense oligonucleotide to a cell or organism. In one embodiment of the invention, the ligand is 5' cholesterol monoethyleneglycol (/5CholMEG/):

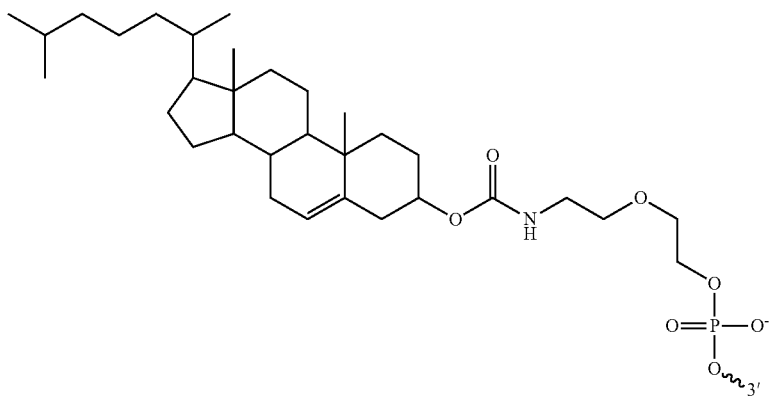

In another embodiment of the invention, the ligand is 5' cholesterol triethyleneglycol (/5Chol-TEG/):

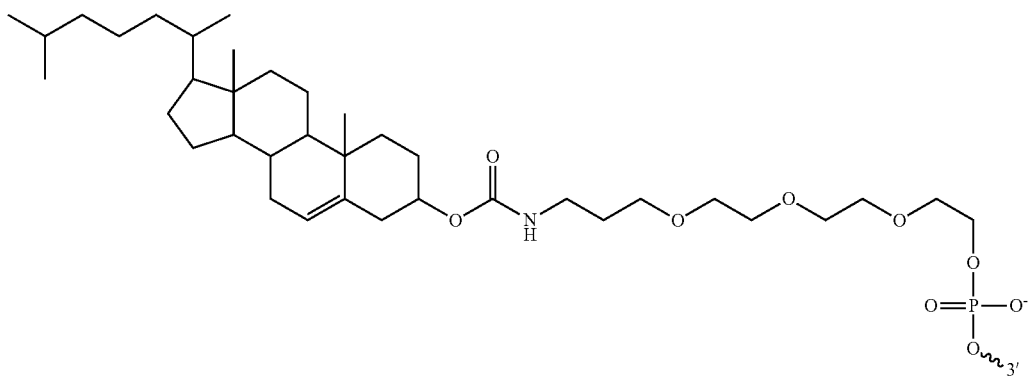

In a further embodiment of the invention, the ligand is 3' cholesterol monoethyleneglycol (/3CholMEG/):

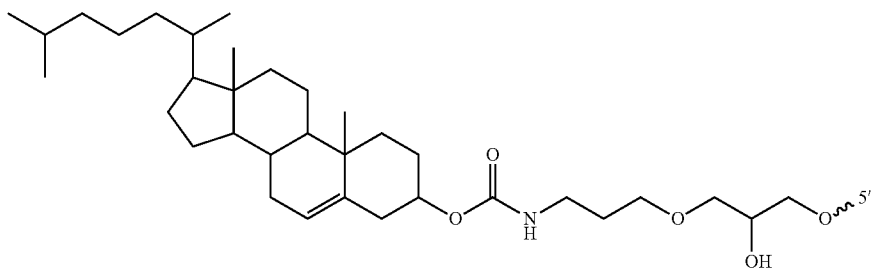

In another embodiment of the invention, the ligand is 3' cholesterol triethyleneglycol (/3CholTEG/):

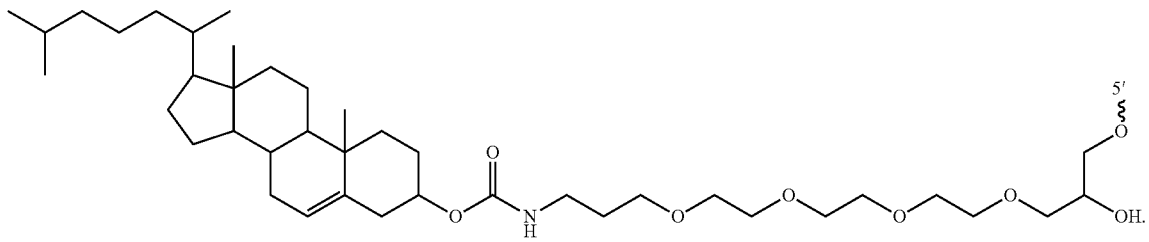

The ligand may be conjugated to the antisense oligonucleotide with or without an additional S18 (hexaethyleneglycol) spacer. In a preferred embodiment, the antisense oligonucleotide is an anti-miRNA oligonucleotide (AMO). In another preferred embodiment, the non-nucleotide modification is a FQ napthylene-azo compound (also referred to as iFQ or ZEN in this disclosure).

The following examples further illustrate the invention but, of course, should not be construed as in any way limiting its scope.

Example 1

This example demonstrates the improved thermal stability of internal napthylene-azo-containing oligomers compared to other compounds.

Oligonucleotide Synthesis and Preparation.

DNA oligonucleotides were synthesized using solid phase phosphoramidite chemistry, deprotected and desalted on NAP-5 columns (Amersham Pharmacia Biotech, Piscataway, N.J.) according to routine techniques (Caruthers et al., 1992, Methods Enzymol. 211: 3-20). The oligomers were purified using reversed-phase high performance liquid chromatography (RP-HPLC). The purity of each oligomer was determined by capillary electrophoresis (CE) carried out on a Beckman P/ACE MDQ system (Beckman Coulter, Inc., Fullerton, Calif.). All single-strand oligomers were at least 90% pure. Electrospray-ionization liquid chromatography mass spectrometry (ESI-LCMS) of the oligonucleotides was conducted using an Oligo HTCS system (Novatia, Princeton, N.J.), which consisted of ThermoFinnigan TSQ7000, Xcalibur data system, ProMass data processing software, and Paradigm MS4™ HPLC (Michrom BioResources, Auburn, Calif.). Protocols recommended by the manufacturers were followed. Experimental molar masses for all single-strand oligomers were within 1.5 g/mol of expected molar mass. These results confirm identity of the oligomers.

Preparation of DNA Samples.

Melting experiments were carried out in buffer containing 3.87 mM $NaH_2PO_4$, 6.13 mM $Na_2HPO_4$, 1 mM $Na_2EDTA$, and 1000 mM NaCl. 1 M NaOH was used to titrate each solution to pH 7.0. Total sodium concentrations were estimated to be 1020 mM. The DNA samples were thoroughly dialyzed against melting buffer in a 28-well Microdialysis System (Life Technologies, Carlsbad, Calif.) following the manufacturer's recommended protocol. Concentrations of DNA oligomers were estimated from the samples' UV absorbance at 260 nm in a spectrophotometer (Beckman Coulter, Inc., Fullerton, Calif.), using extinction coefficients for each oligonucleotide that were estimated using the nearest neighbor model for calculating extinction coefficients (see Warshaw et al., 1966, J. Mol. Biol. 20(1): 29-38).

Internal Modifications Studied.

The FQ napthylene-azo compound (Formula 3, Integrated DNA Technologies, Inc., sometimes referred to as "iFQ" or "ZEN" in this disclosure), was introduced into oligonucleotides using phosphoramidite reagents at the time of synthesis.

Formula 3

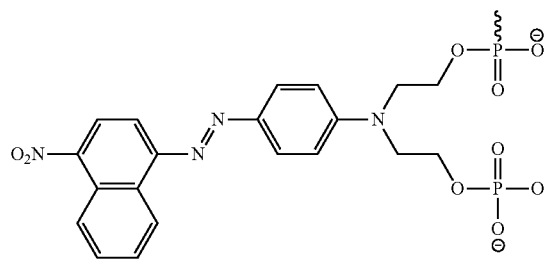

In the first series of duplexes, the iFQ group was placed as an insertion between bases in the duplex so that a 10-base top strand annealed to a 10-base bottom strand and the iFQ group was not aligned to a base. Additionally, 10-mer oligonucleotides with C3 spacer insertions were also synthesized and studied. The C3 spacer represents the control wherein a linear insertion of a phosphate group plus propanediol is placed between bases, which is similar to the iFQ insertions without having the napthylene-azo ring structures present. Extinction coefficients at 260 nm of iFQ were estimated to be 13340; the C3 spacer does not contribute to UV absorbance.

In a second series of duplexes, the iFQ group was placed as a substitution for a base in the duplex so that a 9-base top strand annealed to a 10-base bottom strand and the iFQ group was aligned to a base. Additionally, 10-mer oligonucleotides with C3 spacer substitutions were also synthesized and studied.

Measurement of Melting Curves.

Oligomer concentrations were measured at least twice for each sample. If the estimated concentrations for any sample differed more than 4%, the results were discarded and new absorbance measurements were performed. To prepare oligonucleotide duplexes, complementary DNA oligomers were mixed in 1:1 molar ratio, heated to 367 K (i.e., 94° C.) and slowly cooled to an ambient temperature. Each solution of duplex DNA was diluted with melting buffer to a total DNA concentration ($C_T$) of 2 µM.

Melting experiments were conducted on a single beam Beckman DU 650 spectrophotometer (Beckman-Coulter) with a Micro $T_m$ Analysis accessory, a Beckman High Performance Peltier Controller (to regulate the temperature), and 1 cm path-length cuvettes. Melt data were recorded using a PC interfaced to the spectrophotometer. UV-absorbance values at 268 nm wavelength were measured at 0.1 degree increments in the temperature range from 383 to 368 K (i.e., 10-95° C.). Both heating (i.e., "denaturation") and cooling (i.e., "renaturation") transition curves were recorded in each sample at a controlled rate of temperature change (24.9±0.3° C. per hour). Sample temperatures were collected from the internal probe located inside the Peltier holder, and recorded with each sample's UV-absorbance data. Melting profiles were also recorded for samples of buffer alone (no oligonucleotide), and these "blank" profiles were digitally subtracted from melting curves of the DNA samples. To minimize systematic errors, at least two melting curves were collected for each sample in different cuvettes and in different positions within the Peltier holder.

Determination of Melting Temperatures.

To determine each sample's melting temperature, the melting profiles were analyzed using methods that have been previously described (see Doktycz et al., 1992, *Biopolymers* 32(7): 849-64; Owczarzy et al., 1997, *Biopolymers* 44(3): 217-39; and Owczarzy, 2005, *Biophys. Chem.* 117(3): 207-15.). Briefly, the experimental data for each sample was smoothed, using a digital filter, to obtain a plot of the sample's UV-absorbance as a function of its temperature. The fraction of single-stranded oligonucleotide molecules, θ, was then calculated from that plot. The "melting temperature" or "$T_m$" of a sample was defined as the temperature where θ=0.5. Table 1 lists the melting temperatures of the oligonucleotides tested.

TABLE 1

Melting temperatures for nucleic acids containing a single internal modifying group as an insertion

| SEQ ID NO: | Sequence | | $T_m$ | $\Delta T_m$ | Avg $\Delta T_m$ |
|---|---|---|---|---|---|
| 1 | 5' ATCGTTGCTA | | 43.9 | — | |
| 2 | 3' TAGCAACGAT | | | | |
| 3 | 5' ATC/GTTGCTA | iFQ "/" | 48.0 | 4.1 | +3.7 |
| 2 | 3' TAG CAACGAT | | | | |
| 4 | 5' ATCG/TTGCTA | iFQ "/" | 48.6 | 4.7 | |
| 2 | 3' TAGC AACGAT | | | | |
| 5 | 5' ATCGT/TGCTA | iFQ "/" | 46.3 | 2.4 | |
| 2 | 3' TAGCA ACGAT | | | | |
| 6 | 5' A/TCGTTGCTA | iFQ "/" | 51.75 | 7.9 | +7.2 |
| 2 | 3' T AGCAACGAT | | | | |
| 7 | 5' ATCGTTGCT/A | iFQ "/" | 50.25 | 6.4 | |
| 2 | 3' TAGCAACGA T | | | | |
| 8 | 5' ATC/GTTGCTA | iSpC3 "/" | 36.3 | -7.6 | -8.7 |
| 2 | 3' TAG CAACGAT | | | | |
| 9 | 5' ATCG/TTGCTA | iSpC3 "/" | 36.6 | -7.3 | |
| 2 | 3' TAGC AACGAT | | | | |
| 10 | 5' ATCGT/TGCTA | iSpC3 "/" | 32.6 | -11.3 | |
| 2 | 3' TAGCA ACGAT | | | | |

"/" signifies the site of insertion of a modifying group between bases as indicated.
iFQ = internal FQ azo quencher (ZEN)
iSpC3 = internal C3 spacer When the iFQ (ZEN) modifier was inserted centrally within a 10-mer oligonucleotide (between bases 3/4, 4/5, or 5/6), $T_m$ was increased by an average of 3.7° C. When placed between terminal residues (between bases 1/2 or 9/10), $T_m$ was increased by an average of 7.2° C. In contrast, insertion of a small propanediol group (C3 spacer) had a significant negative impact on the $T_m$ of the duplex (average $\Delta T_m$ of −8.7° C.).

A subset of these sequences were studied using the internal modifications as base substitutions, such that now a 9-base top strand annealed to a 10-base bottom strand with the modification replacing a base and being aligned with a base on the opposing strand. Results are shown in Table 2. In this case, it is evident that the base substitution was significantly destabilizing whereas the insertions (Table 1) were stabilizing (ZEN) or were at least less destabilizing (C3).

TABLE 2

Melting temperatures for nucleic acids containing a single internal modifying group comparing substitution vs. insertion

| SEQ ID NO: | Duplex Sequence | | Ins vs. Subs | $T_m$ | $T_m$ |
|---|---|---|---|---|---|
| 1 | 5'-ATCGTTGCTA-3' | — | | 43.9 | 0.0 |
| 2 | 3'-TAGCAACGAT-5' | | | | |
| 3 | 5'-ATC/GTTGCTA-3' | iFQ "/" | I | 48.0 | 4.1 |
| 2 | 3'-TAG CAACGAT-5' | | | | |
| 8 | 5'-ATC/GTTGCTA-3' | iSpC3 "/" | I | 36.3 | -7.6 |
| 2 | 3'-TAG CAACGAT-5' | | | | |
| 11 | 5'-ATC/TTGCTA-3' | iFQ "/" | S | 34.7 | -9.2 |
| 2 | 3'-TAGCAACGAT-5' | | | | |
| 12 | 5'-ATC/TTGCTA-3' | iSpC3 "/" | S | <20 | |
| 2 | 3'-TAGCAACGAT-5' | | | | |
| 13 | 5'-ATCG/TTGCTA-3' | iFQ "/" | I | 48.6 | 4.7 |
| 2 | 3'-TAGC AACGAT-5' | | | | |
| 14 | 5'-ATCG/TTGCTA-3' | iSpC3 "/" | I | 36.6 | -7.3 |
| 2 | 3'-TAGC AACGAT-5' | | | | |
| 15 | 5'-ATCG/TGCTA-3' | iFQ "/" | S | 38.2 | -5.7 |
| 2 | 3'-TAGCAACGAT-5' | | | | |
| 16 | 5'-ATCG/TGCTA-3' | iSpC3 "/" | S | <24 | |
| 2 | 3'-TAGCAACGAT-5' | | | | |
| 17 | 5'-ATCGT/TGCTA-3' | iFQ "/" | I | 46.3 | 2.4 |
| 2 | 3'-TAGCA ACGAT-5' | | | | |
| 18 | 5'-ATCGT/TGCTA-3' | iSpC3 "/" | I | 32.6 | -11.3 |
| 2 | 3'-TAGCA ACGAT-5' | | | | |
| 19 | 5'-ATCGT/GCTA-3' | iFQ "/" | S | 40.8 | -3.1 |
| 2 | 3'-TAGCAACGAT-5' | | | | |
| 20 | 5'-ATCGT/GCTA-3' | iSpC3 "/" | S | <26 | |
| 2 | 3'-TAGCAACGAT-5' | | | | |

For this series of internal modifications, the average $\Delta T_m$ for iFQ (ZEN) insertion was +3.7° C. while the average $\Delta T_m$ for iFQ (ZEN) substitution was −6° C. The average $\Delta T_m$ for iC3 spacer insertion was −8.7° C. while the average $\Delta T_m$ for iC3 spacer substitution was more than −20° C. (accurate measurements were not possible as the $T_m$ was below room temperature). Therefore insertion placement is preferred to substitution placement.

The napthylene-azo modifier was introduced into the same 10-mer oligomer sequence at 2 or 3 sites, either adjacent to or separated by several bases. Duplexes were formed and $T_m$ values were measured as before. Results are shown in Table 3. Some of the singly modified duplexes from Table 1 are also included in Table 3 to improve clarity of comparisons between modification patterns.

TABLE 3

Melting temperatures for nucleic acids containing multiple internal modifying groups as insertions

| SEQ ID NO: | Sequence | | $T_m$ | $\Delta T_m$ |
|---|---|---|---|---|
| 1 | 5' ATCGTTGCTA | | 43.87 | — |
| 2 | 3' TAGCAACGAT | | | |
| 3 | 5' ATC/GTTGCTA | 1x iFQ | 48.02 | 4.15 |
| 2 | 3' TAG CAACGAT | "/" | | |
| 21 | 5' ATC//GTTGCTA | 2x iFQ | 39.62 | −4.25 |
| 2 | 3' TAG CAACGAT | "//" | | |
| 22 | 5' ATC/GTT/GCTA | 2x iFQ | 46.72 | 2.85 |
| 2 | 3' TAG CAA CGAT | "/.../" | | |
| 23 | 5' ATC/GT/TG/CTA | 3x iFQ | 43.36 | −0.51 |
| 2 | 3' TAG CA AC GAT | "/../../" | | |
| 13 | 5' ATCG/TTGCTA | 1x iFQ | 48.57 | 4.70 |
| 2 | 3' TAGC AACGAT | "/" | | |
| 24 | 5' ATCG//TTGCTA | 2x iFQ | 39.82 | −4.05 |
| 2 | 3' TAGC AACGAT | "//" | | |
| 17 | 5' ATCGT/TGCTA | 1x iFQ | 46.32 | 2.45 |
| 2 | 3' TAGCA ACGAT | "/" | | |
| 25 | 5' ATCGT//TGCTA | 2x iFQ | 36.76 | −8.90 |
| 2 | 3' TAGCA ACGAT | "/" | | |
| 26 | 5' A/TCGTTGCTA | 1x iFQ | 51.75 | 7.88 |
| 2 | 3' T AGCAACGAT | "/" | | |
| 27 | 5' ATCGTTGCT/A | 1x iFQ | 50.25 | 6.38 |
| 2 | 3' TAGCAACGA T | "/" | | |
| 28 | 5' A/TCGTTGCT/A | 2x iFQ | 54.91 | 11.04 |
| 2 | 3' T AGCAACGA T | "/" | | |

"/" signifies the site of insertion of a modifying group between bases as indicated.

Insertion of two adjacent napthylene-azo modifiers was destabilizing and $T_m$ was found to change by −4 to −8.9° C. depending on sequence context. Placing two napthylene-azo modifying groups in the same sequence separated by 3 bases was slightly stabilizing ($T_m$+2.9° C.); however, this was less stabilizing than use of a single modifier alone ($T_m$+4.7° C.). Use of 3 modifier groups separated by 2 bases between groups was destabilizing. However, when two napthylene-azo modifier groups were placed at the ends (between both bases 1/2 and 9/10), $T_m$ was increased by 11° C. Thus, an additive effect can be obtained by placing multiple insertions of the modifying group into a sequence so long as a sufficient number of bases separate the groups. End effects are particularly potent.

Therefore, internal incorporation of the napthylene-azo group within a DNA duplex stabilizes the duplex when placed as an insertion between bases. Certain anthraquinone groups can stabilize a duplex when placed on the ends (Patra et al., 2009, *J. Am. Chem. Soc.* 131(35): 12671-81); however, this effect has not been described for internal placement. Therefore, the use of napthylene-azo-class compounds would be preferred as an internal modifying group to increase duplex stability.

Example 2

This example demonstrates the improved nuclease stability of internal napthylene-azo-containing oligomers compared to other compounds.

Oligonucleotide Synthesis and Purification.

DNA oligonucleotides were synthesized using solid phase phosphoramidite chemistry, deprotected and desalted on NAP-5 columns (Amersham Pharmacia Biotech, Piscataway, N.J.) according to routine techniques (Caruthers et al., 1992). The oligomers were purified using reversed-phase high performance liquid chromatography (RP-HPLC). The purity of each oligomer was determined by capillary electrophoresis (CE) carried out on a Beckman P/ACE MDQ system (Beckman Coulter, Inc., Fullerton, Calif.). All single-strand oligomers were at least 90% pure. Electrospray-ionization liquid chromatography mass spectrometry (ESI-LCMS) of the oligonucleotides was conducted using an Oligo HTCS system (Novatia, Princeton, N.J.), which consisted of ThermoFinnigan TSQ7000, Xcalibur data system, ProMass data processing software, and Paradigm MS4™ HPLC (Michrom BioResources, Auburn, Calif.). Protocols recommended by the manufacturers were followed. Experimental molar masses for all single-strand oligomers were within 1.5 g/mol of expected molar mass. These results confirm identity of the oligomers. The synthesized oligonucleotides are listed in Table 4.

TABLE 4

Synthetic oligomers employed in Example 2

| SEQ ID NO: | Name | Sequence |
|---|---|---|
| 1 | DNA | 5' ATCGTTGCTA 3' |
| 26 | 5' iFQ | 5' A (iFQ) TCGTTGCTA 3' |
| 27 | 3' iFQ | 5' ATCGTTGCT (iFQ) A 3' |
| 28 | 5' + 3' iFQ | 5' A (iFQ) TCGTTGCT (iFQ) A 3' |
| 29 | 5' iC3 | 5' A (iSpC3) TCGTTGCTA 3' |
| 30 | 3' iC3 | 5' ATCGTTGCT (iSpC3) A 3' |
| 31 | 5' + 3' iC3 | 5' A (iSpC3) TCGTTGCT (iSpC3) A 3' |

Radiolabeling of Oligomers.

Single-stranded oligomers were radiolabeled at the 5'-end using polynucleotide kinase. Briefly, 5 pmoles of each oligonucleotide were incubated with 10 units of OptiKinase (USB, Cleveland, Ohio) and 10 pmoles of alpha $^{32}$P γ-ATP (3000 Ci/mmol) (Perkin Elmer, Waltham, Mass.) for 30 minutes at 37° C., followed by 65° C. for 10 minutes. Excess radionucleotide was removed by gel filtration using two sequential passes through MicroSpin G-25 columns (GE Healthcare, Buckinghamshire, UK). Isotope incorporation was measured in a Perkin Elmer TriCarb 2800 TR scintillation counter (Perkin Elmer, Waltham, Mass.).

Serum Degradation of Oligomers.

As labeling efficiencies varied (lower specific activity was obtained for the oligomers with a modification near the 5'-end), equivalent numbers of dpms of radiolabeled oligomers were mixed with unlabeled oligomers to a final concentration of 8 μM in the presence of 50% fetal bovine serum (not heat inactivated; Invitrogen, Carlsbad, Calif.). Samples were incubated at 37° C. for 0, 30, 60, or 240 minutes; aliquots were removed at the indicated time points, an equal volume of 90% formamide was added, and samples flash frozen on dry ice. Degradation products were separated by PAGE using a 20% polyacrylamide, 7 M Urea denaturing gel and visualized on a Cyclone phosphorimager (Perkin Elmer, Waltham, Mass.). Results are shown in FIG. 1.

The unmodified DNA oligomer was rapidly degraded and no intact full-length material was present after 30 minutes incubation. The sample was fully degraded by 4 hours. A similar pattern of degradation was seen for the oligomer having a single internal C3 spacer positioned near the 5'-end. In contrast, only incomplete degradation was observed for the oligomer bearing a single internal FQ modifier near the 5'-end. The degradation pattern observed is most consistent with processive 3'-exonuclease cleavage that stopped before the oligomer was fully degraded. This suggests the possibility that the iFQ modifier protects neighboring DNA residues from exonuclease degradation, providing a small zone of protection around the 5'-end.

The oligomer having a single internal C3 spacer near the 3'-end shows prompt removal of what appears to be a single base and then was slowly degraded. Slightly greater protection was seen in the oligomer having an internal C3 spacer placed near both ends. In contrast, no evidence was seen for single base cleavage at the 3'-end of the oligomer having a single internal FQ modifier near the 3'-end, and no evidence for degradation was observed after 4 hours incubation in 50% serum for the oligomer having an FQ modifier placed near both ends.

Therefore, the FQ modifier will block exonuclease attack from the enzymes present in fetal bovine serum, and can confer relative nuclease resistance to neighboring unmodified bases, creating a protected "zone" in its vicinity.

Example 3

This example demonstrates improved functional activity of internal napthylene-azo-containing ASOs at reducing microRNA activity compared to other compounds.

Oligonucleotide Synthesis and Purification.

DNA, 2'OMe RNA, and LNA containing oligonucleotides were synthesized using solid phase phosphoramidite chemistry, deprotected and desalted on NAP-5 columns (Amersham Pharmacia Biotech, Piscataway, N.J.) according to routine techniques (Caruthers et al., 1992). The oligomers were purified using reversed-phase high performance liquid chromatography (RP-HPLC). The purity of each oligomer was determined by capillary electrophoresis (CE) carried out on a Beckman P/ACE MDQ system (Beckman Coulter, Inc., Fullerton, Calif.). All single-strand oligomers were at least 85% pure. Electrospray-ionization liquid chromatography mass spectrometry (ESI-LCMS) of the oligonucleotides was conducted using an Oligo HTCS system (Novatia, Princeton, N.J.), which consisted of ThermoFinnigan TSQ7000, Xcalibur data system, ProMass data processing software, and Paradigm MS4™ HPLC (Michrom BioResources, Auburn, Calif.). Protocols recommended by the manufacturers were followed. Experimental molar masses for all single-strand oligomers were within 1.5 g/mol of expected molar mass. These results confirm identity of the oligomers. Table 5 lists the synthetic oligomers used in this Example.

TABLE 5

Synthetic oligomers employed in Example 3 (miR21 AMOs)

| SEQ ID NO: | Name | Sequence |
|---|---|---|
| 32 | 2'OMe | U C A A C A U C A G U C U G A U A A G C U A |
| 33 | 2'OMe PSends | U*C*A*A C A U C A G U C U G A U A A G*C*U*A |
| 34 | 2'OMe PS | U*C*A*A*C*A*U*C*A*G*U*C*U*G*A*U*A*A*G*C*U*A |
| 35 | 2'OMe 5' + 3'iFQ | U$_z$C A A C A U C A G U C U G A U A A G C U$_z$A |
| 36 | 2'OMePS 5' + 3'iFQ | U$_z$C*A*A*C*A*U*C*A*G*U*C*U*G*A*U*A*A*G*C*U$_z$A |
| 37 | 2'OMe 3'iFQ | U C A AC A U C A G U C U G A U A A G C U$_z$A |
| 38 | 2'OMe 5'iFQ | U$_z$C A A C A U C A G U C U G A U A A G C U A |
| 39 | 2'OMe 5' + I + 3'iFQ | U$_z$C A A C A U C A G U$_z$C U G A U A A G C U$_z$A |
| 40 | DNA/LNA PS | t*<u>C</u>*a*a*<u>C</u>*a*t*<u>C</u>*a*g*<u>T</u>*c*t*<u>G</u>*a*t*<u>A</u>*a*g*<u>C</u>*t*a |
| 41 | 2'OMe/LNA PS | U*<u>C</u>*A*A*<u>C</u>*A*U*<u>C</u>*A*G*<u>T</u>*C*U*<u>G</u>*A*U*<u>A</u>*A*G*<u>C</u>*U*A |

Uppercase = 2'OMe RNA
Lowercase = DNA
Uppercase with underscore = LNA
"*" = phosphorothioate linkage
"z" = napthylene-azo modifier (iFQ)

Plasmid Preparation.

The psiCHECK™-2 vector (Promega, Madison, Wis.) was restriction enzyme digested sequentially with Xho1 and Not1 (New England Biolabs, Ipswitch, Mass.) and purified with a Qiaquick PCR purification column (Qiagen, Valencia, Calif.). A perfect complement hsa-miR-21 binding site was created by annealing two synthetic duplexed oligonucleotides (Integrated DNA Technologies, Coralville, Iowa) and was cloned into the Xho1/Not1 sites in the 3'UTR of Renilla luciferase. This miR-21' reporter construct was sequence verified on a 3130 Genetic Analyzer (AB, Foster City, Calif.). Plasmids were purified using a Plasmid Midiprep Kit (Bio-Rad, Hercules, Calif.) and treated twice for endotoxin removal with the MiraCLEAN Endotoxin Removal Kit (Minis Corporation, Madison, Wis.). Plasmids were filtered through a 0.2μ filter and quantified by measurement of the absorbance at 260 nm using UV spectrophotometry. This reporter plasmid having a perfect match miRNA binding site is denoted as psiCHECK™-2-miR21.

Cell Culture, Transfections, and Luciferase Assays.

HeLa cells were plated in a 100 mm dish in DMEM containing 10% FBS to achieve 90% confluency the next day. The following morning, 5 μg of the psiCHECK™-2-miR21 plasmid was transfected with Lipofectamine™ 2000 (Invitrogen, Carlsbad, Calif.). After 6 hours, cells were washed with 1×PBS, trypsinized, counted, and replated in DMEM with 10% FBS in 48-well plates to achieve ~70% confluency the next day. The following morning, the miR-21 AMOs were transfected at various concentrations in triplicate with 1 μl TriFECTin® (Integrated DNA Technologies) per well in DMEM without serum. After 6 hours, the transfection media was removed and replenished with DMEM containing 10% FBS. The following morning, (48 hours after plasmid transfection, 24 hours after miRNA AMO transfection) the cells were analyzed for luciferase luminescence using the Dual-Luciferase® Reporter Assay System (Promega, Madison, Wis.) per the manufacturer's instructions. Renilla luciferase was measured as a fold increase in expression compared to the TriFECTin® reagent-only negative controls. Values for Renilla luciferase luminescence were normalized to levels concurrently measured for firefly luciferase, which is present as a separate expression unit on the same plasmids as an internal control (RLuc/FLuc ratio).

Results.

Figure 2:
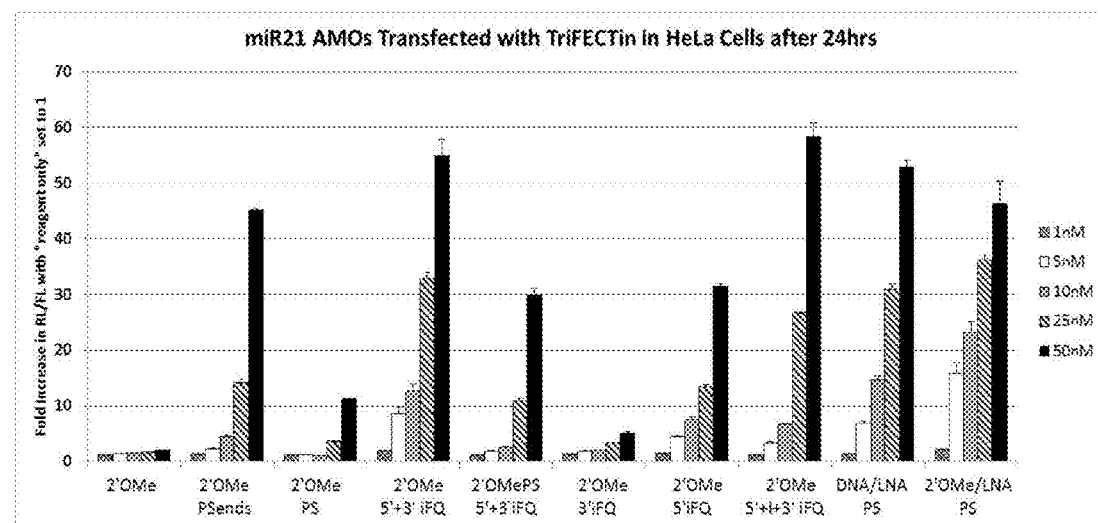
FIG. 2 illustrates relative miR-21 suppression by various anti-miRNA oligonucleotides (AMOs) using a luciferase reporter assay. A reporter plasmid that expresses both Renilla luciferase and firefly luciferase was transfected into HeLa cells. Cell extracts were studied for relative activity of both enzymes and Renilla luciferase activity was normalized to firefly luciferase activity. The Renilla luciferase gene contains a miR-21 binding site and miR-21 is highly expressed in HeLa cells. Different anti-miR-21 oligonucleotides (X-axis) were transfected into the cells and the relative ability of different designs to suppress miR-21 activity directly relate to the increase in Renilla luciferase activity (Y-axis).

The RLuc/FLuc ratios obtained from transfections done with the various AMOs are shown in FIG. 2. In the untreated state, HeLa cells contain large amounts of miRNA 21 that suppress expression of the RLuc reporter. Any treatment that decreases miR-21 levels leads to an increase in RLuc expression and thus increases the relative RLuc/FLuc ratio (with FLuc serving as an internal normalization control for transfection efficiency).

The unmodified 2'OMe RNA AMO showed essentially no inhibition of miR-21 activity, probably due to rapid nuclease degradation of this unprotected oligomer during transfection or in the intracellular environment. The addition of 3 PS linkages on each end of the AMO blocks exonuclease attack and the "2'OMe-PSends" AMO showed good potency for functional knockdown of miR-21. When this AMO is changed to be fully PS modified ("2'OMe-PS"), potency drops, which is probably due to having lower binding affinity (lower $T_m$) that accompanies extensive PS modification. Each substitution of a PS bond for a standard phosphodiester bond reduces $T_m$, and there are 21 PS bonds in this oligomer compared with only 6 PS bonds in the "2'OMe PSends" version.

A desirable modification chemistry or modification pattern is one that both increases nuclease stability and increases $T_m$. The internal napthylene-azo modifier meets these criteria. The 2'OMe oligomer having an internal napthylene-azo modifier placed between the terminal and adjacent bases on each end (2'OMe 5'+3'iFQ) showed markedly improved anti-miR21 activity and was more potent than any of the PS modified 2'OMe AMOs tested. Adding PS modification to this design (2'OMePS 5'+3'iFQ) reduced potency, likely due to the lower binding affinity caused by the addition of 19 PS linkages. This compound was nevertheless still significantly more potent than the 2'OMe-PS version without the 2 iFQ modifications.

Protecting only one end of the anti-miR-21 AMO with an internal napthylene-azo modifier showed improved potency when compared with the unmodified 2'OMe AMO; however, the performance was much reduced compared with the dual-modified version. Interestingly, modification at the 5'-terminal linkage had more effect than modification at the 3'-terminal linkage, the exact opposite of the results anticipated from the relative serum stability profiles demonstrated in Example 2. This result is explained by measured effects of $T_m$ (see Table 6).

Addition of a third iFQ modification into the end-blocked version (2'OMe 5'+I+3'iFQ) showed reduced potency compared with the original end-blocked version (2'OMe 5'+3'iFQ), which is likely due to a reduction of $T_m$ seen with placing this many iFQ modifying groups in a single, short 22-mer sequence.

The "DNA/LNA-PS" AMO is a design employed by Exiqon as its preferred anti-miRNA agent and is widely accepted as the "gold standard" for miRNA knockdown studies performed today. The DNA/LNA compound showed the same potency as the dual-modified "2'OMe 5'+3'iFQ" AMO. The "2'OMe/LNA-PS" AMO showed highest potency within the set studied. The LNA modification confers nuclease resistance and gives very large increases in $T_m$, resulting in AMOs with higher potency but also having lower specificity than AMOs without LNA bases with lower binding affinity. The relative specificity of the different AMOs is presented in Example 4 below. Of note, the LNA-PS modified AMOs show some toxicity and cell cultures transfected with the highest doses (50 nM) had dysmorphic, unhealthy appearing cells at the time of harvest. The "2'OMe 5'+3'iFQ" AMO did not show any visual evidence for toxicity at any of the doses tested. In subsequent experimentation, toxicity effects were evaluated at high doses by measuring cell viability, cytotoxicity, and induction of apoptosis (see Example 7). The "2'OMe 5'+3'iFQ" chemistry showed no cellular toxicity, compared to the substantial cellular toxicity that occurred upon transfection of single-stranded oligonucleotides containing LNA bases, extensive PS modification (all 21 linkages), or both LNA and PS modifications (the "gold standard" AMO). Thus, the "2'OMe 5'+3'iFQ" may be a new class of AMO that achieves high potency yet maintains low toxicity.

The melting temperatures, $T_m$, of the AMOs described above were measured using the same methods described in Example 1. Synthetic AMO oligonucleotides were annealed to a synthetic RNA complement (mature miR21 sequence). Measurements were done at 2 μM duplex concentration in 150 mM NaCl to approximate intracellular ion concentration.

TABLE 6

$T_m$ of synthetic miR21 AMOs in 150 mM NaCl

| SEQ ID NO: | Name | Sequence | $T_m$ | $\Delta T_m$ |
|---|---|---|---|---|
| 32 | 2'OMe | U C A A C A U C A G U C U G A U A A G C U A | 72.1 | — |
| 33 | 2'OMe PSends | U*C*A*A C A U C A G U C U G A U A A G*C*U*A | 70.9 | −1.2 |
| 34 | 2'OMe PS | U*C*A*A*C*A*U*C*A*G*U*C*U*G*A*U*A*A*G*C*U*A | 67.1 | −5.0 |
| 35 | 2'OMe 5' + 3'iFQ | U$_z$C A A C A U C A G U C U G A U A A G C U$_z$A | 75.4 | +3.3 |
| 36 | 2'OMePS 5' + 3'iFQ | U$_z$C*A*A*C*A*U*C*A*G*U*C*U*G*A*U*A*A*G*C*U$_z$A | 70.6 | −1.5 |
| 37 | 2'OMe 3'iFQ | U C A A C A U C A G U C U G A U A A G C U$_z$A | 72.4 | +0.3 |
| 38 | 2'OMe 5'iFQ | U$_z$C A A C A U C A G U C U G A U A A G C U A | 74.3 | +2.2 |
| 39 | 2'OMe 5' + I + 3'iFQ | U$_z$C A A C A U C A G U$_z$C U G A U A A G C U$_z$A | 71.3 | −0.8 |
| 40 | DNA/LNA PS | t*<u>C</u>*a*a*<u>C</u>*a*t*<u>C</u>*a*g*<u>T</u>*c*t*<u>G</u>*a*t*<u>A</u>*a*g*<u>C</u>*t*a | 74.0 | +1.9 |
| 41 | 2'OMe/LNA PS | U*<u>C</u>*A*A*<u>C</u>*A*U*<u>C</u>*A*G*<u>T</u>*C*U*<u>G</u>*A*U*<u>A</u>*A*G*<u>C</u>*U*A | 85.9 | +13.8 |

Uppercase = 2'OMe RNA
Lowercase = DNA
Uppercase with underscore = LNA
"*" = phosphorothioate linkage
"z" = insertion of napthylene-azo modifier (iFQ)

The 22-mer 2'OMe miR21 AMO showed a $T_m$ of 72.1° C. when hybridized to an RNA perfect complement in 150 mM NaCl. Substitution of 6 PS bonds for native PO linkages lowered $T_m$ by 1.2° C. ("2'OMe PSends") and complete PS modified lowered $T_m$ by 5.0° C. ("2'OMe PS"), a change of −0.20 to −0.25° C. per modified internucleotide linkage. In contrast, insertion of an iFQ group at the 3'-terminal linkage ("2'OMe 3'iFQ") resulted in a $T_m$ increase of +0.3° C. and at the 5'-terminal linkage ("2'OMe 5'iFQ") resulted in a $T_m$ increase of +2.2° C. Combining these two designs, addition of two iFQ modifications (one at each terminal linkage, "2'OMe 5'+3'iFQ") increased $T_m$ to 75.4° C., which is a change of +3.3° C. compared with the unmodified sequence or +4.5° C. relative to the PS-end blocked sequence (which is the most relevant comparison). This dual-end-modification pattern results in good nuclease resistance (FIG. 1) and when employed in a 2'OMe AMO shows increased $T_m$ (Table 6) and is a very potent anti-miR21 agent (FIG. 2). Interestingly, addition of a third iFQ group centrally placed ("2'OMe 5'+I+3' iFQ") resulted in a $T_m$ decrease of 0.8° C. relative to the unmodified compound, or a decrease of 4.1° C. relative to the two-end insertion version ("2'OMe 5'+3'iFQ"). Thus while inserting the iFQ modifier between terminal bases increases $T_m$, adding a third modification in the center of the sequence leads to a decrease in $T_m$, even though these modifications are fully 10 bases distant from each other. This loss of $T_m$ results in a loss of functional potency (FIG. 2). Therefore the dual-modified end-insertion pattern is preferred.

As a general rule, the relative potency of the various miR21 AMOs correlated with increased binding affinity ($T_m$). All variations in potency observed between compounds could be explained by relative contributions of improvements in binding affinity and nuclease stability between the different modification patterns studied. The AMO having 2'OMe bases with an iFQ modification placed near each end ("2'OMe 5'+3'iFQ") provided an excellent balance of nuclease stability with increased $T_m$ and the only AMO showing higher potency was the "2'OMe/LNA-PS" compound. The "2'OMe/LNA-PS" compound, however, showed reduced specificity due to its extreme elevation in binding affinity (see Example 4) and increased cellular toxicity (see Example 7). Therefore, the novel "2'OMe 5'+3'iFQ" design of the present invention is superior.

Example 4

This example demonstrates improved specificity of internal napthylene-azo-containing oligomers when reducing microRNA activity compared to other compounds containing modifications that increase binding affinity.

Three of the more potent AMO designs from the functional study performed in Example 3 were examined in greater detail to assess their relative ability to discriminate mismatches between the synthetic anti-miRNA oligonucleotide and their target. In general, high affinity oligonucleotides show high potency but usually show reduced specificity as the high affinity permits hybridization even in the presence of one or more mismatches in complementarity. The designs "2'OMe 5'+3'iFQ", "DNA/LNA-PS", and "2'OMe/LNA-PS" were synthesized as variants having 1, 2, or 3 mismatches to the miR-21 target sequence. Sequences are shown in Table 7. Studies were performed as described in Example 3.

TABLE 7

| SEQ ID NO: | Name | Sequence |
|---|---|---|
| 35 | 2'OMe 5' + 3'iFQ | U_zC A A C A U C A G U C U G A U A A G C U_zA |
| 42 | 2'OMe 5' + 3'iFQ 1MUT | U_zC A A C A U C A G U C U *C* A U A A G C U_zA |
| 43 | 2'OMe 5' + 3'iFQ 2MUT | U_zC A A *G* A U C A G U C U *C* A U A A G CU_zA |
| 44 | 2'OMe 5' + 3'iFQ 3MUT | U_zC A A *G* A U C A G U C U *C* A U A A G *G* U_zA |
| 40 | DNA/LNA PS | t*C*a*a*C*a*t*C*a*g*T*c*t*G*a*t*A*a*g*C*t*a |
| 45 | DNA/LNA PS 1MUT | t*C*a*a*C*a*t*C*a*g*T*c*t*C*a*t*A*a*g*C*t*a |
| 46 | DNA/LNA PS 2MUT | t*C*a*a*G*a*t*C*a*g*T*c*t*C*a*t*A*a*g*C*t*a |
| 47 | DNA/LNA PS 3MUT | t*C*a*a*G*a*t*C*a*g*T*c*t*C*a*t*A*a*g*G*t*a |
| 41 | 2'OMe/LNA PS | U*C*A*A*C*A*U*C*A*G*T*C*U*G*A*U*A*A*G*C*U*A |
| 48 | 2'OMe/LNA PS 1MUT | U*C*A*A*C*A*U*C*A*G*T*C*U*C*A*U*A*A*G*C*U*A |
| 49 | 2'OMe/LNA PS 2MUT | U*C*A*A*G*A*U*C*A*G*T*C*U*C*A*U*A*A*G*C*U*A |
| 50 | 2'OMe/LNA PS 3MUT | U*C*A*A*G*A*U*C*A*G*T*C*U*C*A*U*A*A*G*G*U*A |

Uppercase = 2'OMe RNA
Lowercase = DNA
Uppercase with underscore = LNA
"*" = phosphorothioate linkage
"z" = napthylene-azo modifier (iFQ)
Mutations are identified with bold italic font Results.

Figure 3:
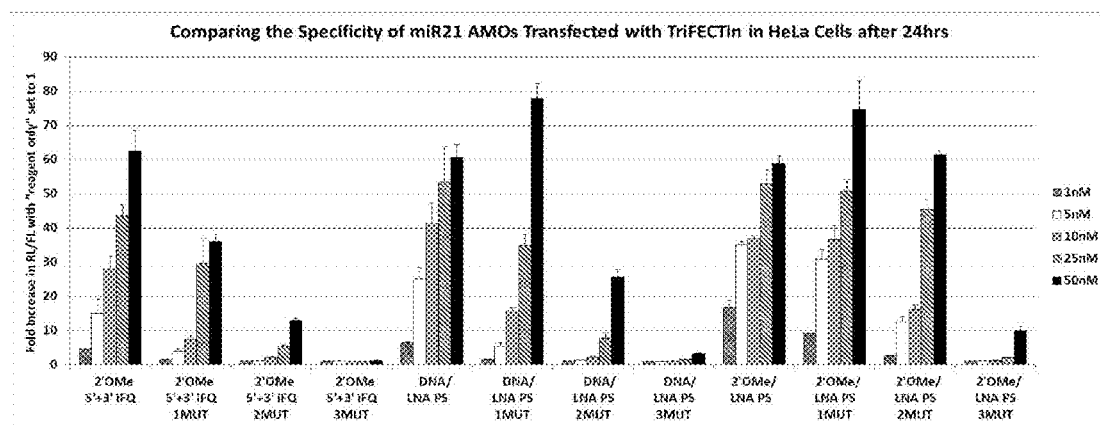
FIG. 3 illustrates relative miR-21 suppression by various AMOs using a luciferase reporter assay comparing perfect match and compounds having 1, 2, or 3 mismatches (mismatch pattern 1). A reporter plasmid that expresses both Renilla luciferase and firefly luciferase was transfected into HeLa cells. Cell extracts were studied for relative activity of both enzymes and Renilla luciferase activity was normalized to firefly luciferase activity. The Renilla luciferase gene contains a miR-21 binding site and miR-21 is highly expressed in HeLa cells. Different anti-miR-21 oligonucleotides (X-axis) were transfected into the cells, and the relative ability of different designs to suppress miR-21 activity directly relate to the increase in Renilla luciferase activity (Y-axis).

The RLuc/FLuc ratios obtained from transfections done with the various AMOs are shown in FIG. 3. In the untreated state, HeLa cells contain large amounts of miRNA 21 that suppress expression of the RLuc reporter. Any treatment that decreases miR-21 levels leads to an increase in RLuc expression and thus increases the relative RLuc/FLuc ratio (with FLuc serving as an internal normalization control for transfection efficiency). For each of the chemistries studied, the parent wild-type sequence is followed by variants having 1, 2, or 3 mutations.

In all cases, the perfect match AMO showed significant suppression of miR-21 activity as evidenced by increases in luciferase levels (increase in the RLuc to FLuc ratio indicating de-repression of the RLuc mRNA). As in Example 3 (FIG. 3), the "2'OMe/LNA-PS" compound showed the highest potency as evidenced by suppression of miR-21 at low dose (1 nM and 5 nM data points). The "2'OMe 5'+3'iFQ" and "DNA/LNA-PS" AMOs showed relatively similar performance both in wild-type (perfect match) and mutant (mismatch) versions. In both cases, a single mismatch showed a partial reduction of anti-miR-21 activity, the double mismatch showed almost complete elimination of anti-miR-21 activity, and the triple mismatch did not show any anti-miR-21 activity. In contrast, the higher affinity "2'OMe/LNA-PS" compound showed significant anti-miR-21 activity for both the single and double mismatch compounds and even showed some activity at high dose (50 nM) for the triple mismatch compound. Thus, while the "2'OMe/LNA-PS" compound is most potent, it is also the least specific of the reagents studied.

Of note, the above experiments were performed using AMOs that placed the mismatches at positions that are LNA modified (in the LNA containing AMOs). This design may influence the likelihood that a mismatch will affect activity as it disrupts a high affinity LNA:RNA base pair. Thus, these results represent the best case scenario for specificity of the LNA-modified AMOs. The experiment was repeated using a new set of reagents where the mismatches were all positioned at non-LNA bases. This new series of AMO reagents is shown in Table 8.

TABLE 8

Synthetic oligomers employed in Example 4 (miR21 AMOs)

| SEQ ID NO: | Name | Sequence |
|---|---|---|
| 35 | 2'OMe 5' + 3'iFQ | U_zC A A C A U C A G U C U G A U A A G C U_zA |
| 51 | 2'OMe 5' + 3'iFQ 1MUT v2 | U_zC A A C A U C A G U C A G A U A A G C U_zA |
| 52 | 2'OMe 5' + 3'iFQ 2MUT v2 | U_zC A A C C U C A G U C A G A U A A G C U_zA |
| 53 | 2'OMe 5' + 3'iFQ 3MUT v2 | U_zC A A C C U C A G U C A G A U A A C C U_zA |
| 40 | DNA/LNA PS | t*C̲*a*a*C̲*a*t*C̲*a*g*T̲*c*t*G̲*a*t*A̲*a*g*C̲*t*a |
| 54 | DNA/LNA PS 1MUT v2 | t*C̲*a*a*C̲*a*t*C̲*a*g*T̲*c*a*G̲*a*t*A̲*a*g*C̲*t*a |
| 55 | DNA/LNA PS 2MUT v2 | t*C̲*a*a*C̲*C*t*C̲*a*g*T̲*c*a*G̲*a*t*A̲*a*g*C̲*t*a |
| 56 | DNA/LNA PS 3MUT v2 | t*C*a*a*C*c*t*C*a*g*T*c*a*G*a*t*A*a*c*C*t*a |
| 41 | 2'OMe/LNA PS | U*C*A*A*C*A*U*C*A*G*T*C*U*G*A*U*A*A*G*C*U*A |
| 57 | 2'OMe/LNA PS 1MUT v2 | U*C*A*A*C*A*U*C*A*G*T*C*A*G*A*U*A*A*G*C*U*A |
| 58 | 2'OMe/LNA PS 2MUT v2 | U*C*A*A*C*C*U*C*A*G*T*C*A*G*A*U*A*A*G*C*U*A |
| 59 | 2'OMe/LNA PS 3MUT v2 | U*C*A*A*C*C*U*C*A*G*T*C*A*G*A*U*A*A*C*C*U*A |

Uppercase = 2'OMe RNA
Lowercase = DNA
Uppercase with underscore = LNA
"*" = phosphorothioate linkage
"z" = napthylene-azo modifier (iFQ)
Mutations are identified with bold italic font Results.

Figure 4:
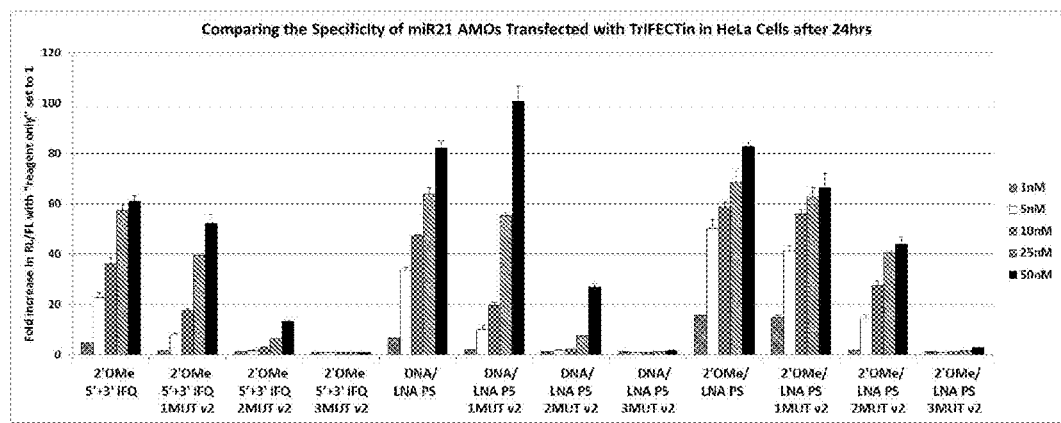
FIG. 4 illustrates relative miR-21 suppression by various AMOs using a luciferase reporter assay comparing perfect match and compounds having 1, 2, or 3 mismatches (mismatch pattern 2). A reporter plasmid that expresses both Renilla luciferase and firefly luciferase was transfected into HeLa cells. Cell extracts were studied for relative activity of both enzymes, and Renilla luciferase activity was normalized to firefly luciferase activity. The Renilla luciferase gene contains a miR-21 binding site and miR-21 is highly expressed in HeLa cells. Different anti-miR-21 oligonucleotides (X-axis) were transfected into the cells, and the relative ability of different designs to suppress miR-21 activity directly relate to the increase in Renilla luciferase activity (Y-axis).

The RLuc/FLuc ratios obtained from transfections done with the various AMOs are shown in FIG. 4. In the untreated state, HeLa cells contain large amounts of miRNA 21 that suppress expression of the RLuc reporter. Any treatment that decreases miR-21 levels leads to an increase in RLuc expression and thus increases the relative RLuc/FLuc ratio (with FLuc serving as an internal normalization control for transfection efficiency). For each of the chemistries studied, the parent wild-type sequence is followed by variants having 1, 2, or 3 mutations.

The results were nearly identical to those obtained with the original mutation mismatch placement (FIG. 3). In all cases, the perfect match AMO showed significant suppression of miR-21 activity as evidenced by increases in luciferase levels (increase in the RLuc to FLuc ratio indicating de-repression of the RLuc mRNA). As in Example 3 (FIG. 3), the "2'OMe/LNA-PS" compound showed the highest potency as evidenced by suppression of miR-21 at low dose (1 nM and 5 nM data points). The "2'OMe 5'+3'iFQ" and "DNA/LNA-PS" AMOs showed relatively similar performance both in wild-type (perfect match) and mutant (mismatch) versions. In both cases, a single mismatch showed a partial reduction of anti-miR-21 activity, the double mismatch showed almost complete elimination of anti-miR-21 activity, and the triple mismatch did not show any anti-miR-21 activity. In contrast, the higher affinity "2'OMe/LNA-PS" compound showed significant anti-miR-21 activity for both the single and double mismatch compounds and even showed some activity at high dose (50 nM) for the triple mismatch compound. Thus, while the "2'OMe/LNA-PS" compound is most potent, it is also the least specific of the reagents studied.

Example 5

This example demonstrates improved functional activity of internal napthylene-azo-containing oligomers at reducing cellular mRNA levels when incorporated into RNase H active ASOs as compared to other related compounds.

Oligonucleotides antisense in orientation to cellular messenger RNAs (mRNAs) will hybridize to the mRNA and form an RNA/DNA heteroduplex, which is a substrate for cellular RNase H. Degradation by RNase H leads to a cut site in the mRNA and subsequently to total degradation of that RNA species, thereby functionally lowering effective expression of the targeted transcript and the protein it encodes. ASOs of this type require a domain containing at least 4 bases of DNA to be a substrate for RNase H, and maximal activity is not seen until 8-10 DNA bases are present. ASOs must be chemically modified to resist degradation by serum and cellular nucleases. Phosphorothioate (PS) modification of the internucleotide linkages is compatible with RNase H activation, however most other nuclease resistant modifications prevent RNase H activity, including all 2'-modifications, such as 2'OMe RNA, LNA, MOE, etc. The PS modification lowers binding affinity ($T_m$). In general, modifications that lower $T_m$ decrease potency while modifications that increase $T_m$ improve potency. One strategy to improve potency of ASOs is to employ a chimeric design where a low $T_m$, RNase H activating domain made of PS-modified DNA is flanked by end domains that contain 2'-modified sugars which confer high binding affinity but are not RNase H activating ("gapmer" design). One commonly employed strategy is to place five 2'-modified bases at the 5'-end, ten PS-modified DNA bases in the middle, and five 2'-modified bases at the 3'-end of the ASO (so called "5-10-5" design). A modification that confers nuclease resistance, increases binding affinity, and does not impair the reagent's ability to activate RNase H would be ideal. The present example demonstrates the utility of the internal napthylene-azo modifier to improve the nuclease stability and increase binding affinity of ASOs, enhancing their function as gene knockdown reagents.

Oligonucleotide Synthesis and Purification.

DNA, 2'OMe RNA, and LNA containing oligonucleotides were synthesized using solid phase phosphoramidite chemistry, deprotected and desalted on NAP-5 columns (Amersham Pharmacia Biotech, Piscataway, N.J.) according to routine techniques (Caruthers et al., 1992). The oligomers were purified using reversed-phase high performance liquid chromatography (RP-HPLC). The purity of each oligomer was determined by capillary electrophoresis (CE) carried out on a Beckman P/ACE MDQ system (Beckman Coulter, Inc., Fullerton, Calif.). All single-strand oligomers were at least 85% pure. Electrospray-ionization liquid chromatography mass spectrometry (ESI-LCMS) of the oligonucleotides was conducted using an Oligo HTCS system (Novatia, Princeton, N.J.), which consisted of ThermoFinnigan TSQ7000, Xcalibur data system, ProMass data processing software, and Paradigm MS4™ HPLC (Michrom BioResources, Auburn, Calif.). Protocols recommended by the manufacturers were followed. Experimental molar masses for all single-strand oligomers were within 1.5 g/mol of expected molar mass. These results confirm identity of the oligomers.

TABLE 9

Synthetic oligomers employed in Example 5 (anti-HPRT ASOs)

| SEQ ID NO: | Name | Sequence |
|---|---|---|
| 60 | HPRT#1 DNA | a t a g g a c t c c a g a t g t t t c c |
| 61 | HPRT#1 DNA 5'iFQ | a$_z$t a g g a c t c c a g a t g t t t c c |
| 62 | HPRT#1 DNA 3'iFQ | a t a g g a c t c c a g a t g t t t c$_z$c |
| 63 | HPRT#1 DNA 5' + 3'iFQ | a$_z$t a g g a c t c c a g a t g t t t c$_z$c |
| 64 | HPRT#1 DNA 5' + i + 3'iFQ | a$_z$t a g g a c t c c$_z$a g a t g t t t c$_z$c |
| 65 | HPRT#1 DNA PS | a*t*a*g*g*a*c*t*c*c*a*g*a*t*g*t*t*t*c*c |
| 66 | HPRT#1 DNA PS 5'iFQ | a$_z$t*a*g*g*a*c*t*c*c*a*g*a*t*g*t*t*t*c*c |
| 67 | HPRT#1 DNA PS 3'iFQ | a*t*a g*g*a*c*t*c*c*a*g*a*t*g*t*t*t*c$_z$c |
| 68 | HPRT#1 DNA PS 5' + 3'iFQ | a$_z$t*a*g*g*a*c*t*c*c*a*g*a*t*g*t*t*t*c$_z$c |
| 69 | HPRT#1 DNA PS 5' + I + 3'iFQ | a$_z$ta*g*g*a*c*t*c*c$_z$a*g*a*t*g*t*t*t*c$_z$c |
| 70 | HPRT#1 5-10-5 | A U A G G a c t c c a g a t g U U U C C |
| 71 | HPRT#1 5-10-5 2x iFQ | A$_z$U A G G a c t c c a g a t g U U U C$_z$C |
| 72 | HPRT#1 5-10-5 3x iFQ | A$_z$U A G G a c t c c$_z$a g a t g U U U C$_z$C |
| 73 | HPRT#1 5-10-5 PS | A*U*A*G*G*a*c*t*c*c*a*g*a*t*g*U*U*U*C*C |
| 74 | HPRT#1 5-10-5 PS 2x iFQ | A$_z$U*A*G*G*a*c*t*c*c*a*g*a*t*g*U*U*U*C$_z$C |
| 75 | HPRT#1 5-10-5 gapPS | A U A G G a*c*t*c*c*a*g*a*t*g*U U U C C |
| 76 | HPRT#1 5-10-5 gapPS 2x iFQ | A$_z$U A G G a*c*t*c*c*a*g*a*t*g*U U U C$_z$C |
| 77 | HPRT#1 5-10-5 gapPS 3x iFQ | A$_z$U A G G a*c*t*c*c$_z$a*g*a*t*g*U U U C$_z$C |
| 78 | HPRT#1 5-10-5 LNA PS | <u>A</u>*<u>U</u>*<u>A</u>*<u>G</u>*<u>G</u>*a*c*t*c*c*a*g*a*t*g*<u>U</u>*<u>U</u>*<u>U</u>*<u>C</u>*<u>C</u> |

Uppercase = 2'OMe RNA
Lowercase = DNA
Uppercase with underscore = LNA
"*" = phosphorothioate linkage
"z" = insertion of napthylene-azo modifier (iFQ)

HeLa Cell Culture, Transfections, and RT-qPCR Methods.

HeLa cells were split into 48-well plates and were transfected the next day at ~60% confluency in serum-free Dulbecco's Modified Eagle Medium (Invitrogen, Carlsbad, Calif.) using TriFECTin® (Integrated DNA Technologies, Coralville, Iowa) at a concentration of 2% (1 µL per 50 µL, OptiMEM® I) (Invitrogen, Carlsbad, Calif.) with ASOs at the indicated concentrations. All transfections were performed in triplicate. After 6 hours, media was exchanged with Dulbecco's Modified Eagle Medium containing 10% fetal bovine serum. RNA was prepared 24 hours after transfection using the SV96 Total RNA Isolation Kit (Promega, Madison, Wis.). cDNA was synthesized using 150 ng total RNA with SuperScript™-II Reverse Transcriptase (Invitrogen, Carlsbad, Calif.) per the manufacturer's instructions using both random hexamer and oligo-dT priming. Transfection experiments were all performed a minimum of three times.

Quantitative real-time PCR was performed using 10 ng cDNA per 10 µL reaction with Immolase™ DNA Polymerase (Bioline, Randolph, Mass.), 200 nM primers, and 200 nM probe. Hypoxanthine phosphoribosyltransferase 1 (HPRT1) (GenBank Acc. No. NM_000194) specific primers were:

```
HPRT-For
                                  (SEQ ID NO: 79)
5' GACTTTGCTTTCCTTGGTCAGGCA,

HPRT-Rev
                                  (SEQ ID NO: 80)
5' GGCTTATATCCAACACTTCGTGGG,
and probe HPRT-P
                                  (SEQ ID NO: 81)
5' MAX- ATGGTCAAGGTCGCAAGCTTGCTGGT-
IowaBlackFQ (IBFQ)
``` and were normalized to levels of an internal control gene, human acidic ribosomal Phosphoprotein PO(RPLP0) (GenBank Acc. No. NM_001002), which was measured in a multiplexed reaction using primers:

```
RPLP0-For
                                  (SEQ ID NO: 82)
5' GGCGACCTGGAAGTCCAACT,

RPLP0-Rev
                                  (SEQ ID NO: 83)
5' CCATCAGCACCACAGCCTTC,
and probe RPLP0-P
                                  (SEQ ID NO: 84)
5' FAM-ATCTGCTGCATCTGCTTGGAGCCCA-IBFQ
```

(Bieche et al., 2000, *Clin. Cancer Res.* 6(2): 452-59). Cycling conditions employed were: 95° C. for 10 minutes followed by 40 cycles of 2-step PCR with 95° C. for 15 seconds and 60° C. for 1 minute. PCR and fluorescence measurements were done using an ABI Prism™ 7900 Sequence Detector (Applied Biosystems Inc., Foster City, Calif.). All reactions were performed in triplicate. Expression data were normalized. Copy number standards were multiplexed using linearized cloned amplicons for both the HPRT and RPLP0 assays. Unknowns were extrapolated against standards to establish absolute quantitative measurements.

Results.

Figure 5:
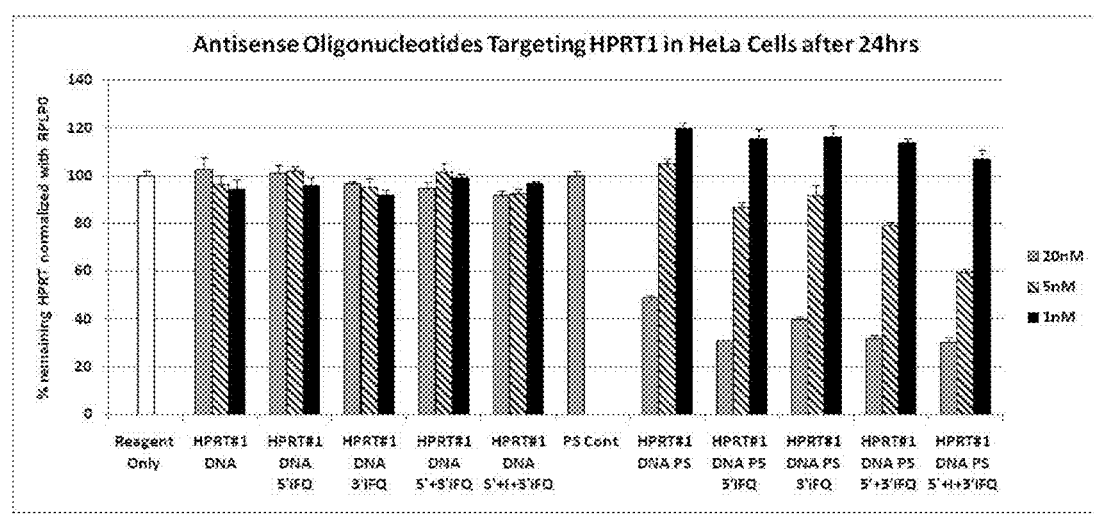
FIG. 5 illustrates knockdown of HPRT expression by DNA ASOs, with or without PS bonds or iFQ modification. ASOs were transfected into HeLa cells and RNA was prepared 24 hours post transfection. Relative HPRT levels were assessed by RT-qPCR and are reported on the Y-axis.

ASOs were transfected into HeLa cells at 1 nM, 5 nM, and 20 nM concentrations. RNA was prepared 24 hours post transfection, converted to cDNA, and HPRT expression levels were measured using qPCR. Results are shown in FIG. 5 for the set of anti-HPRT ASOs made from DNA bases. Unmodified single-stranded DNA oligos are rapidly degraded by exonucleases and endonucleases. No knockdown of HPRT was observed using this design (HPRT DNA), presumably due to rapid degradation of the unprotected compound. ASOs with a single iFQ modification near the 3'-end (HPRT DNA 3'iFQ), a single iFQ modification near the 5'-end (HPRT DNA 5'iFQ), two iFQ modifications inserted near both ends (HPRT DNA 5'+3'iFQ), and three iFQ modifications inserted in the center and near both ends (HPRT DNA 5'+I+3'iFQ) were also tested and similarly showed no functional gene knockdown at the doses examined. Therefore, the addition of even up to 3 iFQ modifications does not provide sufficient nuclease stabilization to permit otherwise unmodified DNA oligos to function as antisense gene-knockdown agents.

The same series of oligonucleotides was synthesized having phosphorothioate (PS) internucleotide bonds throughout the sequence (except where the phosphate connects to an iFQ modifier). Historically, DNA-PS oligos were among the first effective antisense compounds studied. This modification increases nuclease stability; however, it also lowers binding affinity (TO and as a result this so-called "first generation" antisense chemistry usually shows relatively low potency. The "DNA-PS" ASO reduced HPRT levels by 50% at 20 nM concentration; however, no reduction in HPRT levels was observed at lower doses. Addition of the iFQ modification, which increases binding affinity and blocks exonuclease action, improved function of the DNA-PS ASOs. The "DNA-PS 5'+I+3'iFQ" compound showed the best results within this series, with HPRT knockdown of 70% at 20 nM and 40% at 5 nM observed (FIG. 5).

Figure 6:
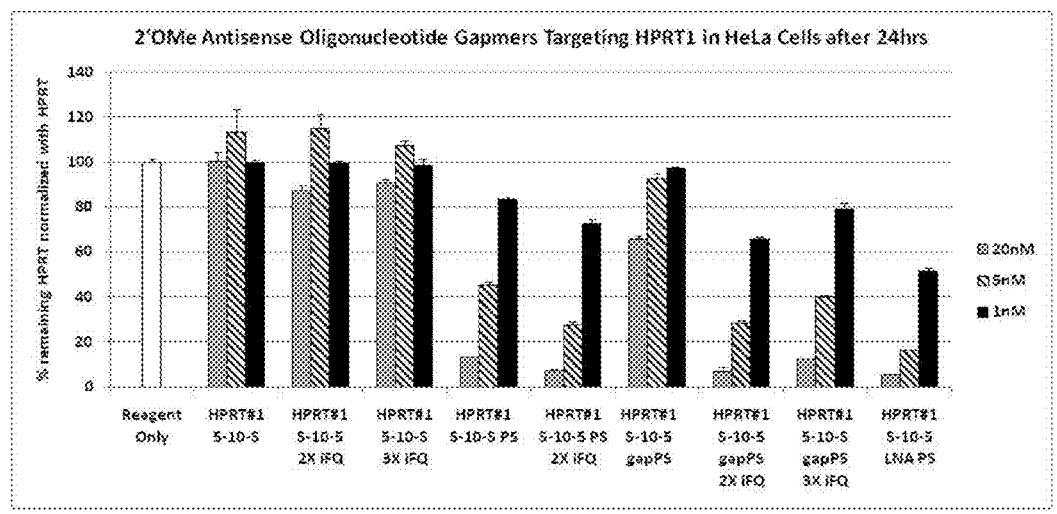
FIG. 6 illustrates knockdown of HPRT expression by chimeric "gapmer" ASOs, with or without PS bonds and with or without iFQ modification. ASOs were transfected into HeLa cells and RNA was prepared 24 hours post transfection. Relative HPRT levels were assessed by RT-qPCR and are reported on the Y-axis.

A second set of ASOs was synthesized using a chimeric "5-10-5 gapmer" design where five base end domains were made of 2'OMe RNA and a central ten base RNase H active domain were made of DNA. Oligonucleotides had zero, one, two, or three iFQ modifiers inserted at the same positions as the DNA ASOs in FIG. 5. These oligonucleotides were transfected into HeLa cells as before and HPRT mRNA levels were examined 24 hours post-transfection. Results are shown in FIG. 6. The three gapmer ASOs with a phosphodiester DNA central domain showed no activity in reducing HPRT mRNA levels, regardless of whether the sequence was modified with the iFQ group or not ("5-10-5", 5-10-5 2×iFQ" and "5-10-5 3×iFQ"). The same sequence fully PS modified ("5-10-5-PS") showed good potency with 75% knockdown of HPRT at 20 nM concentration. The addition of two iFQ groups near the ends of this design ("5-10-5-PS 2×iFQ") showed the best potency of this set, with >90% knockdown of HPRT at 20 nM and >70% knockdown at 5 nM concentration.

Although 2'OMe RNA is somewhat resistant to endonuclease attack, gapmer ASOs of this design are usually made with full PS modification to prevent exonuclease degradation. Consistent with this idea, an ASO with the DNA domain protected by PS internucleotide linkages but having phosphodiester bonds in the 2'OMe flanking domains showed no gene knockdown activity ("5-10-5 gapPS"). Use of the iFQ modification at the ends, however, permits use of this new design by providing protection from exonuclease attack; this new design should also increase binding affinity and lower toxicity by reducing PS content. This strategy was effective and the ASO ("5-10-5 gapPS 2×iFQ") showed knockdown of HPRT levels by >90% at 20 nM and by >70% at 5 nM. Potency was very similar to the full PS modified ASO. This design is expected to have reduced toxicity; however, toxicity is not easily tested in this system as HeLa cells are tolerant to fairly high doses of PS modified oligonucleotides. Benefit from reduced PS content will be better appreciated in vivo.

Although it did not increase functional potency, addition of a third centrally placed iFQ group ("5-10-5 gapPS-3×-iFQ") was compatible with gene knockdown in this RNase H active antisense design. It is generally accepted that maximal activity of RNase H active ASOs requires a DNA domain having at least 8 uninterrupted DNA residues. It was unexpected that the 3×iFQ design (where the 10 base DNA domain is interrupted by a central iFQ group) would work without reducing potency compared with the 2×iFQ design (where the 10 base DNA domain is continuous). It is possible that unique properties of the iFQ group allow its insertion to remain compatible with RNase H activity, possibly due to the same postulated base stacking interactions that result in increased $T_m$ in these compounds.

The most potent antisense design in current use are LNA-modified gapmers, where very strong $T_m$ enhancing LNA modifications are used in the flanking domains in place of the 2'OMe RNA bases used in the present example. While potent, this design is expensive and can show significant toxicity in certain contexts. The same anti-HPRT sequence was made as an LNA 5-10-5 gapmer (fully PS modified). As expected, this compound showed the highest relative potency of any of the ASOs tested ("5-10-5 LNA PS") but the observed potency was only marginally higher than the best of the iFQ compositions ("5-10-5-PS 2×iFQ"). The very high binding affinity LNA reagents usually result in decreased specificity, so use of the iFQ designs of the present invention may show improved specificity at a small cost in potency.

Example 6

This example demonstrates use of the iFQ modification in RNA duplexes with application in suppressing gene expression via an RNAi mechanism of action.

The use of double-stranded RNA (dsRNA) to trigger gene suppression via RNA interference (RNAi) is a well-described technique. Synthetic dsRNAs that mimic natural cellular products (small interfering RNAs, or siRNAs) are usually 21 bases long with a central 19 base duplex domain with 2-base 3'-overhangs. Alternatively, slightly larger synthetic oligonucleotides can be used that are substrates for the cytoplasmic nuclease Dicer, which processes these species into 21-mer siRNAs. Typically these reagents are asymmetric and have a 25 base top (Sense strand, "S") and a 27 base bottom strand (Antisense strand, "AS") with a single 2-base 3'-overhang on the AS strand. These longer siRNAs are called Dicer-substrate siRNAs, or DsiRNAs. Although dsRNA is far more stable to nuclease attack than single-stranded RNA (ssRNA), degradation of the synthetic siRNAs can significantly limit potency of the compounds, especially when used in vivo. Incorporation of chemical modifications, such as 2'OMe RNA, 2'F RNA, or LNA bases, improves nuclease stability and can improve function of the siRNA. Selective placement of nuclease-resistant phosphorothioate bonds (PS) can also help stabilize the siRNA, especially when used near the terminal 3'-internucleotide linkages. Unfortunately, careful placement of modified groups is essential as extensive chemical modification usually lowers functional potency of the compound even though nuclease stabilization has been achieved, probably through disrupting interaction of the RNA duplex with key protein mediators of RNAi, like Dicer or Ago2.

The present example demonstrates that the iFQ modifier can be introduced into DsiRNAs. Like other chemical modifiers, iFQ insertion can lead to increased potency, decreased potency, or no change in potency depending upon placement.

Oligonucleotide Synthesis and Purification.

RNA and modified RNA oligonucleotides were synthesized using solid phase phosphoramidite chemistry, deprotected and desalted according to routine techniques (Caruthers et al., 1992). The oligomers were purified using ion-exchange high performance liquid chromatography (IE-HPLC) and were handled under RNase-free conditions. All RNA oligonucleotides were prepared as a sodium salt. The purity of each oligomer was determined by capillary electrophoresis (CE) carried out on a Beckman P/ACE MDQ system (Beckman Coulter, Inc., Fullerton, Calif.). All single-strand oligomers were at least 85% pure. Electrospray-ionization liquid chromatography mass spectrometry (ESI-LCMS) of the oligonucleotides was conducted using an Oligo HTCS system (Novatia, Princeton, N.J.), which consisted of ThermoFinnigan TSQ7000, Xcalibur data system, ProMass data processing software, and Paradigm MS4™ HPLC (Michrom BioResources, Auburn, Calif.). Protocols recommended by the manufacturers were followed. Experimental molar masses for all single-strand oligomers were within 1.5 g/mol of expected molar mass. These results confirm identity of the oligomers.

Duplexes were formed by mixing equal molar amounts of the top and bottom strands in 30 mM Hepes, pH 7.5, 100 mM potassium acetate, heating at 95° C. for 2 minutes, then cooling to room temperature. Table 10 lists the duplexes synthesized for Example 6.

TABLE 10

Synthetic RNA duplexes employed in Example 6 (anti-HPRT DsiRNAs)

| SEQ ID NO: | Name | Sequence | |
|---|---|---|---|
| 85 | NCI Negative | 5' CGUUAAUCGCGUAUAAUACGCGUat 3' | S |
| 86 | Control | 3' CAGCAAUUAGCGCAUAUUAUGCGCAUA 5' | AS |
| 87 | HPRT | 5' GCCAGACUUUGUUGGAUUUGAAAtt 3' | S |
| 88 | unmod | 3' UUCGGUCUGAAACAACCUAAACUUUAA 5' | AS |
| 89 | HPRT | 5' GCCAGACUUUGUUGGAUUUGAAAtt 3' | S |
| 90 | iFQ v1 | 3' U$^Z$UCGGUCUGAAACAACCUAAACUUUAA 5' | AS |
| 91 | HPRT | 5' G$^Z$CCAGACUUUGUUGGAUUUGAAAtt 3' | S |
| 92 | iFQ v2 | 3' UUC GGUCUGAAACAACCUAAACUUUAA 5' | AS |
| 93 | HPRT | 5' G$^Z$CCAGACUUUGUUGGAUUUGAAAt$^Z$t 3' | S |
| 94 | iFQ v3 | 3' UUC GGUCUGAAACAACCUAAACUUUA A 5' | AS |
| 95 | HPRT | 5' G CCAGACUUUGUUGGAUUUGAAAtt 3' | S |
| 96 | iFQ v4 | 3' UUC$^Z$GGUCUGAAACAACCUAAACUUUAA 5' | AS |
| 97 | HPRT | 5' G CCAGACUUUGUUGGAUUUGAAA t 3' | S |
| 98 | iFQ v5 | 3' UUC$^Z$GGUCUGAAACAACCUAAACUUUA$^Z$A 5' | AS |
| 99 | HPRT | 5' G$^Z$CCAGACUUUGUUGGAUUUGAAAt$^Z$t 3' | S |
| 100 | iFQ v6 | 3' UUC$^Z$GGUCUGAAACAACCUAAACUUUA A 5' | AS |

TABLE 10-continued

Synthetic RNA duplexes employed in Example 6 (anti-HPRT DsiRNAs)

| SEQ ID NO: | Name | Sequence | |
|---|---|---|---|
| 101 | HPRT | 5' G^zCCAGACUUUGUUGGAUUUGAAAt^zt 3' | S |
| 102 | iFQ v7 | 3' UUC^zGGUCUGAAACAACCUAAACUUUA^zA 5' | AS |

Uppercase = RNA
Lowercase = DNA
"z" = insertion of napthylene-azo modifier (iFQ)
Note:
gaps have been introduced in sequences for the purpose of alignment only and do not represent any modification to sequence.

HeLa Cell Culture, Transfections, and RT-qPCR Methods.

HeLa cells were transfected in "reverse format" at ~60% confluency (Invitrogen, Carlsbad, Calif.) using 1 µL Lipofectamine™ RNAiMAX per 50 µL OptiMEM™ I (Invitrogen, Carlsbad, Calif.) with RNA duplexes at the indicated concentrations. All transfections were performed in triplicate. RNA was prepared 24 hours after transfection using the SV96 Total RNA Isolation Kit (Promega, Madison, Wis.); cDNA was synthesized using 150 ng total RNA with SuperScript™-II Reverse Transcriptase (Invitrogen, Carlsbad, Calif.) per the manufacturer's instructions using both random hexamer and oligo-dT priming.

Quantitative real-time PCR reactions were done using 10 ng cDNA per 10 µL reaction, Immolase™ DNA Polymerase (Bioline, Randolph, Mass.), 500 nM primers, and 250 nM probe. Hypoxanthine phosphoribosyltransferase 1 (HPRT1) (GenBank Acc, No. NM_000194) specific primers were:

```
HPRT-For
                                    (SEQ ID NO: 79)
5' GACTTTGCTTTCCTTGGTCAGGCA,

HPRT-Rev
                                    (SEQ ID NO: 80)
5' GGCTTATATCCAACACTTCGTGGG,
and probe HPRT-P
                                    (SEQ ID NO: 81)
5' FAM- ATGGTCAAGGTCGCAAGCTTGCTGGT-
IowaBlackFQ (IBFQ).
```

Cycling conditions employed were: 95° C. for 10 minutes followed by 40 cycles of 2-step PCR with 95° C. for 15 seconds and 60° C. for 1 minute. PCR and fluorescence measurements were done using an ABI Prism™ 7900 Sequence Detector (Applied Biosystems Inc., Foster City, Calif.). All data points were performed in triplicate. Expression data were normalized to levels of an internal control gene, human splicing factor, arginine/serine-rich 9 (SFRS9) (GenBank Acc. No. NM_003769), which was measured in a multiplexed reaction using primers: SFRS9-For 5' TGT-GCAGAAGGATGGAGT (SEQ ID NO: 103), SFRS9-Rev 5' CTGGTGCTTCTCTCAGGATA (SEQ ID NO: 104), and probe SFRS9-P 5' MAX-TGGAATATGCCCTGCG-TAAACTGGA-IBFQ (SEQ ID NO: 105), setting the baseline to cells transfected with a scrambled negative control RNA duplex (NC1). Copy number standards were run in parallel using linearized cloned amplicons for both the HPRT and SFRS9 assays. Unknowns were extrapolated against standards to establish absolute quantitative measurements.

Results.

Figure 7:
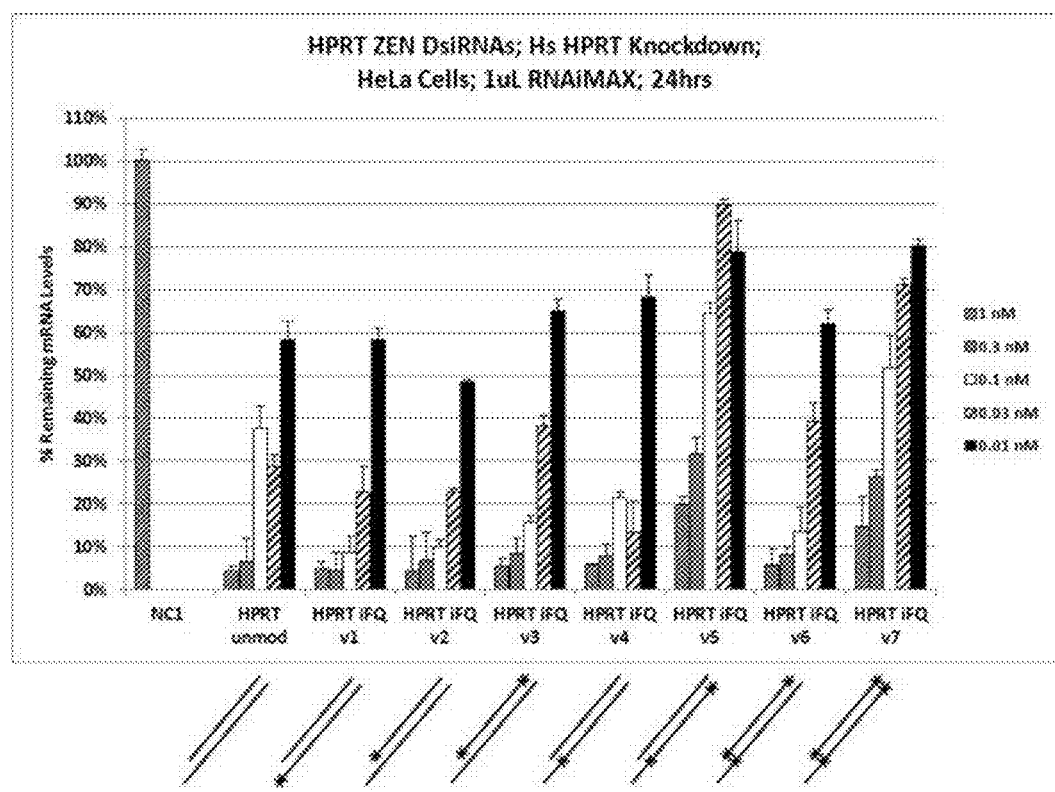
FIG. 7 illustrates knockdown of HPRT using DsiRNAs at doses ranging from 0.01 nM to 1.0 nM. DsiRNAs were modified with iFQ group(s) at positions within the duplexes as indicated in the schematic below the graph. DsiRNAs were transfected into HeLa cells and RNA was prepared 24 hours post transfection. Relative HPRT levels were assessed by RT-qPCR and are reported on the Y-axis.

The anti-HPRT DsiRNA employed in the present study is extremely potent and typically shows detectable knockdown of target mRNA at low picomolar levels. Consistent with this expectation, the unmodified duplex reduced HPRT levels by ~40% at a 10 pM dose at 24 hours post-transfection in HeLa cells. A series of modified duplexes containing the iFQ group positioned at various locations in the S strand, AS strand, or both were similarly transfected into HeLa cells and HPRT mRNA levels were measured 24 hour post-transfection. Results are shown in FIG. 7.

Placing the iFQ group near the 3'-end of the AS strand was well tolerated; insertion between bases 1 and 2 from the 3'-end (in the single-stranded 3'-overhang domain) (duplex HPRT iFQ v1) or between bases 3 and 4 from the 3'-end (at the start of the duplex domain) (duplex HPRT iFQ v4) showed similar potency to the unmodified duplex. Placing the iFQ group near the 5'-end of the S strand was similarly well tolerated (duplex HPRT iFQ v2) as was placing the iFQ group near both ends of the S strand (duplex HPRT iFQ v3). In contrast, duplexes having an iFQ group near the 5'-end of the AS strand showed reduced potency (duplexes HPRT iFQ v5 and v7), so modification at this position should be avoided.

Within the error of the system studied, the iFQ modified and unmodified duplexes showed similar potency (except for those duplexes modified at the 5'-end of the AS strand, as noted above). Benefit from the iFQ group is most likely to be evident in settings where nuclease stabilization is needed, which is not appreciated in the present in vitro system, but based on the results of Examples 1 and 2, greater benefit would be expected from use of this modification when used in vivo where exposure to serum nucleases is more problematic.

Example 7

This example demonstrates decreased cellular toxicity from lipid transfected internal napthylene-azo-containing oligomers compared with other compounds.

Toxicity from chemical modification of synthetic oligomers can be problematic as it can give unwanted side effects, cause unreliable results, and limit therapeutic utility of the oligomer. Cellular death can result from toxic chemical modifications by inducing necrosis or apoptosis. Toxicity was ascertained with oligomers containing a non-targeting, negative control ("NC1") sequence using chemical modification patterns employed in the AMOs examined in Examples 3 and 4 (see Table 11). Generalized cytotoxicity (from necrosis and/or apoptosis) was measured by quantifying the relative number of live and dead cells after treatment with the chemically modified oligomers, while cytotoxicity resulting from the induction of the apoptotic pathway was determined by measuring the levels of caspase-3 and -7 after oligomer treatment.

Oligonucleotide Synthesis and Preparation.

DNA oligonucleotides were synthesized using solid phase phosphoramidite chemistry, deprotected and desalted on NAP-5 columns (Amersham Pharmacia Biotech, Piscataway, N.J.) according to routine techniques (Caruthers et al., 1992). The oligomers were purified using reversed-phase high performance liquid chromatography (RP-HPLC). The purity of each oligomer was determined by capillary electrophoresis (CE) carried out on a Beckman P/ACE MDQ system (Beckman Coulter, Inc., Fullerton, Calif.). All single-strand oligomers were at least 90% pure. Electrospray-ionization liquid chromatography mass spectrometry (ESI- LCMS) of the oligonucleotides was conducted using an Oligo HTCS system (Novatia, Princeton, N.J.), which consisted of ThermoFinnigan TSQ7000, Xcalibur data system, ProMass data processing software, and Paradigm MS4™ HPLC (Michrom BioResources, Auburn, Calif.). Protocols recommended by the manufacturers were followed. Experimental molar masses for all single-strand oligomers were within 1.5 g/mol of expected molar mass. These results confirm identity of the oligomers.

internal normalizing control providing data independent of cell number, and a reduction of live/dead cells correlates with cytotoxicity. The "2'OMe 5'+3' iFQ" and "2'OMe PSends" compounds are the least toxic oligomers and there is minimal toxicity even at the high 100 nM dose. The "DNA/PS" oligomer, which is entirely comprised of PS linkages, shows substantial cell death at both doses suggesting that PS modification is toxic to the cells. When LNA bases are incorporated into the NC1 AMO, such as in the

TABLE 11

Synthetic oligomers employed in Example 7 (NC1 AMOs)

| SEQ ID NO: | Name | Sequence |
|---|---|---|
| 106 | 2'OMe 5' + 3' iFQ | G$_z$C G U A U U A U A G C C G A U U A A C G$_z$A |
| 107 | 2'OMe PSends | G*C*G*U A U U A U A G C C G A U U A A*C*G*A |
| 108 | DNA/PS | g*c*g*t*a*t*t*a*t*a*g*c*c*g*a*t*t*a*a*c*g*a |
| 109 | DNA/LNA PO | g C g t A t t A t a G c c G a t T a a C g a |
| 110 | DNA/LNA PS | g*C*g*t*A*t*t*A*t*a*G*c*c*G*a*t*T*a*a*C*g*a |
| 111 | 2'OMe/LNA PO | G C G T A T T A T A G C C G A T T A A C G A |
| 112 | 2'OMe/LNA PS | G*C*G*T*A*T*T*A*T*A*G*C*C*G*A*T*T*A*A*C*G*A |

Uppercase = 2'OMe RNA
Lowercase = DNA
Uppercase with underscore = LNA
"*" = phosphorothioate linkage
"z" = napthylene-azo modifier (iFQ)

Cell Culture, Transfections, and Luciferase Assays.

HeLa cells were plated in 48-well plates in DMEM containing 10% FBS to achieve 90% confluency the next day. The following morning, NC1 AMOs were transfected at 100 nM or 50 nM concentrations in triplicate wells in two sets (one for measuring general cytotoxicity, one for measuring apoptosis induction) with 1 μl TriFECTin® (Integrated DNA Technologies) per well in DMEM containing 10% FBS. An apoptosis-inducing agent, Staurosporine (1 mM in DMSO), was incubated at 1 μM on the cells for 24 hours as a positive control. After 24 hours of NC1 AMO treatment, the first set of cells was analyzed for viability using the MultiTox-Glo Multiplex Cytotoxicity Assay (Promega, Madison, Wis.) with the peptide-substrate GF-AFC (glycyl-phenylalanylaminofluorocoumarin), which generates a fluorescence signal upon cleavage by a "live-cell" specific protease, measured at 405 $nm_{Ex}$/505 $nm_{Em}$ in a SpectraFluor Microplate Reader (Tecan Group Ltd, Mannedorf, Switzerland). Continuing to use the MultiTox-Glo Multiplex Cytotoxicity Assay, the same cells were subsequently analyzed for cytotoxicity by detecting a "dead-cell" protease activity in a luciferase-based assay measured on a GloMax® 96 Microplate Luminometer (Promega) per the manufacturer's recommendations. To assess cytotoxicity derived from induction of the apoptosis pathway, the Caspase-Glo® 3/7 Assay (Promega) was performed with the second set of cells to measure caspase-3 and -7 levels according to the manufacturer's recommendations on a GloMax® 96 Microplate Luminometer (Promega).

Results.

Figure 8:
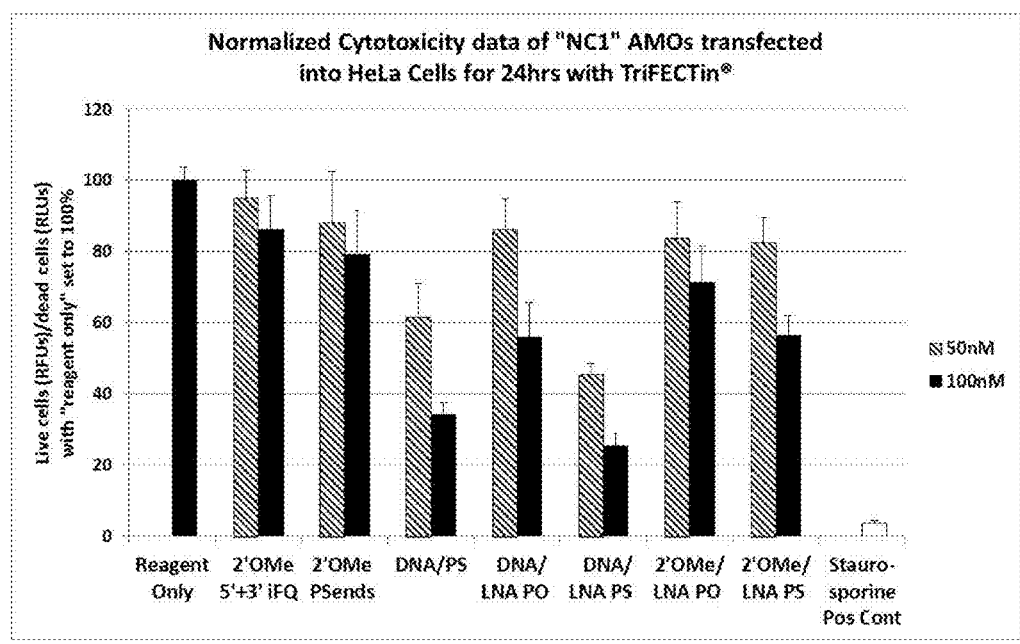
FIG. 8 illustrates the toxicity profiles of various AMO chemistries when transfected for 24 hours at 50 nM or 100 nM in HeLa cells. The negative control or "NC1" sequence is not predicted to target any known human miRNAs or mRNAs, and so toxicity effects should be specific to the chemical composition of the oligonucleotide. The MultiTox-Glo Multiplex Cytotoxicity Assay was employed to measure cell viability following treatment with various chemically modified oligonucleotides (X-axis), and cell viability was calculated as a ratio of live/dead cells to normalize the data independent of cell number (Y-axis). A decrease of live/dead cell values correlates with decreased cell viability.

For the cytoxocity analysis graphed in FIG. 8, data is presented as a ratio of live/dead cells as calculated from the abundance of "live-cell" and "dead-cell" proteases described above. The ratio of live/dead cells serves as an "DNA/LNA PO" oligomer, cell death is seen at the high 100 nM dose suggesting that LNA modification is toxic to the cells. Importantly, additive cell death is seen after combining these two chemistries in the "DNA/LNA PS" oligomer, demonstrating toxicity which also correlates with the dysmorphic, unhealthy cells seen during the visual analysis at the time the assay was performed. Substituting DNA with 2'OMe bases in the "2'OMe/LNA PO" and "2'OMe/LNA PS" NC1 AMOs reduces toxicity compared with their DNA counterparts; however, cell death is still seen at the 100 nM dose.

Figure 9:
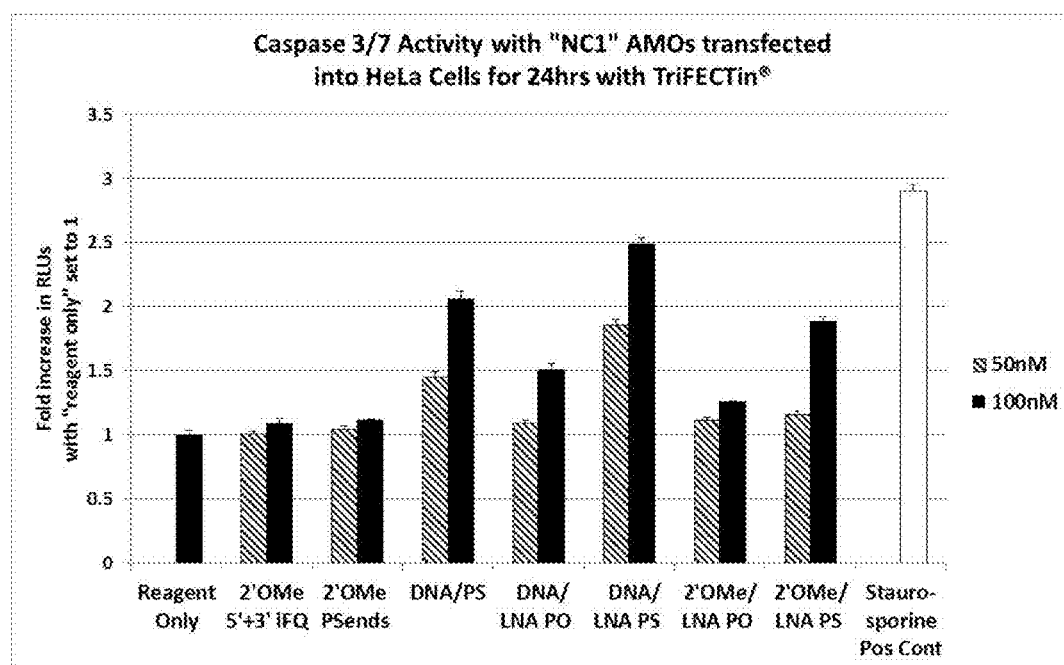
FIG. 9 illustrates apoptosis induction profiles caused by various AMO chemistries when transfected for 24 hours at 50 nM or 100 nM in HeLa cells. The negative control or "NC1" sequence is not predicted to target any known human miRNAs or mRNAs, and so induction of apoptosis should be specific to the biological effects of chemical composition of the oligonucleotide in the cell. The Caspase-Glo 3/7 Assay was employed to measure the levels of caspase-3 and caspase-7, which are known effectors of apoptosis, using a luciferase assay. Apoptosis induction following treatment with various chemically modified oligonucleotides (X-axis) is proportional to increasing levels of luminescence (Y-axis).

In parallel, HeLa cells treated with the NC1 AMOs were assessed for apoptosis induction by evaluating the levels of caspase-3 and -7 in a luciferase-based assay (FIG. 9). Luminescence is proportional to the abundance of the apoptosis effectors and an increase in RLUs correlates with an increase in apoptosis. The data in FIG. 9 mirrors the cytotoxicity profiles from the NC1 AMOs assayed in FIG. 8. The NC1 AMOs that do not trigger apoptosis are the "2'OMe 5'+3' iFQ" and "2'OMe PSends" compounds. Both extensive PS modification ("DNA/PS") and incorporation of LNA bases ("DNA/LNA PO") induce apoptosis, while an additive effect is seen when these two chemistries are combined ("DNA/LNA PS"). Again, substitution of DNA bases for 2'OMe bases ("2'OMe/LNA PO" and "2'OMe/LNA PS") reduces apoptosis induction. However, the "2'OMe/LNA PS" still demonstrates apoptosis induction at the 100 nM dose.

This cytotoxicity profiling analysis clearly exemplifies that certain chemical modification strategies can be detrimental to cell viability. The "2'OMe 5'+3' iFQ" AMO and the "DNA/LNA PS" AMOs, which demonstrated similar high potency in Example 3, have significantly different toxicity profiles. The "2'OMe 5'+3' iFQ" oligomer was non-toxic in this system, and the "DNA/LNA PS" oligomer caused substantial cell death in FIG. 8 and was shown to induce apoptosis in FIG. 9. These data confirm the superiority of the "2'OMe 5'+3' iFQ" AMO when compared to other standard AMOs with comparable potency (Example 3), increased specificity (Example 4), and reduced toxicity.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An antisense oligonucleotide comprising at least one modification that is incorporated between two bases of the antisense oligonucleotide, wherein the modification increases binding affinity and nuclease resistance of the antisense oligonucleotide, and wherein the modification has the structure:

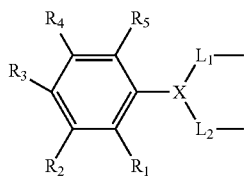

wherein
X is a nitrogen or carbon atom, wherein if X is a carbon atom, the fourth substituent attached to the carbon atom can be hydrogen or a C1-C8 alkyl group;
the linking groups $L_1$ and $L_2$ positioning the modification at an internal position of the oligonucleotide are independently alkyl, alkynyl, alkenyl, heteroalkyl, substituted alkyl, aryl, heteroaryl, substituted aryl, cycloalkyl, alkylaryl, or alkoxy; and
$R_1$-$R_5$ are independently hydrogen, alkyl, alkynyl, alkenyl, heteroalkyl, substituted alkyl, aryl, heteroaryl, substituted aryl, cycloalkyl, alkylaryl, alkoxy, an electron withdrawing group, an electron donating group, an attachment point for a ligand, or

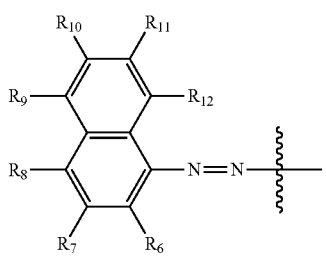

wherein
$R_6$, $R_7$, $R_9$-$R_{12}$ are independently hydrogen, alkyl, alkynyl, alkenyl, heteroalkyl, substituted alkyl, aryl, heteroaryl, substituted aryl, cycloalkyl, alkylaryl, alkoxy, an electron withdrawing group, or an electron donating group; and
$R_8$ is hydrogen, alkyl, alkynyl, alkenyl, heteroalkyl, substituted alkyl, aryl, heteroaryl, substituted aryl, cycloalkyl, alkylaryl, alkoxy, or an electron withdrawing group.

2. The antisense oligonucleotide of claim 1, wherein the modification is located within three bases of a terminal nucleotide.

3. The antisense oligonucleotide of claim 1, wherein the modification is located between a terminal base and a penultimate base of either the 3' or the 5' end of the antisense oligonucleotide.

4. The antisense oligonucleotide of claim 1, wherein the modification is located between the terminal base and the penultimate base at both the 3' and the 5' ends of the antisense oligonucleotide.

5. The antisense oligonucleotide of claim 1, wherein the modification is a napthylene-azo compound.

6. The antisense oligonucleotide of claim 1, wherein the modification has the structure:

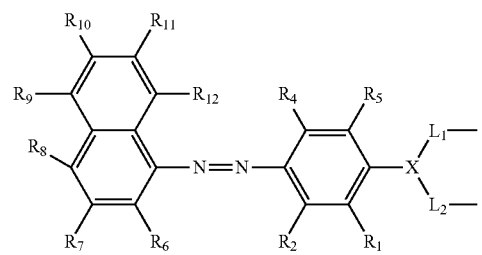

wherein
the linking groups $L_1$ and $L_2$ positioning the modification at an internal position of the oligonucleotide are independently alkyl, alkynyl, alkenyl, heteroalkyl, substituted alkyl, aryl, heteroaryl, substituted aryl, cycloalkyl, alkylaryl, or alkoxy;
$R_1$, $R_2$, $R_4$, $R_5$ are independently hydrogen, alkyl, alkynyl, alkenyl, heteroalkyl, substituted alkyl, aryl, heteroaryl, substituted aryl, cycloalkyl, alkylaryl, alkoxy, an electron withdrawing group, or an electron donating group;

R$_6$, R$_7$, R$_9$-R$_{12}$ are independently hydrogen, alkyl, alkynyl, alkenyl, heteroalkyl, substituted alkyl, aryl, heteroaryl, substituted aryl, cycloalkyl, alkylaryl, alkoxy, an electron withdrawing group, or an electron donating group;

R$_8$ is hydrogen, alkyl, alkynyl, alkenyl, heteroalkyl, substituted alkyl, aryl, heteroaryl, substituted aryl, cycloalkyl, alkylaryl, alkoxy, or an electron withdrawing group; and X is a nitrogen or carbon atom, wherein if X is a carbon atom, the fourth substituent attached to the carbon atom can be hydrogen or a C1-C8 alkyl group.

7. The antisense oligonucleotide of claim 6, wherein R$_8$ is an electron withdrawing group, which is NO$_2$.

8. The antisense oligonucleotide of claim 1, wherein the modification has the structure:

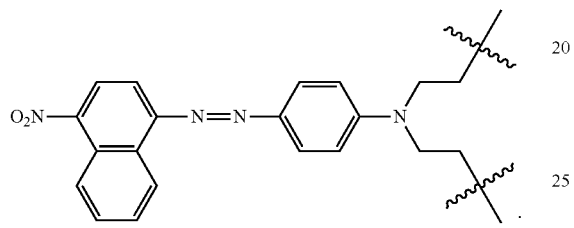

9. The antisense oligonucleotide of claim 1, wherein the antisense oligonucleotide further comprises at least one 2'-O-methyl RNA.

10. The antisense oligonucleotide of claim 1, wherein the antisense oligonucleotide further comprises one or more phosphorothioate linkages.

11. The antisense oligonucleotide of claim 1, wherein the antisense oligonucleotide comprises a region of bases linked through phosphodiester bonds, wherein the region is flanked at one or both ends by regions containing phosphorothioate linkages.

12. An antisense oligonucleotide having the structure:

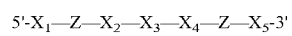

wherein:

X$_1$ and X$_5$ are independently 1-3 nucleotides;

the internucleotide linkages are optionally phosphorothioate;

Z is a napthylene-azo compound;

X$_2$ and X$_4$ are independently 1-5 nucleotides wherein the internucleotide linkages are optionally phosphorothioate; and X$_3$ is 10-25 nucleotides.

\* \* \* \* \*

UNITED STATES PATENT AND TRADEMARK OFFICE
CERTIFICATE OF CORRECTION

PATENT NO. : 9,506,059 B2  
APPLICATION NO. : 14/281646  
DATED : November 29, 2016  
INVENTOR(S) : Mark Aaron Behlke et al.

Page 1 of 1

It is certified that error appears in the above-identified patent and that said Letters Patent is hereby corrected as shown below:

On the Title Page

At item (22), delete "Sep. 26, 2014" and insert --May 19, 2014--, therefor.

Signed and Sealed this  
Ninth Day of May, 2017

Michelle K. Lee  
*Director of the United States Patent and Trademark Office*

SEQUENCE LISTING

```
<160> NUMBER OF SEQ ID NOS: 112

<210> SEQ ID NO 1
<211> LENGTH: 10
<212> TYPE: DNA
<213> ORGANISM: Artificial Sequence
<220> FEATURE:
<223> OTHER INFORMATION: Sythetic

<400> SEQUENCE: 1
atcgttgcta                                                          10

<210> SEQ ID NO 2
<211> LENGTH: 10
<212> TYPE: DNA
<213> ORGANISM: Artificial Sequence
<220> FEATURE:
<223> OTHER INFORMATION: Synthetic

<400> SEQUENCE: 2
tagcaacgat                                                          10

<210> SEQ ID NO 3
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: iFQ is inserted between nucleotide positions 3
      and 4.

<400> SEQUENCE: 3
atcgttgcta                                                          10

<210> SEQ ID NO 4
<211> LENGTH: 10
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (4)..(5)
<223> OTHER INFORMATION: iFQ is inserted between nucleotide positions 4
      and 5.

<400> SEQUENCE: 4
atcgttgcta                                                                  10

<210> SEQ ID NO 5
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: iFQ is inserted between nucleotide positions 5
      and 6.

<400> SEQUENCE: 5
atcgttgcta                                                                  10

<210> SEQ ID NO 6
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.

<400> SEQUENCE: 6
atcgttgcta                                                                  10

<210> SEQ ID NO 7
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: iFQ is inserted between nucleotide positions 9
      and 10.

<400> SEQUENCE: 7
atcgttgcta                                                                  10

<210> SEQ ID NO 8
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: iSpC3 is inserted between nucleotide positions
      3 and 4.

<400> SEQUENCE: 8
atcgttgcta                                                                  10
```

```
<210> SEQ ID NO 9
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: iSpC3 is inserted between nucleotide positions
      4 and 5.

<400> SEQUENCE: 9
atcgttgcta                                                            10

<210> SEQ ID NO 10
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: iSpC3 is inserted between nucleotide positions
      5 and 6.

<400> SEQUENCE: 10
atcgttgcta                                                            10

<210> SEQ ID NO 11
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: iFQ is inserted between nucleotide positions 3
      and 4.

<400> SEQUENCE: 11 atcttgcta                                                              9

<210> SEQ ID NO 12
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: iSpC3 is inserted between nucleotide positions
      3 and 4.

<400> SEQUENCE: 12 atcttgcta                                                              9

<210> SEQ ID NO 13
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
```

```
<223> OTHER INFORMATION: iFQ is inserted between nucleotide positions 4
      and 5.

<400> SEQUENCE: 13
atcgttgcta                                                          10

<210> SEQ ID NO 14
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: iSpC3 is inserted between nucleotide positions
      4 and 5.

<400> SEQUENCE: 14
atcgttgcta                                                          10

<210> SEQ ID NO 15
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: iFQ is inserted between nucleotide positions 4
      and 5.

<400> SEQUENCE: 15 atcgtgcta                                                            9

<210> SEQ ID NO 16
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: iSpC3 is inserted between nucleotide positions
      4 and 5.

<400> SEQUENCE: 16 atcgtgcta                                                            9

<210> SEQ ID NO 17
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: iFQ is inserted between nucleotide positions 5
      and 6.

<400> SEQUENCE: 17
atcgttgcta                                                          10

<210> SEQ ID NO 18
<211> LENGTH: 10
<212> TYPE: DNA
```

<210> SEQ ID NO 18
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: iSpC3 is inserted between nucleotide positions 5 and 6.

<400> SEQUENCE: 18
atcgttgcta                                                              10

<210> SEQ ID NO 19
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: iFQ is inserted between nucleotide positions 5 and 6.

<400> SEQUENCE: 19 atcgtgcta                                                                9

<210> SEQ ID NO 20
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: iSpC3 is inserted between nucleotide positions 5 and 6.

<400> SEQUENCE: 20 atcgtgcta                                                                9

<210> SEQ ID NO 21
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: 2 iFQ's are inserted between nucleotide positions 3 and 4.

<400> SEQUENCE: 21
atcgttgcta                                                              10

<210> SEQ ID NO 22
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: iFQ is inserted between nucleotide positions 3 and 4.
<220> FEATURE:
<221> NAME/KEY: misc_feature
<222> LOCATION: (6)..(7)

```
<223> OTHER INFORMATION: iFQ is inserted between nucleotide positions 6
      and 7.

<400> SEQUENCE: 22
atcgttgcta                                                                    10

<210> SEQ ID NO 23
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: iFQ is inserted between nucleotide positions 3
      and 4
<220> FEATURE:
<221> NAME/KEY: misc_feature
<222> LOCATION: (5)..(6)
<223> OTHER INFORMATION: iFQ is inserted between nucleotide positions 5
      and 6.
<220> FEATURE:
<221> NAME/KEY: misc_feature
<222> LOCATION: (7)..(8)
<223> OTHER INFORMATION: iFQ is inserted between nucleotide positions 7
      and 8.

<400> SEQUENCE: 23
atcgttgcta                                                                    10

<210> SEQ ID NO 24
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2 iFQ's are inserted between nucleotide
      positions 4 and 5.

<400> SEQUENCE: 24
atcgttgcta                                                                    10

<210> SEQ ID NO 25
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: 2 iFQ's are inserted between nucleotide
      positions 5 and 6.

<400> SEQUENCE: 25
atcgttgcta                                                                    10

<210> SEQ ID NO 26
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
``` and 2.

<400> SEQUENCE: 26
atcgttgcta                                                                10

<210> SEQ ID NO 27
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: iFQ is inserted between nucleotide positions 9
      and 10.

<400> SEQUENCE: 27
atcgttgcta                                                                10

<210> SEQ ID NO 28
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (9)..(10)
<223> OTHER INFORMATION: iFQ is inserted between nucleotide positions 9
      and 10.

<400> SEQUENCE: 28
atcgttgcta                                                                10

<210> SEQ ID NO 29
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iSpC3 is inserted between nucleotide positions
      1 and 2.

<400> SEQUENCE: 29
atcgttgcta                                                                10

<210> SEQ ID NO 30
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: iSpC3 is inserted between nucleotide positions
      9 and 10.

<400> SEQUENCE: 30
atcgttgcta                                                                10

```
<210> SEQ ID NO 31
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iSpC3 is inserted between nucleotide positions
      1 and 2.
<220> FEATURE:
<221> NAME/KEY: misc_feature
<222> LOCATION: (9)..(10)
<223> OTHER INFORMATION: iSpC3 is inserted between nucleotide positions
      9 and 10.

<400> SEQUENCE: 31
atcgttgcta                                                              10

<210> SEQ ID NO 32
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA

<400> SEQUENCE: 32
ucaacaucag ucugauaagc ua                                                22

<210> SEQ ID NO 33
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(4)
<223> OTHER INFORMATION: phosphorothioate linkage
<220> FEATURE:
<221> NAME/KEY: misc_feature
<222> LOCATION: (19)..(22)
<223> OTHER INFORMATION: phosphorothioate linkage

<400> SEQUENCE: 33
ucaacaucag ucugauaagc ua                                                22

<210> SEQ ID NO 34
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methly RNA
<220> FEATURE:
<221> NAME/KEY: misc_feature
<222> LOCATION: (1)..(22)
<223> OTHER INFORMATION: phosphorothioate linkage

<400> SEQUENCE: 34
```
ucaacaucag ucugauaagc ua                                          22

<210> SEQ ID NO 35
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 35
ucaacaucag ucugauaagc ua                                          22

<210> SEQ ID NO 36
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (2)..(21)
<223> OTHER INFORMATION: phosphorothioate linkage
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 36
ucaacaucag ucugauaagc ua                                          22

<210> SEQ ID NO 37
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 37
ucaacaucag ucugauaagc ua                                          22

-continued

<210> SEQ ID NO 38
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (1)..(22)
<223> OTHER INFORMATION: 2' O-methyl RNA

<400> SEQUENCE: 38
ucaacaucag ucugauaagc ua                                              22

<210> SEQ ID NO 39
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (11)..(12)
<223> OTHER INFORMATION: iFQ is inserted between nucleotide positions 11
      and 12.
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 39
ucaacaucag ucugauaagc ua                                              22

<210> SEQ ID NO 40
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(1)
<223> OTHER INFORMATION: DNA
<220> FEATURE:
<221> NAME/KEY: misc_feature
<222> LOCATION: (2)..(2)
<223> OTHER INFORMATION: 2' O-methyl RNA, Locked nucleic acid
<220> FEATURE:
<221> NAME/KEY: misc_feature
<222> LOCATION: (3)..(4)
<223> OTHER INFORMATION: DNA
<220> FEATURE:
<221> NAME/KEY: misc_feature
<222> LOCATION: (5)..(5)

```
<223> OTHER INFORMATION: 2' O-methyl RNA, Locked nucleic acid
<220> FEATURE:
<221> NAME/KEY: misc_feature
<222> LOCATION: (6)..(7)
<223> OTHER INFORMATION: DNA
<220> FEATURE:
<221> NAME/KEY: misc_feature
<222> LOCATION: (8)..(8)
<223> OTHER INFORMATION: 2' O-methyl RNA, Locked nucleic acid
<220> FEATURE:
<221> NAME/KEY: misc_feature
<222> LOCATION: (9)..(10)
<223> OTHER INFORMATION: DNA
<220> FEATURE:
<221> NAME/KEY: misc_feature
<222> LOCATION: (11)..(11)
<223> OTHER INFORMATION: 2' O-methyl RNA, Locked nucleic acid
<220> FEATURE:
<221> NAME/KEY: misc_feature
<222> LOCATION: (12)..(13)
<223> OTHER INFORMATION: DNA
<220> FEATURE:
<221> NAME/KEY: misc_feature
<222> LOCATION: (14)..(14)
<223> OTHER INFORMATION: 2' O-methyl RNA, Locked nucleic acid
<220> FEATURE:
<221> NAME/KEY: misc_feature
<222> LOCATION: (15)..(16)
<223> OTHER INFORMATION: DNA
<220> FEATURE:
<221> NAME/KEY: misc_feature
<222> LOCATION: (17)..(17)
<223> OTHER INFORMATION: 2' O-methyl RNA, Locked nucleic acid
<220> FEATURE:
<221> NAME/KEY: misc_feature
<222> LOCATION: (18)..(19)
<223> OTHER INFORMATION: DNA
<220> FEATURE:
<221> NAME/KEY: misc_feature
<222> LOCATION: (20)..(20)
<223> OTHER INFORMATION: 2' O-methyl RNA, Locked nucleic acid
<220> FEATURE:
<221> NAME/KEY: misc_feature
<222> LOCATION: (21)..(22)
<223> OTHER INFORMATION: DNA

<400> SEQUENCE: 40
tcaacatcag tctgataagc ta                                              22

<210> SEQ ID NO 41
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid
<220> FEATURE:
<221> NAME/KEY: misc_feature
```

```
<222> LOCATION: (11)..(11)
<223> OTHER INFORMATION: Locked nucleic acid
<220> FEATURE:
<221> NAME/KEY: misc_feature
<222> LOCATION: (14)..(14)
<223> OTHER INFORMATION: Locked nucleic acid
<220> FEATURE:
<221> NAME/KEY: misc_feature
<222> LOCATION: (17)..(17)
<223> OTHER INFORMATION: Locked nucleic acid
<220> FEATURE:
<221> NAME/KEY: misc_feature
<222> LOCATION: (20)..(20)
<223> OTHER INFORMATION: Locked nucleic acid

<400> SEQUENCE: 41
ucaacaucag tcugauaagc ua                                              22

<210> SEQ ID NO 42
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 42
ucaacaucag ucucauaagc ua                                              22

<210> SEQ ID NO 43
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 43
ucaagaucag ucucauaagc ua                                              22

<210> SEQ ID NO 44
<211> LENGTH: 22
<212> TYPE: RNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 44
ucaagaucag ucucauaagg ua                                                  22

<210> SEQ ID NO 45
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(1)
<223> OTHER INFORMATION: DNA
<220> FEATURE:
<221> NAME/KEY: misc_feature
<222> LOCATION: (2)..(2)
<223> OTHER INFORMATION: 2' O-methyl RNA, Locked nucleic acid
<220> FEATURE:
<221> NAME/KEY: misc_feature
<222> LOCATION: (3)..(4)
<223> OTHER INFORMATION: DNA
<220> FEATURE:
<221> NAME/KEY: misc_feature
<222> LOCATION: (5)..(5)
<223> OTHER INFORMATION: 2' O-methyl RNA, Locked nucleic acid
<220> FEATURE:
<221> NAME/KEY: misc_feature
<222> LOCATION: (6)..(7)
<223> OTHER INFORMATION: DNA
<220> FEATURE:
<221> NAME/KEY: misc_feature
<222> LOCATION: (8)..(8)
<223> OTHER INFORMATION: 2' O-methyl RNA, Locked nucleic acid
<220> FEATURE:
<221> NAME/KEY: misc_feature
<222> LOCATION: (9)..(10)
<223> OTHER INFORMATION: DNA
<220> FEATURE:
<221> NAME/KEY: misc_feature
<222> LOCATION: (11)..(11)
<223> OTHER INFORMATION: 2' O-methyl RNA, Locked nucleic acid
<220> FEATURE:
<221> NAME/KEY: misc_feature
<222> LOCATION: (12)..(13)
<223> OTHER INFORMATION: DNA
<220> FEATURE:
<221> NAME/KEY: misc_feature
<222> LOCATION: (14)..(14)
<223> OTHER INFORMATION: 2' O-methyl RNA, Locked nucleic acid
<220> FEATURE:
<221> NAME/KEY: misc_feature
<222> LOCATION: (15)..(16)
<223> OTHER INFORMATION: DNA
<220> FEATURE:
<221> NAME/KEY: misc_feature
<222> LOCATION: (17)..(17)
<223> OTHER INFORMATION: 2' O-methyl RNA, Locked nucleic acid
<220> FEATURE:
<221> NAME/KEY: misc_feature
```

-continued

```
<222> LOCATION: (18)..(19)
<223> OTHER INFORMATION: DNA
<220> FEATURE:
<221> NAME/KEY: misc_feature
<222> LOCATION: (20)..(20)
<223> OTHER INFORMATION: 2' O-methyl RNA, Locked nucleic acid
<220> FEATURE:
<221> NAME/KEY: misc_feature
<222> LOCATION: (21)..(22)
<223> OTHER INFORMATION: DNA

<400> SEQUENCE: 45
tcaacatcag tctcataagc ta                                              22

<210> SEQ ID NO 46
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(1)
<223> OTHER INFORMATION: DNA
<220> FEATURE:
<221> NAME/KEY: misc_feature
<222> LOCATION: (2)..(2)
<223> OTHER INFORMATION: 2' O-methyl RNA, Locked nucleic acid
<220> FEATURE:
<221> NAME/KEY: misc_feature
<222> LOCATION: (3)..(4)
<223> OTHER INFORMATION: DNA
<220> FEATURE:
<221> NAME/KEY: misc_feature
<222> LOCATION: (5)..(5)
<223> OTHER INFORMATION: 2' O-methyl RNA, Locked nucleic acid
<220> FEATURE:
<221> NAME/KEY: misc_feature
<222> LOCATION: (6)..(7)
<223> OTHER INFORMATION: DNA
<220> FEATURE:
<221> NAME/KEY: misc_feature
<222> LOCATION: (8)..(8)
<223> OTHER INFORMATION: 2' O-methyl RNA, Locked nucleic acid
<220> FEATURE:
<221> NAME/KEY: misc_feature
<222> LOCATION: (9)..(10)
<223> OTHER INFORMATION: DNA
<220> FEATURE:
<221> NAME/KEY: misc_feature
<222> LOCATION: (11)..(11)
<223> OTHER INFORMATION: 2' O-methyl RNA, Locked nucleic acid
<220> FEATURE:
<221> NAME/KEY: misc_feature
<222> LOCATION: (12)..(13)
<223> OTHER INFORMATION: DNA
<220> FEATURE:
<221> NAME/KEY: misc_feature
<222> LOCATION: (14)..(14)
<223> OTHER INFORMATION: 2' O-methyl RNA, Locked nucleic acid
<220> FEATURE:
<221> NAME/KEY: misc_feature
<222> LOCATION: (15)..(16)
<223> OTHER INFORMATION: DNA
<220> FEATURE:
<221> NAME/KEY: misc_feature
<222> LOCATION: (17)..(17)
<223> OTHER INFORMATION: 2' O-methyl RNA, Locked nucleic acid
<220> FEATURE:
<221> NAME/KEY: misc_feature
<222> LOCATION: (18)..(19)
<223> OTHER INFORMATION: DNA
<220> FEATURE:
```

```
<221> NAME/KEY: misc_feature
<222> LOCATION: (20)..(20)
<223> OTHER INFORMATION: 2' O-methyl RNA, Locked nucleic acid
<220> FEATURE:
<221> NAME/KEY: misc_feature
<222> LOCATION: (21)..(22)
<223> OTHER INFORMATION: DNA

<400> SEQUENCE: 46
tcaagatcag tctcataagc ta                                        22

<210> SEQ ID NO 47
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(1)
<223> OTHER INFORMATION: DNA
<220> FEATURE:
<221> NAME/KEY: misc_feature
<222> LOCATION: (2)..(2)
<223> OTHER INFORMATION: 2' O-methyl RNA, Locked nucleic acid
<220> FEATURE:
<221> NAME/KEY: misc_feature
<222> LOCATION: (3)..(4)
<223> OTHER INFORMATION: DNA
<220> FEATURE:
<221> NAME/KEY: misc_feature
<222> LOCATION: (5)..(5)
<223> OTHER INFORMATION: 2' O-methyl RNA, Locked nucleic acid
<220> FEATURE:
<221> NAME/KEY: misc_feature
<222> LOCATION: (6)..(7)
<223> OTHER INFORMATION: DNA
<220> FEATURE:
<221> NAME/KEY: misc_feature
<222> LOCATION: (8)..(8)
<223> OTHER INFORMATION: 2' O-methyl RNA, Locked nucleic acid
<220> FEATURE:
<221> NAME/KEY: misc_feature
<222> LOCATION: (9)..(10)
<223> OTHER INFORMATION: DNA
<220> FEATURE:
<221> NAME/KEY: misc_feature
<222> LOCATION: (11)..(11)
<223> OTHER INFORMATION: 2' O-methyl RNA, Locked nucleic acid
<220> FEATURE:
<221> NAME/KEY: misc_feature
<222> LOCATION: (12)..(13)
<223> OTHER INFORMATION: DNA
<220> FEATURE:
<221> NAME/KEY: misc_feature
<222> LOCATION: (14)..(14)
<223> OTHER INFORMATION: 2' O-methyl RNA, Locked nucleic acid
<220> FEATURE:
<221> NAME/KEY: misc_feature
<222> LOCATION: (15)..(16)
<223> OTHER INFORMATION: DNA
<220> FEATURE:
<221> NAME/KEY: misc_feature
<222> LOCATION: (17)..(17)
<223> OTHER INFORMATION: 2' O-methyl RNA, Locked nucleic acid
<220> FEATURE:
<221> NAME/KEY: misc_feature
<222> LOCATION: (18)..(19)
<223> OTHER INFORMATION: DNA
<220> FEATURE:
<221> NAME/KEY: misc_feature
<222> LOCATION: (20)..(20)
<223> OTHER INFORMATION: 2' O-methyl RNA, Locked nucleic acid
```

```
<220> FEATURE:
<221> NAME/KEY: misc_feature
<222> LOCATION: (21)..(22)
<223> OTHER INFORMATION: DNA

<400> SEQUENCE: 47
tcaagatcag tctcataagg ta                                                  22

<210> SEQ ID NO 48
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid
<220> FEATURE:
<221> NAME/KEY: misc_feature
<222> LOCATION: (11)..(11)
<223> OTHER INFORMATION: Locked nucleic acid
<220> FEATURE:
<221> NAME/KEY: misc_feature
<222> LOCATION: (14)..(14)
<223> OTHER INFORMATION: Locked nucleic acid
<220> FEATURE:
<221> NAME/KEY: misc_feature
<222> LOCATION: (17)..(17)
<223> OTHER INFORMATION: Locked nucleic acid
<220> FEATURE:
<221> NAME/KEY: misc_feature
<222> LOCATION: (20)..(20)
<223> OTHER INFORMATION: Locked nucleic acid

<400> SEQUENCE: 48
ucaacaucag tcucauaagc ua                                                  22

<210> SEQ ID NO 49
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
```

<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid
<220> FEATURE:
<221> NAME/KEY: misc_feature
<222> LOCATION: (11)..(11)
<223> OTHER INFORMATION: Locked nucleic acid
<220> FEATURE:
<221> NAME/KEY: misc_feature
<222> LOCATION: (14)..(14)
<223> OTHER INFORMATION: Locked nucleic acid
<220> FEATURE:
<221> NAME/KEY: misc_feature
<222> LOCATION: (17)..(17)
<223> OTHER INFORMATION: Locked nucleic acid
<220> FEATURE:
<221> NAME/KEY: misc_feature
<222> LOCATION: (20)..(20)
<223> OTHER INFORMATION: Locked nucleic acid

<400> SEQUENCE: 49
ucaagaucag tcucauaagc ua                                              22

<210> SEQ ID NO 50
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid
<220> FEATURE:
<221> NAME/KEY: misc_feature
<222> LOCATION: (11)..(11)
<223> OTHER INFORMATION: Locked nucleic acid
<220> FEATURE:
<221> NAME/KEY: misc_feature
<222> LOCATION: (14)..(14)
<223> OTHER INFORMATION: Locked nucleic acid
<220> FEATURE:
<221> NAME/KEY: misc_feature
<222> LOCATION: (17)..(17)
<223> OTHER INFORMATION: Locked nucleic acid
<220> FEATURE:
<221> NAME/KEY: misc_feature
<222> LOCATION: (20)..(20)
<223> OTHER INFORMATION: Locked nucleic acid

<400> SEQUENCE: 50
ucaagaucag tcucauaagg ua                                              22

<210> SEQ ID NO 51
<211> LENGTH: 22
<212> TYPE: RNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 51
ucaacaucag ucagauaagc ua                                              22

<210> SEQ ID NO 52
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 52
ucaaccucag ucagauaagc ua                                              22

<210> SEQ ID NO 53
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 53
ucaaccucag ucagauaacc ua                                              22

<210> SEQ ID NO 54
<211> LENGTH: 22
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(1)
<223> OTHER INFORMATION: DNA
<220> FEATURE:
<221> NAME/KEY: misc_feature
<222> LOCATION: (2)..(2)
<223> OTHER INFORMATION: 2' O-methyl RNA, Locked nucleic acid
<220> FEATURE:
<221> NAME/KEY: misc_feature
<222> LOCATION: (3)..(4)
<223> OTHER INFORMATION: DNA
<220> FEATURE:
<221> NAME/KEY: misc_feature
<222> LOCATION: (5)..(5)
<223> OTHER INFORMATION: 2' O-methyl RNA, Locked nucleic acid
<220> FEATURE:
<221> NAME/KEY: misc_feature
<222> LOCATION: (6)..(7)
<223> OTHER INFORMATION: DNA
<220> FEATURE:
<221> NAME/KEY: misc_feature
<222> LOCATION: (8)..(8)
<223> OTHER INFORMATION: 2' O-methyl RNA, Locked nucleic acid
<220> FEATURE:
<221> NAME/KEY: misc_feature
<222> LOCATION: (9)..(10)
<223> OTHER INFORMATION: DNA
<220> FEATURE:
<221> NAME/KEY: misc_feature
<222> LOCATION: (11)..(11)
<223> OTHER INFORMATION: 2' O-methyl RNA, Locked nucleic acid
<220> FEATURE:
<221> NAME/KEY: misc_feature
<222> LOCATION: (12)..(13)
<223> OTHER INFORMATION: DNA
<220> FEATURE:
<221> NAME/KEY: misc_feature
<222> LOCATION: (14)..(14)
<223> OTHER INFORMATION: 2' O-methyl RNA, Locked nucleic acid
<220> FEATURE:
<221> NAME/KEY: misc_feature
<222> LOCATION: (15)..(16)
<223> OTHER INFORMATION: DNA
<220> FEATURE:
<221> NAME/KEY: misc_feature
<222> LOCATION: (17)..(17)
<223> OTHER INFORMATION: 2' O-methyl RNA, Locked nucleic acid
<220> FEATURE:
<221> NAME/KEY: misc_feature
<222> LOCATION: (18)..(19)
<223> OTHER INFORMATION: DNA
<220> FEATURE:
<221> NAME/KEY: misc_feature
<222> LOCATION: (20)..(20)
<223> OTHER INFORMATION: 2' O-methyl RNA, Locked nucleic acid
<220> FEATURE:
<221> NAME/KEY: misc_feature
<222> LOCATION: (21)..(22)
<223> OTHER INFORMATION: DNA

<400> SEQUENCE: 54
tcaacatcag tcagataagc ta                                              22

<210> SEQ ID NO 55
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

<222> LOCATION: (1)..(22)
<223> OTHER INFORMATION: phosphorothioate linkage
<220> FEATURE:
<221> NAME/KEY: misc_feature
<222> LOCATION: (1)..(1)
<223> OTHER INFORMATION: DNA
<220> FEATURE:
<221> NAME/KEY: misc_feature
<222> LOCATION: (2)..(2)
<223> OTHER INFORMATION: 2' O-methyl RNA, Locked nucleic acid
<220> FEATURE:
<221> NAME/KEY: misc_feature
<222> LOCATION: (3)..(4)
<223> OTHER INFORMATION: DNA
<220> FEATURE:
<221> NAME/KEY: misc_feature
<222> LOCATION: (5)..(5)
<223> OTHER INFORMATION: 2' O-methyl RNA, Locked nucleic acid
<220> FEATURE:
<221> NAME/KEY: misc_feature
<222> LOCATION: (6)..(7)
<223> OTHER INFORMATION: DNA
<220> FEATURE:
<221> NAME/KEY: misc_feature
<222> LOCATION: (8)..(8)
<223> OTHER INFORMATION: 2' O-methyl RNA, Locked nucleic acid
<220> FEATURE:
<221> NAME/KEY: misc_feature
<222> LOCATION: (9)..(10)
<223> OTHER INFORMATION: DNA
<220> FEATURE:
<221> NAME/KEY: misc_feature
<222> LOCATION: (11)..(11)
<223> OTHER INFORMATION: 2' O-methyl RNA, Locked nucleic acid
<220> FEATURE:
<221> NAME/KEY: misc_feature
<222> LOCATION: (12)..(13)
<223> OTHER INFORMATION: DNA
<220> FEATURE:
<221> NAME/KEY: misc_feature
<222> LOCATION: (14)..(14)
<223> OTHER INFORMATION: 2' O-methyl RNA, Locked nucleic acid
<220> FEATURE:
<221> NAME/KEY: misc_feature
<222> LOCATION: (15)..(16)
<223> OTHER INFORMATION: DNA
<220> FEATURE:
<221> NAME/KEY: misc_feature
<222> LOCATION: (17)..(17)
<223> OTHER INFORMATION: 2' O-methyl RNA, Locked nucleic acid
<220> FEATURE:
<221> NAME/KEY: misc_feature
<222> LOCATION: (18)..(19)
<223> OTHER INFORMATION: DNA
<220> FEATURE:
<221> NAME/KEY: misc_feature
<222> LOCATION: (20)..(20)
<223> OTHER INFORMATION: 2' O-methyl RNA, Locked nucleic acid
<220> FEATURE:
<221> NAME/KEY: misc_feature
<222> LOCATION: (21)..(22)
<223> OTHER INFORMATION: DNA

<400> SEQUENCE: 55
tcaacctcag tcagataagc ta                                              22

<210> SEQ ID NO 56
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:

<221> NAME/KEY: misc_feature
<222> LOCATION: (1)..(1)
<223> OTHER INFORMATION: DNA
<220> FEATURE:
<221> NAME/KEY: misc_feature
<222> LOCATION: (2)..(2)
<223> OTHER INFORMATION: 2' O-methyl RNA, Locked nucleic acid
<220> FEATURE:
<221> NAME/KEY: misc_feature
<222> LOCATION: (3)..(4)
<223> OTHER INFORMATION: DNA
<220> FEATURE:
<221> NAME/KEY: misc_feature
<222> LOCATION: (5)..(5)
<223> OTHER INFORMATION: 2' O-methyl RNA, Locked nucleic acid
<220> FEATURE:
<221> NAME/KEY: misc_feature
<222> LOCATION: (6)..(7)
<223> OTHER INFORMATION: DNA
<220> FEATURE:
<221> NAME/KEY: misc_feature
<222> LOCATION: (8)..(8)
<223> OTHER INFORMATION: 2' O-methyl RNA, Locked nucleic acid
<220> FEATURE:
<221> NAME/KEY: misc_feature
<222> LOCATION: (9)..(10)
<223> OTHER INFORMATION: DNA
<220> FEATURE:
<221> NAME/KEY: misc_feature
<222> LOCATION: (11)..(11)
<223> OTHER INFORMATION: 2' O-methyl RNA, Locked nucleic acid
<220> FEATURE:
<221> NAME/KEY: misc_feature
<222> LOCATION: (12)..(13)
<223> OTHER INFORMATION: DNA
<220> FEATURE:
<221> NAME/KEY: misc_feature
<222> LOCATION: (14)..(14)
<223> OTHER INFORMATION: 2' O-methyl RNA, Locked nucleic acid
<220> FEATURE:
<221> NAME/KEY: misc_feature
<222> LOCATION: (15)..(16)
<223> OTHER INFORMATION: DNA
<220> FEATURE:
<221> NAME/KEY: misc_feature
<222> LOCATION: (17)..(17)
<223> OTHER INFORMATION: 2' O-methyl RNA, Locked nucleic acid
<220> FEATURE:
<221> NAME/KEY: misc_feature
<222> LOCATION: (18)..(19)
<223> OTHER INFORMATION: DNA
<220> FEATURE:
<221> NAME/KEY: misc_feature
<222> LOCATION: (20)..(20)
<223> OTHER INFORMATION: 2' O-methyl RNA, Locked nucleic acid
<220> FEATURE:
<221> NAME/KEY: misc_feature
<222> LOCATION: (21)..(22)
<223> OTHER INFORMATION: DNA

<400> SEQUENCE: 56
tcaacctcag tcagataacc ta                                              22

<210> SEQ ID NO 57
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(22)
<223> OTHER INFORMATION: 2' O-methyl RNA

```
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid
<220> FEATURE:
<221> NAME/KEY: misc_feature
<222> LOCATION: (11)..(11)
<223> OTHER INFORMATION: Locked nucleic acid
<220> FEATURE:
<221> NAME/KEY: misc_feature
<222> LOCATION: (14)..(14)
<223> OTHER INFORMATION: Locked nucleic acid
<220> FEATURE:
<221> NAME/KEY: misc_feature
<222> LOCATION: (17)..(17)
<223> OTHER INFORMATION: Locked nucleic acid
<220> FEATURE:
<221> NAME/KEY: misc_feature
<222> LOCATION: (20)..(20)
<223> OTHER INFORMATION: Locked nucleic acid

<400> SEQUENCE: 57
ucaacaucag tcagauaagc ua                                              22

<210> SEQ ID NO 58
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid
<220> FEATURE:
<221> NAME/KEY: misc_feature
<222> LOCATION: (11)..(11)
<223> OTHER INFORMATION: Locked nucleic acid
<220> FEATURE:
<221> NAME/KEY: misc_feature
<222> LOCATION: (14)..(14)
<223> OTHER INFORMATION: Locked nucleic acid
<220> FEATURE:
<221> NAME/KEY: misc_feature
<222> LOCATION: (17)..(17)
<223> OTHER INFORMATION: Locked nucleic acid
<220> FEATURE:
<221> NAME/KEY: misc_feature
<222> LOCATION: (20)..(20)
<223> OTHER INFORMATION: Locked nucleic acid

<400> SEQUENCE: 58
```
ucaaccucag tcagauaagc ua                                          22

<210> SEQ ID NO 59
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid
<220> FEATURE:
<221> NAME/KEY: misc_feature
<222> LOCATION: (11)..(11)
<223> OTHER INFORMATION: Locked nucleic acid
<220> FEATURE:
<221> NAME/KEY: misc_feature
<222> LOCATION: (14)..(14)
<223> OTHER INFORMATION: Locked nucleic acid
<220> FEATURE:
<221> NAME/KEY: misc_feature
<222> LOCATION: (17)..(17)
<223> OTHER INFORMATION: Locked nucleic acid
<220> FEATURE:
<221> NAME/KEY: misc_feature
<222> LOCATION: (20)..(20)
<223> OTHER INFORMATION: Locked nucleic acid

<400> SEQUENCE: 59
ucaaccucag tcagauaacc ua                                          22

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
ataggactcc agatgtttcc                                             20

<210> SEQ ID NO 61
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.

<400> SEQUENCE: 61
ataggactcc agatgtttcc                                             20

<210> SEQ ID NO 62
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: iFQ is inserted between nucleotide positions 19 and 20.

<400> SEQUENCE: 62
ataggactcc agatgtttcc                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1 and 2.
<220> FEATURE:
<221> NAME/KEY: misc_feature
<222> LOCATION: (19)..(20)
<223> OTHER INFORMATION: iFQ is inserted between nucleotide positions 19 and 20.

<400> SEQUENCE: 63
ataggactcc agatgtttcc                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1 and 2.
<220> FEATURE:
<221> NAME/KEY: misc_feature
<222> LOCATION: (10)..(11)
<223> OTHER INFORMATION: iFQ is inserted between nucleotide positions 10 and 11.
<220> FEATURE:
<221> NAME/KEY: misc_feature
<222> LOCATION: (19)..(20)
<223> OTHER INFORMATION: iFQ is inserted between nucleotide positions 19 and 20.

<400> SEQUENCE: 64
ataggactcc agatgtttcc                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: phosphorothioate linkage

<400> SEQUENCE: 65

```
ataggactcc agatgtttcc                                         20

<210> SEQ ID NO 66
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (2)..(20)
<223> OTHER INFORMATION: phosphorothioate linkage

<400> SEQUENCE: 66
ataggactcc agatgtttcc                                         20

<210> SEQ ID NO 67
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: phosphorothioate linkage
<220> FEATURE:
<221> NAME/KEY: misc_feature
<222> LOCATION: (19)..(20)
<223> OTHER INFORMATION: iFQ is inserted between nucleotide positions 19
      and 20.

<400> SEQUENCE: 67
ataggactcc agatgtttcc                                         20

<210> SEQ ID NO 68
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (2)..(19)
<223> OTHER INFORMATION: phosphorothioate linkage
<220> FEATURE:
<221> NAME/KEY: misc_feature
<222> LOCATION: (19)..(20)
<223> OTHER INFORMATION: iFQ is inserted between nucleotide positions 19
      and 20.

<400> SEQUENCE: 68
ataggactcc agatgtttcc                                         20

<210> SEQ ID NO 69
<211> LENGTH: 20
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (2)..(10)
<223> OTHER INFORMATION: phosphorothioate linkage
<220> FEATURE:
<221> NAME/KEY: misc_feature
<222> LOCATION: (10)..(11)
<223> OTHER INFORMATION: iFQ is inserted between nucleotide positions 10
      and 11.
<220> FEATURE:
<221> NAME/KEY: misc_feature
<222> LOCATION: (11)..(19)
<223> OTHER INFORMATION: phosphorothioate linkage
<220> FEATURE:
<221> NAME/KEY: misc_feature
<222> LOCATION: (19)..(20)
<223> OTHER INFORMATION: iFQ is inserted between nucleotide positions 19
      and 20.

<400> SEQUENCE: 69
ataggactcc agatgtttcc                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: 2' O-methyl RNA
<220> FEATURE:
<221> NAME/KEY: misc_feature
<222> LOCATION: (6)..(15)
<223> OTHER INFORMATION: DNA
<220> FEATURE:
<221> NAME/KEY: misc_feature
<222> LOCATION: (16)..(20)
<223> OTHER INFORMATION: 2' O-methyl RNA

<400> SEQUENCE: 70
auaggactcc agatguuucc                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (1)..(5)
<223> OTHER INFORMATION: 2' O-methyl RNA
<220> FEATURE:
<221> NAME/KEY: misc_feature
<222> LOCATION: (6)..(15)
<223> OTHER INFORMATION: DNA
<220> FEATURE:
<221> NAME/KEY: misc_feature
<222> LOCATION: (16)..(20)
<223> OTHER INFORMATION: 2' O-methyl RNA
<220> FEATURE:
<221> NAME/KEY: misc_feature
<222> LOCATION: (19)..(20)
<223> OTHER INFORMATION: iFQ is inserted between nucleotide positions 19
``` and 20.

<400> SEQUENCE: 71
auaggactcc agatguuucc                                                      20

<210> SEQ ID NO 72
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (1)..(5)
<223> OTHER INFORMATION: 2' O-methyl RNA
<220> FEATURE:
<221> NAME/KEY: misc_feature
<222> LOCATION: (6)..(15)
<223> OTHER INFORMATION: DNA
<220> FEATURE:
<221> NAME/KEY: misc_feature
<222> LOCATION: (10)..(11)
<223> OTHER INFORMATION: iFQ is inserted between nucleotide positions 10
      and 11.
<220> FEATURE:
<221> NAME/KEY: misc_feature
<222> LOCATION: (16)..(20)
<223> OTHER INFORMATION: 2' O-methyl RNA
<220> FEATURE:
<221> NAME/KEY: misc_feature
<222> LOCATION: (19)..(20)
<223> OTHER INFORMATION: iFQ is inserted between nucleotide positions 19
      and 20.

<400> SEQUENCE: 72
auaggactcc agatguuucc                                                      20

<210> SEQ ID NO 73
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: misc_feature
<222> LOCATION: (1)..(5)
<223> OTHER INFORMATION: 2' O-methyl RNA
<220> FEATURE:
<221> NAME/KEY: misc_feature
<222> LOCATION: (6)..(15)
<223> OTHER INFORMATION: DNA
<220> FEATURE:
<221> NAME/KEY: misc_feature
<222> LOCATION: (16)..(20)
<223> OTHER INFORMATION: 2' O-methyl RNA

<400> SEQUENCE: 73
auaggactcc agatguuucc                                                      20

<210> SEQ ID NO 74
<211> LENGTH: 20
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (1)..(5)
<223> OTHER INFORMATION: 2' O-methyl RNA
<220> FEATURE:
<221> NAME/KEY: misc_feature
<222> LOCATION: (2)..(19)
<223> OTHER INFORMATION: phosphorothioate linkage
<220> FEATURE:
<221> NAME/KEY: misc_feature
<222> LOCATION: (6)..(15)
<223> OTHER INFORMATION: DNA
<220> FEATURE:
<221> NAME/KEY: misc_feature
<222> LOCATION: (16)..(20)
<223> OTHER INFORMATION: 2' O-methyl RNA
<220> FEATURE:
<221> NAME/KEY: misc_feature
<222> LOCATION: (19)..(20)
<223> OTHER INFORMATION: iFQ is inserted between nucleotide positions 19
      and 20.

<400> SEQUENCE: 74
auaggactcc agatguuucc                                                   20

<210> SEQ ID NO 75
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: 2' O-methyl RNA
<220> FEATURE:
<221> NAME/KEY: misc_feature
<222> LOCATION: (6)..(15)
<223> OTHER INFORMATION: DNA
<220> FEATURE:
<221> NAME/KEY: misc_feature
<222> LOCATION: (6)..(16)
<223> OTHER INFORMATION: phosphorothioate linkage
<220> FEATURE:
<221> NAME/KEY: misc_feature
<222> LOCATION: (16)..(20)
<223> OTHER INFORMATION: 2' O-methyl RNA

<400> SEQUENCE: 75
auaggactcc agatguuucc                                                   20

<210> SEQ ID NO 76
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (1)..(5)
<223> OTHER INFORMATION: 2' O-methyl RNA
<220> FEATURE:
<221> NAME/KEY: misc_feature
<222> LOCATION: (6)..(15)
```

```
<223> OTHER INFORMATION: DNA
<220> FEATURE:
<221> NAME/KEY: misc_feature
<222> LOCATION: (6)..(16)
<223> OTHER INFORMATION: phosphorothioate linkage
<220> FEATURE:
<221> NAME/KEY: misc_feature
<222> LOCATION: (16)..(20)
<223> OTHER INFORMATION: 2' O-methyl RNA
<220> FEATURE:
<221> NAME/KEY: misc_feature
<222> LOCATION: (19)..(20)
<223> OTHER INFORMATION: iFQ is inserted between nucleotide positions 19
      and 20.

<400> SEQUENCE: 76
auaggactcc agatguuucc                                                        20

<210> SEQ ID NO 77
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (1)..(5)
<223> OTHER INFORMATION: 2' O-methyl RNA
<220> FEATURE:
<221> NAME/KEY: misc_feature
<222> LOCATION: (6)..(15)
<223> OTHER INFORMATION: DNA
<220> FEATURE:
<221> NAME/KEY: misc_feature
<222> LOCATION: (6)..(16)
<223> OTHER INFORMATION: phosphorothioate linkage
<220> FEATURE:
<221> NAME/KEY: misc_feature
<222> LOCATION: (10)..(11)
<223> OTHER INFORMATION: iFQ is inserted between nucleotide positions 10
      and 11.
<220> FEATURE:
<221> NAME/KEY: misc_feature
<222> LOCATION: (16)..(20)
<223> OTHER INFORMATION: 2' O-methyl RNA
<220> FEATURE:
<221> NAME/KEY: misc_feature
<222> LOCATION: (19)..(20)
<223> OTHER INFORMATION: iFQ is inserted between nucleotide positions 19
      and 20.

<400> SEQUENCE: 77
auaggactcc agatguuucc                                                        20

<210> SEQ ID NO 78
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: misc_feature
<222> LOCATION: (1)..(5)
<223> OTHER INFORMATION: 2' O-methyl RNA, Locked nucleic acid
<220> FEATURE:
<221> NAME/KEY: misc_feature
```

```
<222> LOCATION: (6)..(15)
<223> OTHER INFORMATION: DNA
<220> FEATURE:
<221> NAME/KEY: misc_feature
<222> LOCATION: (16)..(20)
<223> OTHER INFORMATION: 2' O-methyl RNA, Locked nucleic acid

<400> SEQUENCE: 78
auaggactcc agatguuucc                                          20

<210> SEQ ID NO 79
<211> LENGTH: 24
<212> TYPE: DNA
<213> ORGANISM: Artificial Sequence
<220> FEATURE:
<223> OTHER INFORMATION: Synthetic

<400> SEQUENCE: 79
gactttgctt tccttggtca ggca                                     24

<210> SEQ ID NO 80
<211> LENGTH: 24
<212> TYPE: DNA
<213> ORGANISM: Artificial Sequence
<220> FEATURE:
<223> OTHER INFORMATION: Synthetic

<400> SEQUENCE: 80
ggcttatatc caacacttcg tggg                                     24

<210> SEQ ID NO 81
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' MAX (NHS Ester)
<220> FEATURE:
<221> NAME/KEY: misc_feature
<222> LOCATION: (26)..(26)
<223> OTHER INFORMATION: 3' Iowa Black FQ

<400> SEQUENCE: 81
atggtcaagg tcgcaagctt gctggt                                   26

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
ggcgacctgg aagtccaact                                          20

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
ccatcagcac cacagccttc                                          20
```

```
<210> SEQ ID NO 84
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'  FAM (Fluorescein)
<220> FEATURE:
<221> NAME/KEY: misc_feature
<222> LOCATION: (25)..(25)
<223> OTHER INFORMATION: 3' Iowa Black FQ

<400> SEQUENCE: 84
atctgctgca tctgcttgga gccca                                             25

<210> SEQ ID NO 85
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (24)..(25)
<223> OTHER INFORMATION: DNA

<400> SEQUENCE: 85
cguuaaucgc guauaauacg cguat                                             25

<210> SEQ ID NO 86
<211> LENGTH: 27
<212> TYPE: RNA
<213> ORGANISM: Artificial Sequence
<220> FEATURE:
<223> OTHER INFORMATION: Synthetic

<400> SEQUENCE: 86
auacgcguau uauacgcgau uaacgac                                           27

<210> SEQ ID NO 87
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (24)..(25)
<223> OTHER INFORMATION: DNA

<400> SEQUENCE: 87
gccagacuuu guuggauuug aaatt                                             25

<210> SEQ ID NO 88
<211> LENGTH: 27
<212> TYPE: RNA
<213> ORGANISM: Artificial Sequence
<220> FEATURE:
<223> OTHER INFORMATION: Synthetic
```

<400> SEQUENCE: 88
aauuucaaau ccaacaaagu cugguuc                                                27

<210> SEQ ID NO 89
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (24)..(25)
<223> OTHER INFORMATION: DNA

<400> SEQUENCE: 89
gccagacuuu guuggauuug aaatt                                                  25

<210> SEQ ID NO 90
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(27)
<223> OTHER INFORMATION: RNA
<220> FEATURE:
<221> NAME/KEY: misc_feature
<222> LOCATION: (26)..(27)
<223> OTHER INFORMATION: iFQ is inserted between nucleotide positions 26
      and 27.

<400> SEQUENCE: 90
aauuucaaac cuaacaaagu cuggucu                                                27

<210> SEQ ID NO 91
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (24)..(25)
<223> OTHER INFORMATION: DNA

<400> SEQUENCE: 91
gccagacuuu guuggauuug aaatt                                                  25

<210> SEQ ID NO 92
<211> LENGTH: 27
<212> TYPE: RNA
<213> ORGANISM: Artificial Sequence
<220> FEATURE:
<223> OTHER INFORMATION: Synthetic

```
<400> SEQUENCE: 92
aauuucaaau ccaacaaagu cuggcuu                                    27

<210> SEQ ID NO 93
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (24)..(25)
<223> OTHER INFORMATION: iFQ is inserted between nucleotide positions 24
      and 25.
<220> FEATURE:
<221> NAME/KEY: misc_feature
<222> LOCATION: (24)..(25)
<223> OTHER INFORMATION: DNA

<400> SEQUENCE: 93
gccagacuuu guuggauuug aaatt                                      25

<210> SEQ ID NO 94
<211> LENGTH: 27
<212> TYPE: RNA
<213> ORGANISM: Artificial Sequence
<220> FEATURE:
<223> OTHER INFORMATION: Synthetic

<400> SEQUENCE: 94
aauuucaaau ccaacaaagu cuggcuu                                    27

<210> SEQ ID NO 95
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (24)..(25)
<223> OTHER INFORMATION: DNA

<400> SEQUENCE: 95
gccagacuuu guuggauuug aaatt                                      25

<210> SEQ ID NO 96
<211> LENGTH: 27
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(25)
<223> OTHER INFORMATION: iFQ is inserted between nucleotide positions 24
      and 25.
```

```
<400> SEQUENCE: 96
aauuucaaau ccaacaaagu cuggcuu                                              27

<210> SEQ ID NO 97
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (24)..(25)
<223> OTHER INFORMATION: DNA

<400> SEQUENCE: 97
gccagacuuu guuggauuug aaatt                                                25

<210> SEQ ID NO 98
<211> LENGTH: 27
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (24)..(25)
<223> OTHER INFORMATION: iFQ is inserted between nucleotide positions 24
      and 25.

<400> SEQUENCE: 98
aauuucaaau ccaacaaagu cuggcuu                                              27

<210> SEQ ID NO 99
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (24)..(25)
<223> OTHER INFORMATION: iFQ is inserted between nucleotide positions 24
      and 25.
<220> FEATURE:
<221> NAME/KEY: misc_feature
<222> LOCATION: (24)..(25)
<223> OTHER INFORMATION: DNA

<400> SEQUENCE: 99
gccagacuuu guuggauuug aaatt                                                25

<210> SEQ ID NO 100
<211> LENGTH: 27
```

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(25)
<223> OTHER INFORMATION: iFQ is inserted between nucleotide positions 24
      and 25.

<400> SEQUENCE: 100
aauuucaaau ccaacaaagu cugguuc                                              27

<210> SEQ ID NO 101
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (24)..(25)
<223> OTHER INFORMATION: iFQ is inserted between nucleotide positions 24
      and 25.
<220> FEATURE:
<221> NAME/KEY: misc_feature
<222> LOCATION: (24)..(25)
<223> OTHER INFORMATION: DNA

<400> SEQUENCE: 101
gccagacuuu guuggauuug aaatt                                                25

<210> SEQ ID NO 102
<211> LENGTH: 27
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (24)..(25)
<223> OTHER INFORMATION: iFQ is inserted between nucleotide positions 24
      and 25.

<400> SEQUENCE: 102
aauuucaaau ccaacaaagu cuggcuu                                              27

<210> SEQ ID NO 103
<211> LENGTH: 18
<212> TYPE: DNA
<213> ORGANISM: Artificial Sequence
<220> FEATURE:
<223> OTHER INFORMATION: Synthetic

<400> SEQUENCE: 103
tgtgcagaag gatggagt                                                        18
```

-continued

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
ctggtgcttc tctcaggata                                               20

<210> SEQ ID NO 105
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' MAX (NHS Ester)
<220> FEATURE:
<221> NAME/KEY: misc_feature
<222> LOCATION: (25)..(25)
<223> OTHER INFORMATION: 3' Iowa Black FQ

<400> SEQUENCE: 105
tggaatatgc cctgcgtaaa ctgga                                          25

<210> SEQ ID NO 106
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: iFQ is inserted between nucleotide positions 1
      and 2.
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (21)..(22)
<223> OTHER INFORMATION: iFQ is inserted between nucleotide positions 21
      and 22.

<400> SEQUENCE: 106
gcguauuaua gccgauuaac ga                                             22

<210> SEQ ID NO 107
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: phosphorothioate linkage
<220> FEATURE:
<221> NAME/KEY: misc_feature
<222> LOCATION: (1)..(22)
<223> OTHER INFORMATION: 2' O-methyl RNA
<220> FEATURE:
<221> NAME/KEY: misc_feature
<222> LOCATION: (19)..(22)
<223> OTHER INFORMATION: phosphorothioate linkage

<400> SEQUENCE: 107
gcguauuaua gccgauuaac ga                                    22

<210> SEQ ID NO 108
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage

<400> SEQUENCE: 108
gcgtattata gccgattaac ga                                    22

<210> SEQ ID NO 109
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: DNA
<220> FEATURE:
<221> NAME/KEY: misc_feature
<222> LOCATION: (2)..(2)
<223> OTHER INFORMATION: 2' O-methyl RNA, Locked nucleic acid
<220> FEATURE:
<221> NAME/KEY: misc_feature
<222> LOCATION: (3)..(4)
<223> OTHER INFORMATION: DNA
<220> FEATURE:
<221> NAME/KEY: misc_feature
<222> LOCATION: (5)..(5)
<223> OTHER INFORMATION: 2' O-methyl RNA, Locked nucleic acid
<220> FEATURE:
<221> NAME/KEY: misc_feature
<222> LOCATION: (6)..(7)
<223> OTHER INFORMATION: DNA
<220> FEATURE:
<221> NAME/KEY: misc_feature
<222> LOCATION: (8)..(8)
<223> OTHER INFORMATION: 2' O-methyl RNA, Locked nucleic acid
<220> FEATURE:
<221> NAME/KEY: misc_feature
<222> LOCATION: (9)..(10)
<223> OTHER INFORMATION: DNA
<220> FEATURE:
<221> NAME/KEY: misc_feature
<222> LOCATION: (11)..(11)
<223> OTHER INFORMATION: 2' O-methyl RNA, Locked nucleic acid
<220> FEATURE:
<221> NAME/KEY: misc_feature
<222> LOCATION: (12)..(13)
<223> OTHER INFORMATION: DNA
<220> FEATURE:
<221> NAME/KEY: misc_feature
<222> LOCATION: (14)..(14)
<223> OTHER INFORMATION: 2' O-methyl RNA, Locked nucleic acid
<220> FEATURE:
<221> NAME/KEY: misc_feature
<222> LOCATION: (15)..(16)
<223> OTHER INFORMATION: DNA
<220> FEATURE:
<221> NAME/KEY: misc_feature
<222> LOCATION: (17)..(17)
<223> OTHER INFORMATION: 2' O-methyl RNA, Locked nucleic acid
<220> FEATURE:
<221> NAME/KEY: misc_feature
<222> LOCATION: (18)..(19)
<223> OTHER INFORMATION: DNA
<220> FEATURE:
<221> NAME/KEY: misc_feature

```
<222> LOCATION: (20)..(20)
<223> OTHER INFORMATION: 2' O-methyl RNA, Locked nucleic acid
<220> FEATURE:
<221> NAME/KEY: misc_feature
<222> LOCATION: (21)..(22)
<223> OTHER INFORMATION: DNA

<400> SEQUENCE: 109
gcgtattata gccgattaac ga                                              22

<210> SEQ ID NO 110
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(1)
<223> OTHER INFORMATION: DNA
<220> FEATURE:
<221> NAME/KEY: misc_feature
<222> LOCATION: (2)..(2)
<223> OTHER INFORMATION: 2' O-methyl RNA, Locked nucleic acid
<220> FEATURE:
<221> NAME/KEY: misc_feature
<222> LOCATION: (3)..(4)
<223> OTHER INFORMATION: DNA
<220> FEATURE:
<221> NAME/KEY: misc_feature
<222> LOCATION: (5)..(5)
<223> OTHER INFORMATION: 2' O-methyl RNA, Locked nucleic acid
<220> FEATURE:
<221> NAME/KEY: misc_feature
<222> LOCATION: (6)..(7)
<223> OTHER INFORMATION: DNA
<220> FEATURE:
<221> NAME/KEY: misc_feature
<222> LOCATION: (8)..(8)
<223> OTHER INFORMATION: 2' O-methyl RNA, Locked nucleic acid
<220> FEATURE:
<221> NAME/KEY: misc_feature
<222> LOCATION: (9)..(10)
<223> OTHER INFORMATION: DNA
<220> FEATURE:
<221> NAME/KEY: misc_feature
<222> LOCATION: (11)..(11)
<223> OTHER INFORMATION: 2' O-methyl RNA, Locked nucleic acid
<220> FEATURE:
<221> NAME/KEY: misc_feature
<222> LOCATION: (12)..(13)
<223> OTHER INFORMATION: DNA
<220> FEATURE:
<221> NAME/KEY: misc_feature
<222> LOCATION: (14)..(14)
<223> OTHER INFORMATION: 2' O-methyl RNA, Locked nucleic acid
<220> FEATURE:
<221> NAME/KEY: misc_feature
<222> LOCATION: (15)..(16)
<223> OTHER INFORMATION: DNA
<220> FEATURE:
<221> NAME/KEY: misc_feature
<222> LOCATION: (17)..(17)
<223> OTHER INFORMATION: 2' O-methyl RNA, Locked nucleic acid
<220> FEATURE:
<221> NAME/KEY: misc_feature
<222> LOCATION: (18)..(19)
<223> OTHER INFORMATION: DNA
<220> FEATURE:
<221> NAME/KEY: misc_feature
<222> LOCATION: (20)..(20)
<223> OTHER INFORMATION: 2' O-methyl RNA, Locked nucleic acid
<220> FEATURE:
```

```
<221> NAME/KEY: misc_feature
<222> LOCATION: (21)..(22)
<223> OTHER INFORMATION: DNA

<400> SEQUENCE: 110
gcgtattata gccgattaac ga                                         22

<210> SEQ ID NO 111
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: 2' O-Methyl RNA
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid
<220> FEATURE:
<221> NAME/KEY: misc_feature
<222> LOCATION: (11)..(11)
<223> OTHER INFORMATION: Locked nucleic acid
<220> FEATURE:
<221> NAME/KEY: misc_feature
<222> LOCATION: (14)..(14)
<223> OTHER INFORMATION: Locked nucleic acid
<220> FEATURE:
<221> NAME/KEY: misc_feature
<222> LOCATION: (17)..(17)
<223> OTHER INFORMATION: Locked nucleic acid
<220> FEATURE:
<221> NAME/KEY: misc_feature
<222> LOCATION: (20)..(20)
<223> OTHER INFORMATION: Locked nucleic acid

<400> SEQUENCE: 111
gcgtattata gccgattaac ga                                         22

<210> SEQ ID NO 112
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: misc_feature
<222> LOCATION: (1)..(22)
<223> OTHER INFORMATION: 2' O-Methyl RNA
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid
```

```
<220> FEATURE:
<221> NAME/KEY: misc_feature
<222> LOCATION: (11)..(11)
<223> OTHER INFORMATION: Locked nucleic acid
<220> FEATURE:
<221> NAME/KEY: misc_feature
<222> LOCATION: (14)..(14)
<223> OTHER INFORMATION: Locked nucleic acid
<220> FEATURE:
<221> NAME/KEY: misc_feature
<222> LOCATION: (17)..(17)
<223> OTHER INFORMATION: Locked nucleic acid
<220> FEATURE:
<221> NAME/KEY: misc_feature
<222> LOCATION: (20)..(20)
<223> OTHER INFORMATION: Locked nucleic acid

<400> SEQUENCE: 112
gcgtattata gccgattaac ga                                           22
```